United States Patent [19]

Mozaffar et al.

[11] Patent Number: 6,096,870

[45] Date of Patent: *Aug. 1, 2000

[54] SEQUENTIAL SEPARATION OF WHEY

[75] Inventors: Zahid Mozaffar, Union City; Salah H. Ahmed, Hayward; Vinit Saxena, Pleasanton; Quirinus Ronnie Miranda, San Jose, all of Calif.

[73] Assignee: Sepragen Corporation, Calif.

[ * ] Notice: This patent is subject to a terminal disclaimer.

[21] Appl. No.: 09/076,169

[22] Filed: May 4, 1998

Related U.S. Application Data

[63] Continuation-in-part of application No. 08/678,364, Jul. 16, 1996, Pat. No. 5,756,680, which is a continuation of application No. 08/177,574, Jan. 5, 1994, abandoned.

[51] Int. Cl.[7] .......................... C07K 16/04; C07K 14/47; A23C 9/12

[52] U.S. Cl. .......................... 530/366; 530/386; 530/394; 530/412; 530/414; 530/417; 530/833; 426/41; 426/583

[58] Field of Search .................................... 530/350, 363, 530/364, 365, 366, 386, 394, 412, 414, 416, 832, 387.1, 417, 833; 426/41, 271, 583; 424/157.1, 535; 435/272

[56] References Cited

U.S. PATENT DOCUMENTS

| | | | |
|---|---|---|---|
| 3,422,605 | 1/1969 | Crowley | 96/105 |
| 3,453,811 | 7/1969 | Crowley | 96/107 |
| 3,780,866 | 12/1973 | Ek et al. | 210/198.2 |
| 3,969,337 | 7/1976 | Lauer et al. | 530/416 |
| 4,133,562 | 1/1979 | Andren | 285/187 |
| 4,202,909 | 5/1980 | Pederson | 426/239 |
| 4,354,932 | 10/1982 | McNeil | 210/198.2 |
| 4,446,164 | 5/1984 | Brog | 426/583 |
| 4,614,653 | 9/1986 | Kakade | 426/2 |
| 4,627,918 | 12/1986 | Saxena | 210/656 |
| 4,668,771 | 5/1987 | Kawakami et al. | 530/366 |
| 4,676,898 | 6/1987 | Saxena | 210/198.2 |
| 4,705,616 | 11/1987 | Andresen et al. | 204/452 |
| 4,708,782 | 11/1987 | Andresen et al. | 210/198.2 |
| 4,740,298 | 4/1988 | Anderesen et al. | 210/198.3 |
| 4,791,193 | 12/1988 | Okonogi et al. | 530/416 |
| 4,820,348 | 4/1989 | Harju | 127/46.2 |
| 4,840,730 | 6/1989 | Saxena | 210/198.2 |
| 4,865,729 | 9/1989 | Saxena et al. | 210/198.2 |
| 4,879,131 | 11/1989 | de Rahm | 426/583 |
| 4,955,363 | 9/1990 | Harju et al. | 127/46.1 |
| 4,997,914 | 3/1991 | Kawakami et al. | 530/395 |
| 5,008,379 | 4/1991 | Bottomley | 534/684 |
| 5,055,558 | 10/1991 | Chianconc et al. | 530/386 |
| 5,077,067 | 12/1991 | Thibault | 426/271 |
| 5,085,881 | 2/1992 | Moeller | 426/491 |
| 5,093,143 | 3/1992 | Behr et al. | 426/583 |
| 5,179,197 | 1/1993 | Uchida et al. | 530/366 |
| 5,420,249 | 5/1995 | de Wit et al. | 530/366 |
| 5,452,659 | 9/1995 | Pupic | 101/415.1 |
| 5,492,723 | 2/1996 | Sanderson et al. | 427/244 |
| 5,756,680 | 5/1998 | Ahmed et al. | 530/366 |

FOREIGN PATENT DOCUMENTS

| | | |
|---|---|---|
| 556 083 | 8/1993 | European Pat. Off. |
| WO 89/10064 | 11/1989 | WIPO |
| WO 92/03468 | 3/1992 | WIPO |
| WO 95/19714 | 7/1995 | WIPO |

OTHER PUBLICATIONS

Ayers and Petersen, "Whey Protein Recovery Using a Range of Novel Ion–Exchangers", New Zealand J. of Dairy Sci. and Tech. 20:129–142 (1985).

Bradley, R.L. et al., "Chemical and Physical Methods, 15.1 Proteins,"in R.T. Marshall (ed.), *Standard Methods for the Examination of Dairy Products*, American Public Health Association, (1992), pp. 504–516.

Chance and Maehly, Meth. Enzymol., 2:773–775 (1995) (reference unavailable).

Etzel, Whey Protein Isolation and Fractionation Using Ion Exchangers in Singh and Rizvi (eds.), *Bioseparation Processes in Foods*, Marcel Dekker, Inc. New York, 1995.

Famighetti, R. (ed.), *World Almanac and Book of Facts*, 1996 Funk & Wagnalls, Mahway, New Jersey (1995), p. 207.

Frandsen (ed.), *Dairy Handbook and Dictionary*, J.H. Frandsen, Amherst, MA (1958), pp. 791–792.

Girardet et al., Milhewissensehatt 44:692–696 (1989).

Karleskind, et al., Foaming Properties of Lipid–Reduced and Calcium–Reduced Whey Protein Concentrates, J. Food Science, 60 (4):738–741.

Kirk, R.W.and S.I. Bistner, *Handbook of Veterinary Procedures and Emergency Treatment*, 2d ed., W.B. Saunders Co., Philadelphia, PA (1975), pp. 644–649.

Lonnerdal and Atkinson, in Jensen (ed.), *Handbook of Milk Composition*, Academic Press, NY, (1995), pp. 358–360.

Pearl, A.M. et al., *Completely Cheese: The Cheeselover's Companion*, Jonathan David Publishers, Inc., Middle Village, New York (1978), p. 59–60.

Rosentahl, *Milk and Dairy Products*, VCH, New York, (1991), p. 137.

Taylor, *Scientific Farm Animal Production*, (5th ed.), Prentice Hall, Englewood Cliffs, NJ, (1995), p. 93.

Zietlow and Etzel, "Evaluation of sulfopropylIon–Exchange Membrane Cartridges for Isolation of Proteins From Bovine Whey", J. Liquid Chromatogr., 1001–1018 (1995).

Girardet et al. Milchwissenschaft. 44(11): 692–969, 1989.

*Primary Examiner*—David Guzo
*Assistant Examiner*—Jon Shuman
*Attorney, Agent, or Firm*—Medlen & Carroll, LLP

[57] ABSTRACT

The present invention is related to the separation of whey proteins, particularly the sequential separation of whey proteins into separate fractions through the use of chromatography. The present invention further provides methods and compositions for the sequential separation of whey proteins, as well as their use in various products. The present invention also provides methods and compositions for the cleaning of chromatography resins used in the separation of whey proteins.

66 Claims, 13 Drawing Sheets

FIGURE 2

Flow Diagram Of Elution Protocol

Whey (1000 ml Skimmed Sweet Whey From
Mozzarella Cheese Manufacture - at 40-50°F, pH 6.4)

↓ pH Adjusted to 3.8 (with Acetic Acid)

↓

Loading (on a Reconditioned, Strong Acid Cationic Exchanger
Packed in a 250 ml RFC Column, @ 100 ml/min)

↓

Flow Through (Nonadsorbed
Components Including Lactose,  ← Washing (with 0.05M Sodium Acetate at pH 3.8)
Minerals, Lactic Acid and Water)

↓

Immunoglobulin
& β-Lactoglobulin  ← Elution (with 0.1M Sodium Acetate + 0.5M NaCl at pH 4.0)

↓

Reconditioning (with 0.05 Na
Acetate at pH 4.0 to Reduce Conductivity)

↓

α-Lactalbumin  ← Elution (with 0.1M Sodium Acetate + 0.1M NaCl at pH 5.0)

↓

Reconditioning (with 0.05 Na Acetate at pH 5.0)

↓

Bovine Serum Albumin  ← Elution (with 0.05M Sodium Phosphate at pH 7.0)

↓

Lactoferrin  ← Elution (with 0.05M Sodium Phosphate + 0.5M NaCl at pH 7.5)

↓

Cleaning (with 0.2M NaOH + 1.0M NaCl, Followed by 20%
EtOH Solution)

↓

Re-equilibration (with 0.05M Na Acetate at pH 3.8)

↓

Repeat Sequence

ELUTION PATTERN OF WHEY PROTEINS SHOWING PEAK 4

SEQUENTIAL SEPARATION OF WHEY

This invention is a continuation-in-part of application Ser. No. 08/678,364, filed Jul. 16, 1996, now U.S. Pat. No. 5,756,680, which is a continuation of application Ser. No. 08/177,574, filed Jan. 5, 1994 now abandoned.

FIELD OF THE INVENTION

The present invention is related to the separation of whey proteins, particularly to the sequential separation of whey proteins into separate fractions through the use of chromatography.

BACKGROUND OF THE INVENTION

The dairy industry represents a major source of income for many people throughout the world, and dairy products represent a significant source of nutrition for a majority of the world's human and non-human animal populations in the form of milk, cheese, yogurt, and other products. In 1994, the U.S. dairy (and egg) industry contributed approximately $717,000,000 to U.S. exports. The import figure for these same commodities was $583,000,000 (R. Famighetti (ed.), *World Almanac and Book of Facts*, 1996 Funk & Wagnalls, Mahway, N.J., [1995], p. 207).

At least part of the dairy industry's success is due to the increased efficiency in milk production by various cattle breeds, as well as the increased efficiency of milk processing capabilities. Among the beneficiaries of this increased efficiency are the makers of cheese. The ancient art of cheese making represents a significant source of income for many areas, including the "dairy state" of Wisconsin, as well as many other locales. Although there are many variations, the primary steps in cheese making are shown in FIG. 1.

Cheese is made from the milk of various mammals, including cattle, sheep, goats, reindeer, and buffalo. Differences in the texture and tastes of cheeses produced from the milk of these animals are largely due to the differences in the milk compositions. Differences in these constituents also sometime contributes to the inability of animals of one species to utilize the nutrition available in the milk from other animal species. For example, some individuals are completely unable to tolerate cow's milk. These infants are often provided with goat's milk as a substitute formula.

The basic components of milk include fat, protein, lactose, ash, enzymes and vitamins. Table 1 lists the percent solids, and the percent solids comprised of fat, protein, and carbohydrates (R. W. Kirk and S. I. Bistner, *Handbook of Veterinary Procedures and Emergency Treatment*, 2d ed., W. B. Saunders Co., Philadelphia, Pa. [1975], pp. 644–649).

TABLE 1

Chemical Composition (%) of Milk

| Animal | % Solids | % Fat | % Protein | % Carbohydrates | % Ash |
|---|---|---|---|---|---|
| Cattle | 11.9 | 29.9 | 25.6 | 38.7 | 5.8 |
| Goats | 12.8 | 32.0 | 29.0 | 32.8 | 6.2 |
| Sheep | 20.5 | 41.9 | 27.9 | 26.3 | 3.9 |
| Swine | 20.0 | 36.6 | 33.0 | 24.8 | 5.6 |
| Horses | 10.9 | 14.4 | 20.2 | 56.6 | 8.8 |
| Rhesus Monkeys | 12.2 | 31.9 | 17.2 | 48.4 | 2.5 |

There are two major categories of milk proteins. The first is present as a suspension (colloid) known as "casein," while the second form referred to as "whey protein" is soluble. Other compounds present in the protein component of milk include peptones, non-proteinaceous nitrogenous compounds, and various enzymes. When milk is acidified (i.e., becomes sour) in the presence of coagulating enzymes, the casein is altered in such a manner that "curd" is formed. Curd is then used to make cheese. The liquid portion of the soured milk is the "whey." As shown in FIG. 1, whey is a by-product of the cheesemaking process. In the past, the whey was discarded as waste or used for livestock feed, although whey made by acid coagulation and high heat (e.g., during the making of cheddar, Swiss or provolone cheeses) may be used to make ricotta cheese (A. M. Pearl et al., *Completely Cheese: The Cheeselover's Companion*, Jonathan David Publishers, Inc., Middle Village, N.Y., [1978], p. 59–60). Other cheeses made principally from whey include such Scandinavian cheeses as Gjetost, made from goat's milk whey, and Mysost, made from cow's milk whey, as well as Sapsago, a cheese made in Switzerland from cow's milk whey. Nonetheless, in the past whey was primarily considered to be a waste product of cheesemaking.

In the cheese industry, two types of precipitation techniques are most commonly used to separate the total milk proteins separated into caseins and whey proteins—rennet precipitation and acid precipitation. In rennet precipitation, rennin is added to warm milk (30–35° C.), precipitating the caseins and leaving the whey proteins in solution. Whey produced by this method is referred to as "sweet whey." Acid precipitation is carried out at the isoelectric point of milk (i.e., 4.7) through the use of acid to precipitate out casein and leave the whey in solution. Whey produced by this method is referred to as "acid whey." The choice of the method used to make the curd depends on the desired cheese product.

Although the whey is discarded during the cheesemaking process, it has significant value as a source of nutrition. Unless whey is used to produce other products (including feed), it is a liability for cheese factories. The high biological oxygen demand (BOD) of whey presents disposal problems. Thus, large quantities of whey are used in candies and special cheese products. In addition, large quantities of dry and concentrated forms of whey are also used in dry and concentrated forms that are mixed with food and feeds. Whey may also be condensed and spray dried by the roller process for other uses. Various whey drinks have been developed, including wines, carbonated beverages, buttermilk substitutes, whey-fruit flavored drinks, and whey-tomato drinks. Whey is also used to produce whey butter, soups, protein hydrolysates, cheeses, processed cheese foods and spreads, bakery products, infant foods, geriatric foods, hydrolyzed lactose syrup, pills, riboflavin concentrates, alcohol (e.g., butyl alcohol), methane, acetone, spirit vinegar, food acidulant, resins, coatings, tanning, acrylic plastics, and biomass (See e.g., Frandsen (ed.), *Dairy Handbook and Dictionary*, J. H. Frandsen, Amherst, Mass. [1958], at pages 791–792; and Taylor, *Scientific Farm Animal Production* (5th ed.), Prentice Hall, Englewood Cliffs, N.J., [1995], p. 93). In their undenatured, soluble form, whey proteins are also useful as binders in extruded vegetable or animal protein foods (See e.g., Rosenthal, *Milk and Dairy Products*, VCH, New York, N.Y., [1991], at p. 137).

Whey contains various proteins (e.g., β-lactoglobulin and α-lactalbumin), lactose, soluble minerals, water-soluble vitamins, and enzymes. Protein compounds present in whey have received the most attention, for their potential utilization in various foods, feeds, and other products as mentioned above. Thus, separation of these compounds has been studied. The following table lists some of the properties and concentrations of these compounds.

TABLE 2

MOLECULAR WEIGHTS OF SELECTED WHEY PROTEINS

| Protein | Isoelectric Point | Molecular Weight | Approx. Concentration in Whey (g/l) |
|---|---|---|---|
| β-Lactoglobulin | 5.35–5.49 | 18,300 | 3.0 |
| α-Lactalbumin | 4.2–4.5 | 14,000 | 0.7 |
| Immunoglobulins | 5.5–8.3 | ≧150000 | 0.6 |
| Bovine Serum Albumin | 5.13 | 69,000 | 0.3 |
| Protease-Peptones | 3.3–3.7 | 4,100–40,800 | 1.4 |
| Lactoferrin | 7.8–8.0 | 77,000 | 0.03 |
| Lactoperoxidase | 9.2–9.9 | 77,500 | 0.02 |

Indeed, various methods are commercially available for the separation, removal, concentration, and/or purification of selected whey proteins, including the methods of such publications as: U.S. Pat. No. 5,077,067, which discloses a process for the selective and quantitative removal of lactoglobulins from whey proteins; U.S. Pat. No. 5,055,558, which describes a method for the selective extraction of β-lactoglobulin from whey or milk by subunit exchange chromatography; U.S. Pat. No. 4,791,193, which discloses a method for the preparation of pure lactoferrin from whey or skim milk; U.S. Pat. No. 4,668,771, which describes a method for the isolation and purification of bovine lactoferrin; U.S. Pat. No. 4,997,914 which describes an adsorption chromatography method for the separation and purification of lactoferrin; U.S. Pat. No. 4,820,348, which directed to a chromatographic method for the separation of lactose from milk; U.S. Pat. No. 4,446,164, which discloses milk-like compositions constituted from a sweet whey base with additives such as soluble proteins, edible vegetable oils, non-fat dry milk solids, sugar or synthetic sweeteners; U.S. Pat. No. 5,085,881, which describes a process for separating fractions from dried milk or milk products for use as food stuffs or food or pharmaceutical adjuvants; U.S. Pat. No. 5,093,143, which discloses nutrient compositions that simulate milk and are rich in energy and calcium content but poor in albumin and phosphorus; U.S. Patent No. 4,202,909, which describes a process for the treatment of whey to produce pure lactose and salt products; U.S. Pat. No. 5,008,376, which discloses a process for producing a whey fraction with a high concentration of α-lactalbumin by ultrafiltration technology, and U.S. Pat. No. 3,969,337, which discloses a method for the chromatographic fractionation of whey. However, all of these methods have significant disadvantages, including the fact that all result in the destruction or disposal of all but one selected protein from the whey, thereby wasting the other valuable proteins obtained during the separation process.

Furthermore, the cheese industry produces large amounts of whey, much of which is used to make whey protein concentrate (WPC). WPC is mainly produced by the thermocalcic pretreatment, ultrafiltration (UF) and microfiltration (MF) of whey. However, WPC has some undesirable properties, such as low foam formation, and poor foam stability due to its high lactose and lipid content (Karleskind, et. al. 1995). These undesirable properties are mainly eliminated for whey protein isolate (WPI), which is made by adsorption of proteins directly from whey onto ion-exchange beads. In commercial WPI manufacturing, whey proteins are adsorbed into ion-exchange beads, followed by washing, elution of the adsorbed protein, cleaning, and regeneration of the beads. The rate of WPI production or fractionation of whey proteins using conventional ion-exchange beads are slow (See, Wit, et al. 1995, Uchida et al. 1993, and de Rahm el al. 1989).

Commercial-scale fractionation of different whey proteins has been hampered by the lack of an economical fractionation technology. The resolution and throughput of conventional chromatographic methods such as stirred tanks and packed axial columns is too low to be economical. This is especially true because the whey proteins are present in small quantities. Thus, in order to recover a fixed amount of protein, large volumes of solution must be processed.

In addition, conventional ion-exchange beads have limitations. For example, the equilibrium rate is slow in large ion-exchange beads due to the lengthy times required for diffusion of the proteins into the beads. Smaller ion-exchange beads decrease the diffusion time, but this causes an increase in the liquid drainage time through the bed. Consequently, the throughput of ion-exchange process is limited by either slow intra-bead diffusion for large beads or slow liquid drainage rate and high column pressure drops (i.e., in packed bed columns) for small beads.

Several regenerated cellulose ion-exchange beads are also available for whey protein isolation. However, these cellulosic ion exchange beads suffer from the disadvantages of low protein capacity and high price. These two factors have greatly hindered the commercial application of these beads for use with whey (Ayers and Petersen, 1985).

None of these methods achieve the separation of various proteins from whey in a single process step. It would be desirable, therefore, to provide a method for the continuous and sequential separation of various proteins from whey in a simple one or two step separation process. Furthermore, none of these methods provide a product which can be easily, economically, and efficiently utilized as a supplement for infant formulas, fat substitutes or other commercially important products.

The cost of producing WPI is higher than WPC, primarily due to higher capital costs for building the ion-exchange plant compared to the UF and MF plant (Etzel, 1995). In order to market WPI at an economically reasonable lower cost, either the process efficiency and throughput must be increased or the capital cost must be decreased. Thus, a need remains in the industry for economical methods to process whey products, including processes and methods that are designed so as to permit reutilization of buffers and constituents utilized during the purification of whey compounds. In addition, methods are needed to increase the efficiency of whey processing procedures, including methods designed to reduce the time necessary to obtain a final product.

SUMMARY OF THE INVENTION

The present invention addresses the previously unmet needs in the art, as briefly described above. The present invention provides a process for the sequential separation of at least five different proteins from whey and incorporating these separated whey proteins into pharmaceutical and food formulations. The process of the invention is directed to the continuous, sequential separation of whey proteins by chromatography, comprising adsorbing the proteins in liquid whey on a suitable separation medium packed in a chromatographic column and sequentially eluting immunoglobulin (e.g, IgG), β-lactoglobulin (β-Lg), α-lactalbumin (α-La), bovine serum albumin (BSA), and lactoferrin (L-Fe) fractions with buffers at suitable pH and ionic strength. Even though both axial and radial flow chromatography may be utilized, a horizontal flow column is particularly suitable for the process of this invention. Various chromatography media are also contemplated for use in the present invention.

The present invention provides methods for the continuous sequential separation of whey proteins by chromatography. In some embodiments, the methods comprise adsorbing liquid whey on a separation medium packed in a chromatographic column, and sequentially eluting immunoglobulin, β-lactoglobin, α-lactalbumin, bovine serum albumin, and lactoferrin fractions. In preferred embodiments, the liquid whey is selected from the group consisting of pasteurized sweet whey, pasteurized acid whey, non-pasteurized acid whey, and whey protein concentrate. In some particularly preferred embodiments, the separation medium is a cationic resin. In alternative embodiments, the sequentially eluted immunoglobulin, β-lactoglobin, α-lactalbumin, bovine serum albumin, and lactoferrin fractions are collected and concentrated by ultrafiltration. In yet other embodiments, the concentrated immunoglobulin, β-lactoglobin, α-lactalbumin, bovine serum albumin, and lactoferrin fractions are further purified by diafiltration.

The present invention also provides methods for the sequential separation of whey proteins, comprising the steps of: packing a chromatographic column with a cationic exchange resin to provide a packed chromatographic column; equilibrating the packed chromatographic column with an acetate buffer (in some preferred embodiments, the buffer pH is about 3.8); providing a whey sample (in some preferred embodiments, the whey sample buffer has a pH of about 3.8); passing the whey sample through the packed chromatographic column, under conditions such that the whey proteins adsorb to the packed chromatographic column; collecting the flow-through from the packed chromatographic column, wherein the flow-through comprises lactose, minerals, lactic acid, and non-nitrogenous components; in some embodiments, this step is followed by a washing step (i.e., the packed chromatographic column is washed with buffer or water); sequentially eluting immunoglobulin and β-lactoglobin from the packed chromatographic column with a buffer (in some preferred embodiments, the buffer comprises sodium acetate and sodium chloride, while in particularly preferred embodiments the buffer has a pH of about 4.0; in some preferred embodiments, the packed chromatographic column is then reconditioned prior to conducting the next steps; eluting α-lactalbumin from the packed chromatographic column with a buffer (in some preferred embodiments, the buffer comprises acetate and sodium chloride, while in particularly preferred embodiments, the buffer has a pH of about 5.0); in some embodiments, the column is again reconditioned prior to conducting the next steps; eluting bovine serum albumin from the packed chromatographic column with a buffer (in some embodiments, the buffer comprises phosphate, while in some preferred embodiments, the buffer has a pH of about 7.0); and eluting lactoferrin from the d packed chromatographic column with a buffer, (in some preferred embodiments, the buffer comprises sodium phosphate and sodium chloride, while in particularly preferred embodiments the buffer has a pH of about 7.5). However, it is not intended that this or any other embodiments of the present invention be limited to any particular buffer composition and/or pH. Rather, it is intended that that present invention encompass buffers with properties such that they are capable of functioning as intended (i.e., elution of a whey component, such as lactoferrin, α-lactalbumin, β-lactoglobulin, etc.).

In some embodiments of the method, the whey is selected from the group consisting of pasteurized sweet whey, pasteurized acid whey, non-pasteurized acid whey, and whey protein concentrate. In particularly preferred embodiments, the chromatographic column is a radial flow column.

The present invention also provides methods for the separation of β-lactoglobulin from whey proteins, comprising the steps of packing a chromatographic column with an anionic exchange resin to provide a first packed chromatographic column; equilibrating the first packed chromatographic column (in preferred embodiments, a phosphate buffer is used; in particularly preferred embodiments, the buffer has a pH of about 7.5); providing a whey sample (in particularly preferred embodiments, the whey sample has a pH of about 8.0); passing the whey sample through the first packed chromatographic column under conditions wherein β-lactoglobulin adsorbs to the first packed chromatographic column; collecting the flow-through from the first packed chromatographic column, wherein the flow-through comprises α-lactalbumin, immunoglobulin(s), bovine serum albumin and lactoferrin suitable for further processing; and eluting the adsorbed β-lactoglobulin from the first packed chromatographic column (in some preferred embodiments, the elution is conducted with a buffer at a pH of about 7.5, while in particularly preferred embodiments, the buffer comprises containing sodium phosphate and sodium chloride), to produce an eluate.

In particularly preferred embodiments of the method, the first packed chromatographic column is a radial flow column. In yet other preferred embodiments, the method further comprises the steps of packing a second chromatographic column with an cationic exchange resin to provide a second packed chromatographic column; if needed, equilibrating the second packed chromatographic column; passing the flow-through through ultrafiltration membrane to produce an ultrafiltrate (in particularly preferred embodiments, the ultrafiltration membrane has a 10,000 molecular weight cut-off); adjusting the pH of the ultrafiltrate (in particularly preferred embodiments, the pH is adjusted to about 3.8); passing the ultrafiltrate through the second packed chromatographic column, under conditions such that immunoglobulin(s), α-lactalbumin, bovine serum albumin, and lactoferrin adsorb to the second packed chromatographic column; eluting the immunoglobulin(s) from the second packed chromatographic column with a buffer (in some preferred embodiments, the buffer comprises sodium acetate and sodium chloride, while in other preferred embodiments, the buffer has a pH of about 4.0); reconditioning the second packed chromatographic column, if needed; eluting the α-lactalbumin from the second packed chromatographic column with a buffer (in preferred embodiments, the buffer comprises sodium acetate and sodium chloride, while in particularly preferred embodiments, the buffer has a pH of about 5.0); reconditioning the second packed chromatographic column, if needed; eluting the bovine serum albumin from the second packed chromatographic column with a buffer (in some preferred embodiments, the buffer comprises phosphate, while in particularly preferred embodiments, the buffer has a pH of about 7.0); and eluting the lactoferrin from the second packed chromatographic column with a buffer (in some preferred embodiments, the buffer comprises sodium phosphate and sodium chloride, while in particularly preferred embodiments, the buffer has a pH of about 7.5). In yet further particularly preferred embodiments, the second packed chromatographic column is radial flow column.

In yet other embodiments, the flow-through comprises an infant formula. In still other embodiments, infant formula contains at least 25% lactoferrin and less than one half of a percent of β-lactoglobulin. In alternative embodiments, the infant formula comprises about 43.5% β-lactalbumin, about 31.6% lactoferrin, about 15.4% immunoglobulin, and about 9.5% bovine serum albumin. In additional embodiments, the infant formula further comprises casein hydrolysate, fat, nonfat milk solids, carbohydrate, minerals, and vitamins.

In still other embodiments, the flow-through is combined with the eluate to produce a fat substitute. In some preferred embodiments, the fat substitute comprises about 60% β-lactoglobulin and 40% α-lactalbumin.

The present invention also provides methods for the sequential separation of whey proteins, comprising the steps of: a) providing a cationic exchange resin contained within a container; a whey sample, wherein the whey sample comprises at least one whey protein selected from the group consisting of immunoglobulin, β-lactoglobulin, α-lactalbumin, lactoperoxidase, serum albumin, and lactoferrin; and a cationic exchange resin; b) passing the whey sample through the packed resin under conditions whereby the whey proteins adsorb to the resin; c) collecting the flow-through from the cationic exchange resin, wherein the flow-through comprises lactose, minerals, lactic acid, and non-nitrogenous components; d) sequentially eluting the immunoglobulin and the β-lactoglobulin from the cationic exchange resin; e) eluting the α-lactalbumin from cationic exchange resin; f) eluting the serum albumin from cationic exchange resin; g) eluting the lactoferrin from the cationic exchange resin; and h) eluting the lactoperoxidase from the cationic exchange resin.

In some embodiments of the methods, the whey is selected from the group consisting of pasteurized sweet whey, pasteurized acid whey, non-pasteurized acid whey, and whey protein concentrate. In some preferred embodiments of the method, the container comprises a radial flow column, while in other preferred embodiments the container comprises an axial flow column. In yet other embodiments of the methods, the container is selected from the group consisting of beakers, tanks, vats, and chambers. In alternative preferred embodiments, the resin comprises a cellulosic matrix. In other preferred embodiments, the cationic exchange resin comprises cross-linked flexible sponge absorbent. In yet other preferred embodiments, the cross-linked flexible sponge absorbent comprises substantially uniformly distributed fibrous reinforcement. In still other embodiments, the cationic exchange resin is selected from the group consisting of co-polymerized glycidyl methacrylate, and cross-linked diethylene glycol. In still other embodiments, steps e), f), g) h), and i) utilize a buffer. In some preferred embodiments, the buffer is selected from the group consisting of whey buffer, permeate, and modified whey buffer. In yet other preferred embodiments, the buffer is recycled.

The present invention also provides two-column methods for the separation of whey proteins comprising the steps of: a) providing anionic exchange resin present within a first container to produce a first resin; a whey sample containing β-lactoglobulin, immunoglobulins, α-lactalbumin, serum albumin, and lactoferrin, and a soluble portion; cationic exchange resin present within a second container to produce a second resin; and an ultrafiltration membrane; b) passing the whey sample through the first resin under conditions wherein the β-lactoglobulin adsorbs to the first resin and the soluble portion pass through the column to form a flow-through; c) collecting the flow-through from the first resin, wherein the flow-through comprises α-lactalbumin, immunoglobulins, serum albumin and lactoferrin suitable for further processing; d) eluting the adsorbed β-lactoglobulin from the first resin to produce an eluate; e) passing the flow-through collected in step c) through the ultrafiltration membrane to produce an ultrafiltrate; f) passing the ultrafiltrate through the second resin, under conditions such that immunoglobulins, α-lactalbumin, serum albumin, and lactoferrin adsorb to the second resin; g) eluting the immunoglobulins from the second resin; h) eluting the α-lactalbumin from the second resin; i) eluting the serum albumin from the second resin; and j) eluting the lactoferrin from the second resin.

The present invention also provides α-lactalbumin prepared according to the two-column methods described above. In addition, the present invention provides compositions comprising α-lactalbumin prepared according to the two-column methods wherein the composition is an emulsifier, as well as compositions comprising α-lactalbumin prepared according to the two-column methods, wherein the composition is a foaming agent.

The present invention further provides immunoglobulins prepared according to the two-column methods described above. In addition, the present invention provides compositions comprising immunoglobulins prepared according to the two-column methods wherein the composition is an immune supplement. The present invention also provides serum albumin prepared according to the two-column methods. In addition, the present invention provides compositions comprising serum albumin prepared according to the two-column methods, wherein the composition is a creaming agent.

The present invention also provides lactoferrin prepared according to the two-column methods described above. In addition, the present invention provides β-lactoglobulin prepared according to the two-column methods described above. The present invention also provides compositions comprising β-lactoglobulin prepared according to the two-column methods, wherein the composition is a gel.

In some embodiments of the two-column method, the first resin is reconditioned, while in other embodiments, the second resin is reconditioned, and in yet other embodiments, both the first and second resins are reconditioned.

In alternative embodiments, the first and/or second containers are selected from the group consisting of radial flow chromatography columns, axial flow chromatography columns, beakers, vats, tanks, and chambers. In yet other embodiments of the method, the first and/or second resins are cleaned with a buffer. In yet other embodiments, the cleaning a buffer comprises sodium hydroxide, sodium chloride and ethanol.

In yet other embodiments of the methods, the flow through comprises a formula comprising at least one whey protein. In still other embodiments, the method further comprises the step of diafiltering the formula. In some preferred embodiments, the formula comprises a nutritional formula selected from the group consisting of sport drinks, fruit gels, ice cream, and cookies. In yet other embodiments, the formula comprises an infant food, in particularly preferred embodiments of the infant food, the food is non-allergenic. In alternative embodiments, the formula is freeze dried, while in still other embodiments, the formula is frozen, and in other embodiments, the formula is spray dried.

The present invention also provides methods for processing whey comprising the steps of: a) providing a cation exchange resin; and a whey sample, wherein the whey sample comprises whey proteins; b) passing the whey sample through the cation exchange resin under conditions whereby the whey proteins adsorb to the cation exchange resin, and a flow through passes through the cation exchange resin; c) collecting the flow-through, wherein the flow-through comprises deproteinized whey. In some embodiments, the methods further comprise use of an anion exchange resin.

In alternative embodiments, the methods comprise the further steps of: d) passing the deproteinized whey through the anion exchange resin under conditions such that any whey proteins present in the deproteinized whey adsorb to the anion exchange resin; and e) eluting the remaining whey proteins from the anion exchange resin. In yet other embodiments, the methods further comprise the step of f) washing the whey proteins to produce clear whey protein isolate. The present invention also provides whey protein isolate prepared according to these methods. The present invention also provides deproteinized whey prepared according to these methods.

In still other embodiments of the methods, the cation exchange resin comprises a chromatography column selected from the group consisting of radial flow columns and axial flow columns. In yet other embodiments, the anion exchange resin comprises a chromatography column selected from the group consisting of radial flow columns and axial flow columns. In other embodiments, the whey proteins adsorbed to the cation exchange resin are eluted from the cation exchange resin. In yet other embodiments, the cation exchange resin is washed following step b) to produce a wash buffer. In some preferred embodiments, the wash buffer comprises non-protein nitrogen. In yet other preferred embodiments, the wash buffer further comprises lactose, minerals, lactic acid, and vitamins. In still other embodiments of the method, the cation exchange resin is a weak acid cation exchange resin. In particularly preferred embodiments, the weak acid cation exchange resin is "CM-SEPRASORB" resin. In other preferred embodiments, the anion exchange resin is a weak base anion exchange resin. In yet other particularly preferred embodiments, the weak base anion exchange resin is "DE-SEPRASORB" resin. In still other embodiments, the methods further comprise the step of f) reconditioning the cation and/or anion exchange resins with a buffer. In some preferred embodiments, the buffer used to recondition the resins comprises deproteinized whey.

The present invention also provides methods for the production of clear whey protein isolate comprising: a) providing a cation exchange resin; and a whey sample, wherein the whey sample comprises serum albumin, lipoprotein, whey protein, and a soluble portion; b) passing the whey sample through the cation exchange resin, under conditions that the whey protein, bovine serum albumin, and lipoprotein adsorbs to the cation exchange resin, and the soluble portion flows through the cation exchange resin to produce a flow-through; c) eluting the whey protein adsorbed to the cation exchange resin to provide clear whey protein isolate; and d) eluting the serum albumin and fat from the cation exchange resin. In preferred embodiments, the clear whey protein isolate comprisese α-lactalbumin, β-lactoglobulin, and immunoglobulin. The present invention further provides clear whey protein isolated prepared according to the method described.

In some embodiments, the elution ot the whey protein adsorbed to the packed cation exchange resin is accomplished using a clear whey protein isolate elution buffer. In yet other embodiments, the clear whey protein isolate elution buffer comprises sodium acetate and sodium chloride. In still other embodiments, the elution of serum albumin and lipoprotein is accomplished using serum albumin buffer. In particularly preferred embodiments, the serum albumin buffer comprises sodium chloride, and a salt selected from the group consisting of sodium acetate, and citrate. In still other preferred embodiments, the whey protein isolate elution buffer is recycled, while in further embodiments, the whey protein isolate elution buffer comprises the flow-through. In alternative embodiments, the serum albumin buffer is recycled. In other embodiments, the whey protein isolate elution buffer comprises deproteinized whey. In some preferred embodiments, the deproteinized whey is recycled, while in other embodiments, the clear whey protein isolate elution buffer is whey buffer.

In further embodiments, the method comprises the further steps of: e) ultrafiltering the clear whey protein isolated obtained in step b) to produce an ultrafiltrate; and f) diafiltering the ultrafiltrate to produce a diafiltered ultrafiltrate. In other embodiments, the methods further comprise the step of spray drying the diafiltered ultrafiltrate to produce clear whey protein isolate powder.

The present invention also provides methods for the production of α-lactalbumin-enriched whey protein isolate comprising: a) providing an anion exchange resin; and whey comprising α-lactalbumin and β-lactoglobulin; and b) passing the whey through the anion exchange resin under conditions such that the β-lactoglobulin binds to the anion exchange resin and the α-lactalbumin flows through the anion exchange resin, to produce whey enriched in α-lactalbumin. In some embodiments, the methods further comprise the step of c) eluting the α-lactoglobulin from the anion exchange resin. The present invention also provides α-lactalbumin produced according to these methods. The present invention further provides compositions comprising α-lactalbumin prepared according to these methods, wherein the composition is an emulsifier, as well as compositions comprising α-lactalbumin prepared according to these methods, wherein the composition is a foaming agent. The present invention also provides compositions comprising α-lactalbumin prepared according to these methods, wherein the composition is non-allergenic. The present invention further provides β-lactoglobulin produced according to these methods, while in some preferred embodiments, the present inventoin provides compositions comprising β-lactoglobulin prepared according to these methods, wherein the composition is a gel.

The present invention also provides methods cleaning resin contained within a chromatography column, comprising the steps of: a) providing resin contained within a container; sodium hypochlorite; sodium hydroxide; hydrochloric acid; and v) ethanol; b) washing the resin with the sodium hypochlorite to produce washed resin; c) exposing the washed resin to the sodium hydroxide to produce a base-treated resin; d) exposing the base-treated resin to the hydrochloric acid to produce an acid-treated resin; and e) exposing the acid-treated resin with the ethanol to produce a cleaned resin.

In some embodiments, the method further comprises step f) equilibrating the cleaned resin. In still other embodiments of the methods, the washed resin is rinsed with water prior to washing with the sodium hypochlorite. In yet other embodiments, the base-treated resin is rinsed with water prior to exposing to the hydrochloric acid. In still other embodiments, the acid-treated resin is rinsed with water prior to exposure to ethanol. In yet other embodiments, the methods comprise the further step of passing the whey enriched in α-lactalbumin through a cation exchange resin. In yet other embodiments, the present invention provides compositions comprising clear whey protein isolate.

It is contemplated that the whey products separated by the method of the present invention will be useful as nutritional or other supplements, feed constituents, and/or fillers, as well as part of new food products. For example, it is contemplated that the whey products of the present invention will be used in various products, including, but not limited to beverages, confectionery items (e.g., candies), convenience foods, desserts, baked goods, sauces, infant food and formulae, geriatric foods, animal feeds, and as drug constituents.

BRIEF DESCRIPTION OF THE DRAWINGS

FIG. 2 is flow chart showing the elution steps of one method for the sequential separation of whey proteins.

DESCRIPTION OF THE INVENTION

Figure 1:
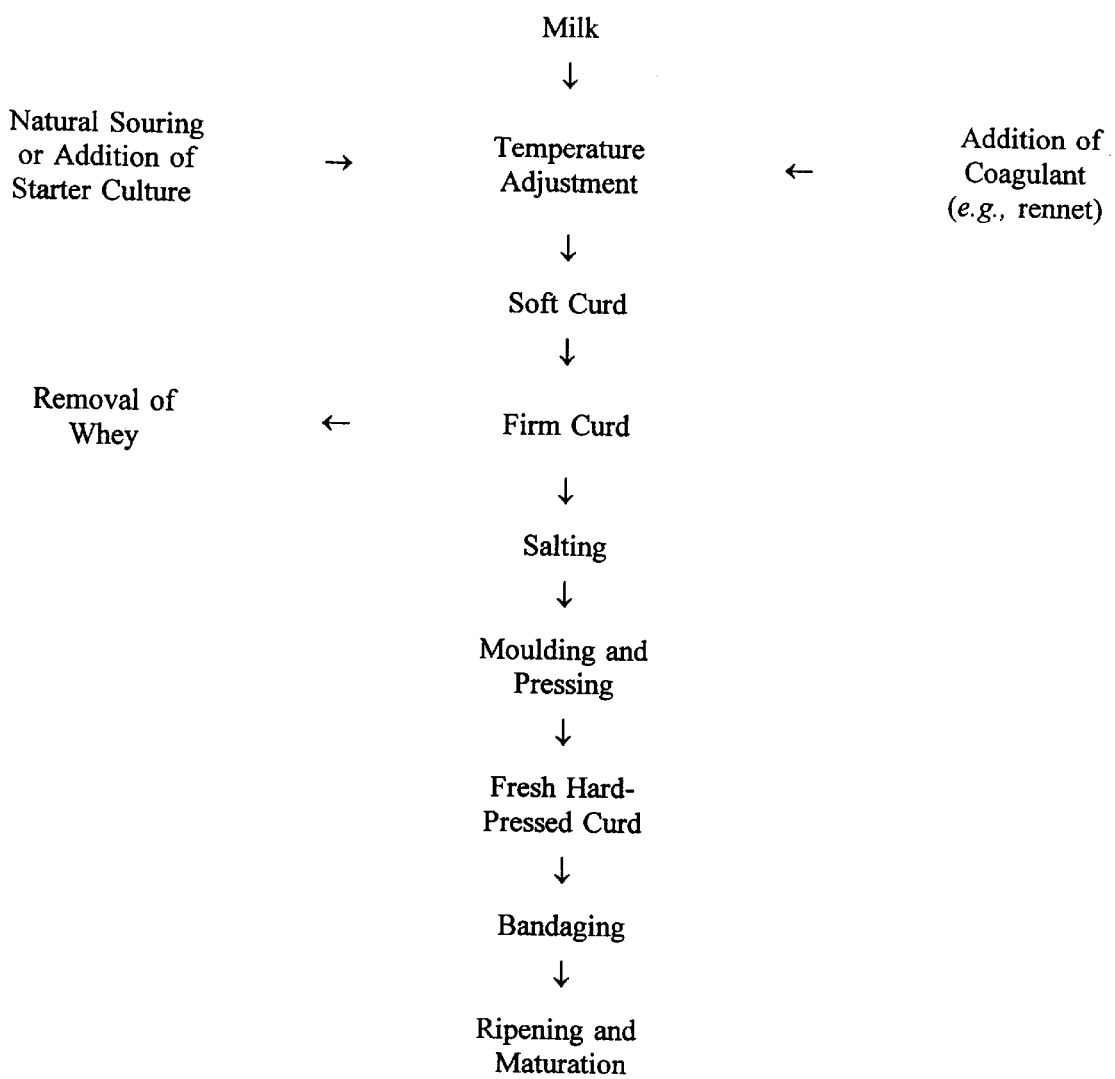
FIG. 1 is a flow chart showing the basic steps in the cheese making process.

Monolithic ion-exchange media, such as those described in U.S. Pat. No. 5,492,723, herein incorporated by reference) represent new technology designed to overcome the limitations encountered in commercial ion-exchange processes.

In various embodiments of the present invention, monolithic ion-exchange media were used to separate whey proteins. In one embodiment of the present invention, whey is passed through the micron-sized pores of the media in a manner such that the proteins adsorbed onto the ion-exchange groups on the media surface. Diffusion limitation is negligible because the whey flows by convection through the fine pores of the media. Therefore, this ion-exchange media process greatly increases efficiency and throughput compared to the existing (i.e., conventional) ion-exchange processes. These factors may make the production costs and ultimate price of WPI much lower than other methods. Indeed, one object of the present invention is to provide highly economical methods for production of WPI and fractionation of whey proteins. In particularly preferred embodiments, monolithic ion-exchange media are used in the methods of the present invention.

Development of the present invention involved multiple steps. First, carboxymethyl weak-acid cation exchange ("CM-SEPRASORB"; Sepragen) or diethylaminoethyl weak-base anion exchange "DERE-SEPRASORB"; Sepragen) media were used to isolate whey proteins. Indeed, the feasibility of using monolithic ion-exchange media for WPI production, and fractionation of α-lactalbumin and β-lactoglobulin from whey was investigated. Monolithic "SEPRASORB" sponge-type ion-exchange media was prepared from regenerated cellulose (Sanderson et. al. U.S. Pat. No. 5,492,723; herein incorporated by reference) in the form of sheets. The cross-linked, flexible, sponge-like regenerated cellulose ion-exchange medium was prepared by mixing cellulose with sodium hydroxide and water to produce viscose. Sodium sulfate, calcium carbonate, and cotton linters were added to this viscose. The resulting mixture was then blended to produce a paste. This paste was then molded between two plates of perforated stainless steel and regenerated in sodium sulfate solution.

The regenerated cellulose was then treated with cross-linking agents such as formaldehyde, dichlorohydrin, epichlorhydrin, dibromohydrin, epichlorhydrin, dibromomethane, bis-epoxypropyl ether, 1,4-butane diol-bis-epoxy ether, glycol, and divinylsulfone, to form cross-linked cellulose. The cross-linked cellulose was further treated with sodium hydroxide solution to solublize parts of the sponge which were not cross-linked, and thereby open up the sponge structure. The cross-linked cellulose may be treated with reagents which introduce ion-exchange groups to the material. Examples of compounds include, but are not limited to compounds which contain amino, alkyl amino, or quaternary ammonium groups (i.e., when it is desired to produce an anion exchange resin), or compounds containing sulfo, phospho, or carboxyl groups (i.e., when it is desired to produce at cation exchange resin).

A sample of a starting material selected from pasteurized sweet whey, pasteurized acid whey, non-pasteurized acid or sweet whey obtained as a by-product of cheese manufacture, or whey protein concentrate, prepared from the pasteurized or non-pasteurized whey by techniques such as reverse osmosis (RO) or ultrafiltration (UF) was loaded on to a chromatographic column, preferably a horizontal flow chromatographic column, packed with either an acidic or basic, cationic or anionic resin material such as "MACRO-PREP" high S or Q (Bio-Rad). Although not necessarily required, if needed or desired, the whey, concentrated whey, or whey protein concentrate may be subjected to pretreatment procedures such as de-ashing through electrodialysis or ion exchange, clarification to remove casein fines, and/or micro-filtration for separating colloidal and suspended particles (e.g., fat residues).

The present invention provides methods and compositions for the efficient and effective processing of whey. The present invention also provides methods for the efficient and effective isolation of whey proteins. These proteins are suitable for numerous applications (e.g., food and drink products and supplements, as well as feeds).

Isolation of Lactoferrin and Lactoperoxidase from Whey

The present invention also provides methods for the isolation of two important milk proteins. These proteins, lactoferrin and lactoperoxidase are two of the three important proteins present in human milk with non-specific antibacterial activity.

Lactoferrin is an 80 kDa iron-binding glycoprotein that is present in significantly large amounts in human milk (approximately 2.0 g/L), as compared to bovine milk (approximately 0.1 g/L). Due to its iron-binding properties, it has been proposed that lactoferrin plays a role in the uptake of iron from the intestinal mucosa, and acts as a bacteriostatic agent by withholding iron from iron-requiring bacteria. In addition, its presence in neutrophils and release during inflammation, suggests that lactoferrin is also involved in phagocytic killing and the immune response. Additionally, lactoferrin may function in other ways unrelated to iron-binding (e.g., as a growth factor and/or bacteriostatic agent).

Lactoperoxidase catalyzes the conversion of peroxide ($H_2O_2$) to water. In the presence of thiocyanate, lactoperoxidase forms an enzyme-$H_2O_2$ complex, a bactericidal compound capable of destroying Gram-negative bacteria. This system may be used to improve the shelf-life of raw milk. During infections and other disturbances of the synthetic activity of the mammary gland, the increased antibacterial defense system is reflected in the concentration of lactoperoxidase in milk.

The present invention provides simplified methods for the isolation of lactoperoxidase and lactoferrin from whey in high concentrations.

Production of α-Lactalbumin-Enriched Whey (WPC) and β-Lactoglobulin From Whey

The present invention also provides methods to remove β-lactoglobulin from bovine whey and prepare whey (WPC) enriched with α-lactalbumin.

Alpha lactalbumin is a major protein of human milk, making up 10–20% of the total protein. α-lactalbumin has been shown to be a component of lactose synthase, the enzyme responsible for lactose synthesis in the mammary gland. α-lactalbumin has very high nutritional value, and its amino acid composition appears to be very similar to the estimated amino acid requirement of newborns (See e.g., Lonnerdal and Atkinson, in Jensen (ed.), *Handbook of Milk Composition*, Academic Press, N.Y., [1995], at pp. 358–360). Thus, it may be desirable to include higher levels of α-lactalbumin in milk-based infant formulas, in order to provide a formula with an amino acid profile that similar to that received by breast-fed infants. Bovine milk contains a significantly lower amount of α-lactalbumin (1.2 g/L) than human milk (2.8 g/l), while human milk contains a negligible amount of β-lactoglobulin compared to bovine milk (3.2 g/L). The methods of the present invention address these differences in milk compositions by providing means to increase the α-lactalbumin content and decrease the β-lactoglobulin content of bovine milk used in infant formula.

Separation of Cloudy and Clear Whey Protein Isolates (WPI)

The fat residue remaining in whey after clarification and centrifugation is primarily composed of glycerides and phospholipids. This fat residue is the major component contributing to the cloudy appearance of whey and whey products. In the processes used to produce whey protein concentrate (WPC) or WPI from whey, lipids are totally or partially separated from the protein portion. Thus, depending upon the concentration level, a wide range of fat content can be expected in dehydrated whey protein compositions. For example, WPC 35 (i.e., WPC containing 35% total protein on a dry basis), may contain 2–3% total fat, while WPC 80 may contain 7–8% total fat, and WPI may contain 0.5–1.0% total fat, depending upon the fat and protein concentration in the finished product.

In addition to the cloudy appearance of formulations containing whey or whey proteins, fat also contributes a dairy note and flavor to the formulation. Although the cloudiness property due to the presence of fat associated with whey and whey proteins may be desirable in some food applications, in other applications it is a limitation to its use. The present invention provides the means to expand the utilization of WPI in areas beyond conventional applications such as clear or flavor-sensitive beverages, health or nutritional foods and feeds by providing a clear (<0.4% fat on a dry basis) WPI, along with cloudy WPI ($\geq$0.5% fat on a dry basis).

Recycling of Buffers

In addition to the methods described above, the present invention provides methods that permit the recycling of buffers during the processing steps. As the average dairy processor usually deals with over two million liters of whey per day, implementation of chromatographic methods in the dairy industry involves adaptation of the processes to the large volume processes and associated reagent costs. The recycling of whey by-products and/or buffers provides a means to reduce the process and chemical costs, and reduce the volume of buffer needed. As described in the Examples below, the buffering capacity of whey (i.e., due to minerals, ions, etc.), for equilibration of packed resin beds or elution of bound proteins, after either minor conductivity and/or pH adjustments, was determined. The Examples below show that whey by-products can be recycled to produce equilibration and elution buffers. As these buffers were obtained from the recycled whey by-products, the process is highly economical. In addition, buffers used to elute α-lactalbumin and β-lactoglobulin fractions from columns can be recycled, providing an option to dairy processors that is highly economical and addresses environmental issues. Thus, the present invention provides methods for recycling of elution and regeneration buffers (after minor conductivity and/or pH adjustments, as needed).

Cleaning in Place

In addition to the efficiencies provided by methods that allow the recycling of buffers, the present invention provides efficient and effective methods to clean chromatography columns. In the food and dairy industries, sanitation is of prime importance. Thus, a method that uses cleaning solutions that are acceptable to the industry and regulators, effective and readily available at the plant was considered to be important. Currently, caustic, acid, and sodium hypochlorite solutions are commonly used in the dairy industry for the cleaning and sanitation of equipment. As it is crucial that the chromatographic resin be clean and regenerated before beginning a new production cycle, a method for the regeneration of the resin packaged within the column (e.g., the RFC column of one embodiment of the present invention), was developed that improves the sanitation process, while extending the life of the resin.

Definitions

As used herein, the term "whey" is used in reference to the liquid portion of curdled milk. It is not intended that the term be limited to any particular type of whey (e.g., sweet whey or acid whey), nor is it intended that the term be limited to any particular type of milk (e.g., cow milk, sheep milk, goat milk, etc.). It is also not intended that the term be limited to any particular constituents or milk of a particular milkfat content. In addition, it is intended that the term exclude deproteinized whey or whey that has been significantly modified in any manner.

As used herein, the term "modified whey" refers to whey that has been modified such that it has properties that are different from whey. For example, the term encompasses deproteinized whey, as well as other wheys that have been treated or processes such that they are significantly different from naturally occurring whey.

As used herein, the term "whey buffer" refers to clear solutions (i.e., solutions with no or minimal detectable turbidity) with buffering capacity that are obtained when deproteinized whey is passed through a chromatography column (i.e., the effluent). In particularly preferred embodiments, the whey buffer is produced when deproteinized whey is passed through a charcoal chromatography column.

As used herein, the term "WPI" refers to whey protein isolate, and the term "WPC" refers to whey protein concentrate. In many embodiments, WPI is used in reference to a dehydrated product that contains at least 90% of its solids as total proteins (based on TKN analysis), while maintaining the original relative ratio between $\alpha$-lactalbumin and $\beta$-lactoglobulin (i.e., the two major proteins in whey). WPI may be prepared by either chromatographical methods (e.g., ion exchange) followed by ultrafiltration, or microfiltration followed by ultrafiltration. When chromatographic methods are used, two visually distinguishable WPI products may result. The first product is referred to herein as "clear WPI," while the second is "cloudy WPI." As discussed herein, the clear and cloudy characteristics are desirable properties for particular applications. Both clear WPI and cloudy WPI contain the two major whey proteins (i.e., $\alpha$-lactalbumin and $\beta$-lactoglobulin) at the same ratios, in reference to the original whey load (or "feed") used in the chromatographic method. However, cloudy and clear whey have slightly different profiles in terms of whey protein components.

WPI contains all of the major whey proteins and a fair portion (e.g., approximately 50%) of the residual milk fat fractions that were present in the whey prior to processing to produce WPI. Because of these lipid residues, the visual appearance of the separated liquid WPI is cloudy, similar to that of the original whey solution, but somewhat less intensely cloudy than the starting material. The amount of cloudiness depends upon the amount of fat remaining in the WPI.

Clear WPI has the same protein composition as WPI, but lacks most of the serum albumin (e.g., BSA), lipoprotein, and fat residues. By separating these components which produce the cloudiness observed in regular whey, the finished clear WPI product appears clear. While it is not necessary to understand the mechanisms involved in order to practice the present invention, the use of an appropriate elution for the production of clear WPI is important. Processing the whey at a temperature above the melting point of fat (e.g., 95–115° F.) will facilitate easier removal of fat in deproteinized whey.

WPI fraction samples with different clarities generated by bench processes (e.g., 100 ml RFC column) and following the steps given in the Examples below for producing both clear and cloudy WPI were tested in order to provide reference numbers for clarity values.

"Condensed whey" refers to a product made by concentrating whey in a vacuum pan. This product is high in milk sugar, protein, and riboflavin, making it nutritionally important. The major use of condensed whey is in cooking. "Dried whey" refers to whey from which most of the moisture has been removed. Dried whey is often provided in powdered form or pressed into bricks.

"Microfiltered whey" refers to whey that has undergone microfiltration. In particularly preferred embodiments, the membranes used for microfiltration have pore sizes in the range of approximately 0.1 to 10 $\mu$m. "Ultrafiltered whey" refers to whey that has been ultrafiltered. In particularly preferred embodiments, the ultrafiltration membranes of 10–30,000 are used.

As used herein, the term "sequential separation" refers to a process in which components present in a mixture are separated. It is contemplated that each component be separated in a stepwise manner, such that the separated portions of each component are relatively pure or homogenous (i.e., the major percentage of the separated portion is primarily comprised of the separated component).

As used herein, the term "food" is used in reference to any solid, liquid, semisolid or other material that is used for the nutrition of living things. The term includes any substance that can be taken into the body of an animal or plant to maintain its life and/or growth. It is not intended that the term be limited to any particular type of food. Indeed, it is contemplated that liquid materials (e.g., "drinks" or "liquid supplements") such as fluid dietary and nutritional supplements be included within the definition. It is also contemplated that the term encompass materials that are used as supplements or additives to other foods. For example, it is intended that the term encompass supplements or additives that are added to a drink in order to provide additional nutritional value to the drink.

As used herein, the terms "feed" and "feedstuff" are used in reference to food that is intended for the nutrition of animals other than humans. it is not intended that the terms be limited to any particular type of feed, and may include any solid, liquid, semisolid, or other material that is used to maintain the life and/or growth of nonhuman animals. It is contemplated that the term include materials used as feed for commercially valuable animals such as livestock (e.g., cattle, sheep, goats, hogs, horses, lagomorphs, etc.), as well as companion animals (e.g., dogs, cats, horses, rodents, lagomorphs, etc.), and laboratory animals (e.g., nonhuman primates, rodents, lagomorphs, etc.). Thus, it is not intended that the term be limited to materials fed to any particular genus, species, breed, variety, or type of nonhuman animal.

As used herein, the term "sample" is used in reference to any material of interest that is treated or analyzed using the present invention. Thus, it is contemplated that the term encompass the starting material analyzed or treated using the present invention. For example, the term "sample" encompasses the material that is contacted with a resin in an embodiment of the present invention. It is also contemplated that the term will encompass a portion or aliquot of a larger quantity of a particular substance. However, it is also contemplated that the term encompass any quantity of material treated using the present invention.

As used herein, the term "resin" is used in reference to semisolid or solid amorphous organic compounds of vegetable, synthetic, or other origin. It is contemplated that the term be used in reference to materials commonly used in chromatographic (i.e., separation) procedures. It is also contemplated that the term be used in reference to materials such as polymeric adsorbents used to adsorb particular chemical compounds from a sample.

The term "resin" is also used in reference to a solid support (such as beads/particles etc.) capable of interacting and binding various compounds, including whey components in a solution or fluid (e.g., whey concentrate, whey, etc.), thereby separating and/or segregating the components. The removal process is not limited to any particular mechanism. For example, these components may be removed by an adsorbent or by charge (i.e., affinity interaction). The term "adsorbent resin" refers broadly to both natural organic and synthetic substances. Various adsorbent resins have differing characteristics, including different particle sizes, surface areas, pore sizes, chemical natures (e.g., polystyrene divinylbenzene and acrylic ester), polarities, etc., in order to allow optimum performance for particular applications (e.g., adsorption of of particular whey components). The adsorbent resins may be packaged in a number of arrangements. It is contemplated that the adsorbent resin be packed in a chromatography column for use in the present invention.

The term "polymer" refers broadly to a material made up of a chain of identical, repeated "base units." The term "crosslinked" refers broadly to linear molecules that attached to each other to form a two- or three-dimensional network. For example, divinylbenzene (DVB) serves as the crosslinking agent in the formation of styrene-divinylbenzene copolymers. The term also encompasses "hypercrosslinking" in which hypercrosslinked networks are produced by crosslinking linear polystyrene chains either in solution or in a swollen state with bifunctional agents.

As used herein, the term "chromatography" is used to refer to the separation of compound(s) of interest from a sample solution or fluid that contains a mixture of compounds. It is contemplated that in some embodiments, the compound of interest that is separated using chromatography materials and methods will be collected (i.e., harvested) and used in any suitable application. It is also contemplated that the term encompass the separation of mixed substances (e.g., a solution) by the passage of the mixed substances through an adsorbing medium. In a preferred embodiment, "chromatography" is used in reference to the passage of a mixture through an adsorbing medium such as a resin suitable for chromatography.

As used herein, the term "chromatography column" or "column" is used in reference to any type of column design that is used for chromatography. Thus, it is contemplated that any type of chromatography column or method suitable for use with liquids or fluids will be used successfully in the present invention. For example, it is contemplated that columns designed for axial, vertical, spiral, as well as radial or horizontal chromatography flow of sample fluids or liquids through the column will be used in the methods of the present invention and/or with the materials of the present invention. It is contemplated that columns such as those disclosed in U.S. Pat. Nos. 3,422,605, 3,453,811, 3,780,866, 4,133,562, 4,354,932, as well as the RFC columns disclosed in U.S. Pat. Nos. 4,865,729, 4,676,898, 4,627,918, and 5,452,659, all of which are herein incorporated by reference, will be used successfully in the present invention.

As used herein, the term "RFC" is used in reference to a chromatography column that is characterized as having radial or horizontal flow. It is not contemplated that the present invention be limited to any particular RFC format, size, or shape. Indeed, it is contemplated that cylindrical, conical, and tubular, as well as wedge-shaped (i.e., triangular), and/or other shapes will be successfully used in the present invention.

As used herein, the terms "bed volume" and "column volume" are used interchangeably in reference to the volume of resin packed into a chromatography column. The term "bed volume" is also used in reference to a volume of liquid or fluid (e.g., juice, water, solvent, etc.), added to a column in a volume that is equal to the volume of resin present in the column. For example, one bed volume may be expressed as "1 BV=1 m$^3$ resin."

As used herein, the term "bed volume per minute" (or "BV/min") is used in reference to the number of bed volume equivalents of fluid that will pass through the bed volume during a one minute period. Thus, the term provides a "flow rate," which indicates that fluid is passed through the column at a certain rate of flow. Thus, as used herein, the term "flow rate" is used in reference to the speed at which a fluid or liquid (e.g., whey water, solvent, etc.) passes through the resin present in a packed chromatography column. For example, if the flow rate for a particular column and sample fluid is indicated as being one bed volume per minute, this means that the sample fluid passes through the column at a flow rate of 1 BV/minute throughout the chromatography process.

As used herein, the term "breakthrough" is used in reference to situations in which compounds to be removed from a fluid are not removed. For example, breakthrough occurs during chromatography when the resin is incapable of binding the compound to be removed and the compound remains in the fluid sample used in the column. Breakthrough of the compound usually starts when the resin becomes saturated with the compound. The occurrence of breakthrough is potentially the result of numerous variables, including, but not limited to, the flow rate, pH, ionic strength of the sample and/or buffer, and the presence of compounds other than the compound of interest in the sample fluid.

As used herein, the term "substantially removed," is used in reference to the removal of a large percentage of a compound desired to be removed.

As used herein, the term "single strength" is used in reference to whey solution or another liquid that has not undergone any concentration procedures.

As used herein, the term "recycle" refers to the re-use of any component within a method. In particularly preferred embodiments of the present invention, buffers used during the isolation of whey constituents may be recycled during subsequent processing runs.

As used herein, the term "cleaning in place" refers to the cleaning of a chromatography resin while it is packed in the column to be used for separation of whey constituents.

As used herein, the term "container" refers to any receptacle or vessel suitable to hold chromatography resins and other materials. For examples, it is intended that the term encompass chromatography columns of any type, including but not limited to axial flow and radial flow columns, as well as vats, beakers, tubs, flasks, and chambers. Thus, it is not intended that the term be limited to any particular receptacle or vessel type or size.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); Moj (Mojonnier; a standard analytical method used by the dairy industry to determine fat [butterfat]); M (Molar); µM (micromolar); N (Normal); mol (moles); µmol (millimoles); µmol (micromoles); nmol (nanomoles); g (grams); mg (milligrams); µg (micrograms); ng (nanograms); l or L (liters); µl (milliliters); µl (microliters); cm (centimeters); mm (millimeters); µm (micrometers); nm (nanometers); w/w (weight percent); w/v (percent weight per unit volume); ° C. (degrees Centigrade); ° F. (degrees Fahrenheit); La Prino (La Prino Food, Tracy, Calif.); Bio-Rad (Bio-Rad Laboratories, Hercules, Calif.); Merck (E. Merck, Darmstadt, Germany); Gelman (Gelman Sciences, Ann Arbor, Mich.); PerSeptive (PerSeptive Biosystems, Inc., Cambridge, Mass.); Shimadzu (Shimadzu Scientific Instruments, Inc., Columbia, Md.); Graver (Graver Chemical Co., Glasgow, Del.); Microgon (Microgon, Laguna Hills, Calif.); Abcor (a division of Koch Membrane Systems, Inc., Pleasanton, Calif.); Novex (Novex, San Diego, Calif.);

Monsanto (Monsanto Chemical, Chesterfield, Mo.); Spontex (Spontex, Inc., Columbia, Tenn.); FMC (FMC BioProducts, Rockland, Me.); Land O' Lakes (Land O' Lakes, Inc., Arden Hills, Minn.); Davisco (Davisco, Inc., Le Sueur, Minn.); Kitchen Aid (Kitchen Aid, obtained from Stephan Machinery Corp., Columbus, OH); Brookfield (Brookfield, Stoughten, Mass.); Western Dairy (Western Dairy Products, Inc., Petaluma, Calif.); and Ballas (Ballas Egg Products Co., Zanesville, Ohio.).

In all of the following Examples, unless otherwise indicated, the electrophoresis procedures were conducted as follows. The gels used were 10 mm, 10 well, 4–20% gradient Tris/Glycine gels (Novex) run on a vertical gel slab chamber (X-cell II module; Novex), for 90 minutes at a constant voltage. The buffers and protocols used were those recommended by Laemmli (Laemmli, Nature 227:680–685 [1970]).

After completion of electrophoresis, the gels were detached from their protective plastic frames, washed with distilled water, placed in containers and stained with Coomassie blue staining solution (24% ethanol, 10% acetic acid, 0.5% $CuSO_4.5H_2O$, and 0.05% Coomassie R-250). Briefly, the washed gels were submerged in staining solution. The containers holding the gels were then placed in a microwave or water bath and heated to about 90° C., for 60 seconds. The containers were then placed on a slow speed shaker for 90 minutes at 100 rpm. The staining buffer was then removed, the gels rinsed with distilled water and submerged in destaining buffer (10% ethanol and 10% acetic acid). The submerged gels were then placed on a slow speed shaker and destained for approximately 2 hours at 100 rpm. The gels were then washed and dried between pre-wetted cellophane papers overnight at room temperature or for two hours in a gel dryer.

In some of these Examples, water treated with reverse osmosis was used ("R.O. water"). In this reverse osmosis process, commercial reverse osmosis water treatment membranes and protocols were used to remove many of the salts present in tap water. It is contemplated that distilled water would also be acceptable for use in these Examples. R.O. water was used as described in these Examples as it is less expensive to prepare than distilled water.

EXAMPLE 1

Sequential Separation Of Sweet Whey Proteins

Commercial whey, a by-product of mozzarella cheese manufacture La Prina was initially clarified using a clarifier to remove casein fines, centrifuged to remove milk fat residue (i.e., to produce "skimmed whey"), pasteurized at 162° F. for approximately 18 seconds, and chilled to 40° F. by passing it through HTST (high temperature, short time) plate heat exchangers. Then, the pH of 1000 ml of this skimmed commercial sweet whey containing 6.2% total solids, was adjusted to 3.8 with acetic acid at 40° F. The composition of the whey product used in this Example is presented in Tables 3 and 4. A flow diagram showing the steps in the elution protocol is presented in FIG. 2.

TABLE 3

Whey Components

| Components | Percentage |
|---|---|
| Total Solids | 6.2 |
| Lactose | 4.5 |
| Protein | 0.8 |
| Fat | 0.08 |
| Ash | 0.77 |
| Lactic Acid | 0.05 |

TABLE 4

Whey Protein Composition

| Protein | Percentage |
|---|---|
| β-lactoglobulin | 0.29–0.32 |
| α-lactalbumin | 0.07–0.11 |
| Serum Casein | 0.10–0.12 |
| Immunoglobulin | 0.04–0.06 |
| Lipoprotein | 0.02–0.06 |
| Bovine Serum Albumin | 0.03–0.04 |
| Lactoferrin | 0.002–0.003 |
| Lactoperoxidase | 0.002 |

The whey was then passed at a flow rate of 100 mls/min., through a 250 ml radial flow chromatographic column prepacked with a strong S cation exchange resin ("MARCRO-PREP" 50 High S, Bio-Rad). The column was previously equilibrated with 0.05 M acetate buffer at pH 3.8. All of the whey proteins were bound to the resin matrix, and the effluent containing various components including peptides, lactose, minerals, lactic acid, and non-protein nitrogenous components was allowed to pass through. This effluent is referred to as "deproteinized whey." The resin with the bound proteins was then washed with 0.05 M acetate butter at pH 3.8 to remove unbound materials. The baseline value was determined to be <10% of full scale. The wash contained no solids, with the exception of a trace of riboflavin detectable.

Proteins bound to the column were then sequentially eluted. First, immunoglobulin (e.g., IgG) and β-lactoglobulin were eluted in sequential order with a buffer at pH 4.0 containing 0.1 M sodium acetate and 0.5 M sodium chloride. The column was then washed with 0.05 M sodium acetate buffer at pH 4.0 to bring the conductivity back to the base line (e.g., approximately less than 5% of full-scale). This value was chosen in order to provide a better yield of eluted product.

Next, the α-lactalbumin (α-La) fraction was eluted with a pH 5.0 buffer containing 0.1 M sodium acetate and 0.1 M sodium chloride. The column was again reconditioned with a pH 5.0 buffer containing 0.05 M sodium acetate to bring the conductivity back to the initially established base line. Bovine serum albumin (BSA) was then eluted with a 0.05 M phosphate buffer at pH 7.0. Thereafter, lactoferrin (LF) was eluted at pH 7.5 with a buffer containing 0.05 M sodium phosphate and 0.5 M sodium chloride.

The column was again regenerated by washing it with a solution containing 0.2 M sodium hydroxide and 1 M sodium chloride, followed by a water wash, and then with a 20% ethanol solution to sterilize the column. The column was then rinsed with water and equilibrated with acetate buffer at pH 3.8 for reuse.

Figure 3:
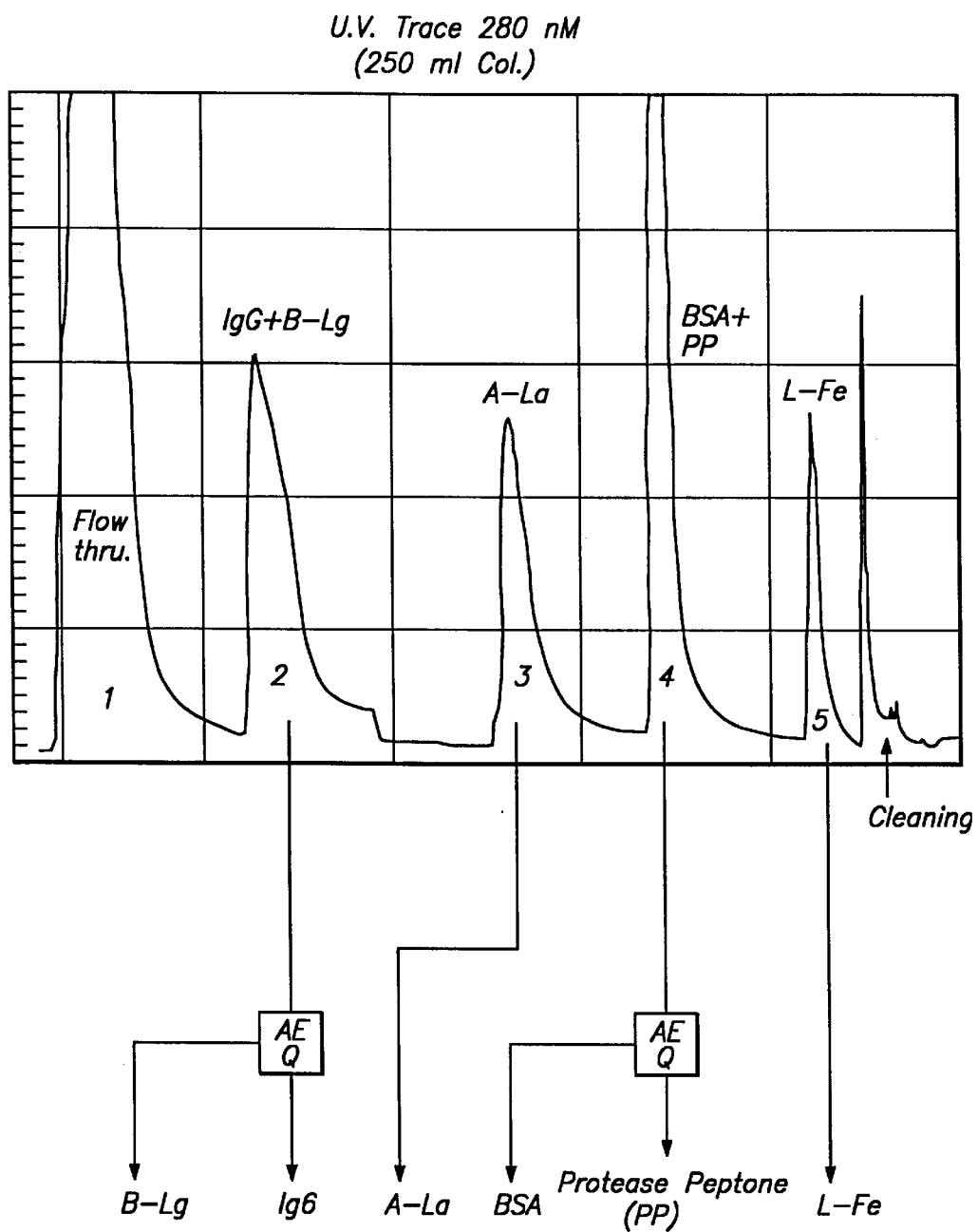
FIG. 3 provides an elution profile of separated proteins vs. time, using a 250 ml RFC column (i.e., bench scale).

Fractions of each of the eluted proteins were collected as elution "peaks" for further separation, concentration, and other treatment protocols. The elution sequence with the different protein peaks in terms of their UV absorption at 280 nm is presented in FIG. 3. The purity of the proteins in each peak was monitored by sodium dodecyl sulfate-polyacrylamide gel electrophoresis (SDS-PAGE), using a 4–20% gradient gel (Novex) and gel scanner (Model 1312, Shimadzu). The scan results were used to determine the area of each band of protein, and the percentage represented by the major band was calculated, in order to determine the purity of this individual protein in the sample.

Protein recoveries were monitored using the Bio-Rad protein assay method (i.e., the Bradford method). The protein content in the gels was monitored through use of the gel scanner. Tables 5 and 6 below provide data for these assays at various stages of the elution scheme.

TABLE 5

Summary Of Bio-Rad Assay Data

| | | | |
|---|---|---|---|
| (#0) | Column Load 1.0 L Treated Whey 4.3 mg/ml Total Protein | 4.3 g loaded | |
| (#1) | Column Flow-Through 1.65 L 0.2 mg/ml Total Protein | 0.3 g (7%) | |
| (#2) | β-Lg - IgG Fraction 2.4 L 1.2 mg/ml Total Protein | 2.9 g (67%) | |
| (#3) | α-La Fraction 1.25 L 0.5 mg/ml Total Protein | 0.6 g (14%) | |
| (#4) | BSA Fraction 1.625 L 0.3 mg/ml Total Protein | 0.4 g (9%) | |
| (#5) | L-Fe Fraction 0.625 L 0.09 mg/ml Total Protein | 0.05 g (1%) | |
| (#6) | Wash 1 1.6 L 0.03 mg/ml Total Protein | 0.05 g (1%) | |
| (#7) | Wash 2 0.4 L 0.09 mg/ml Total Protein | 0.04 g (1%) | |
| | Total Recovery = 4.3 g = 100% Accountability | | |

TABLE 6

Summary Of Gel Scan Data

| Gel No. | Test Sample | Approx. Composition | Estimated Purity (Gel Scan) |
|---|---|---|---|
| 0 | Whey | β-lactoglobulin (56%) α-lactalbumin (17%) BSA (2%) Immunoglobulin (3%) Other (22%) | |
| 1 | Deproteinized Whey | No Protein Detected | |
| 2 | β-lactoglobulin Immunoglobulin | β-lactoglobulin (94%) Immunoglobulin (2%) | β-lactoglobulin (83%) Immunoglobulin (14%) |
| 3 | α-lactalbumin | α-lactalbumin (94%) | α-lactalbumin (82%) |
| 4 | BSA | BSA (62%) | BSA (70%) |
| 5 | Lactoferrin Lactoperoxidase | Lactoferrin (45%) Lactoperoxidase (45%) | 55% 50% |

EXAMPLE 2

An Alternative Protocol For Elution Of Whey Proteins liter RFC column was packed with a "MACRO-PREP" 50 S resin (Bio-Rad). was then conditioned, equilibrated, loaded, eluted and reconditioned in the as described in Example 1 above, except that the flow rates, volume of whey loaded on to the column, and buffer volumes were varied in order to compensate for the additional column volume. Thus, in this Example, a 20 L RFC column was used to test process scale-up from a 250 ml RFC column as described in Example 1.

This represents an eighty-fold scale-up increase. In order to maintain the same protocol parameters with the 20 L column as with the 250 ml column, the amount of whey loaded and equilibration, elution, and cleaning buffers were increased by approximately 80 times (i.e., in this Example, 80 L of whey was loaded onto the column, as this is approximately equivalent to 1 L of whey loaded onto the 250 mls RFC column).

Figure 4:
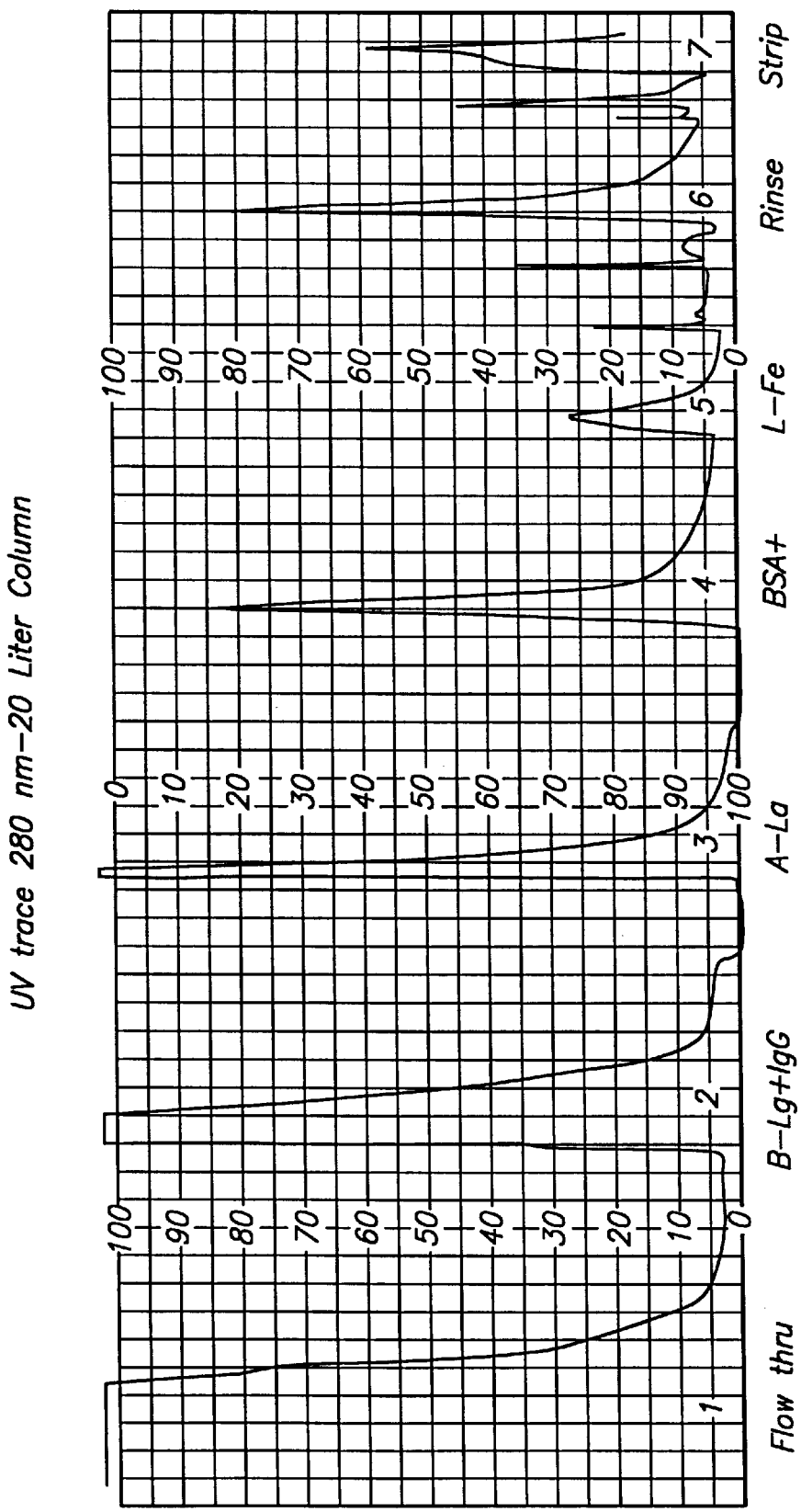
FIG. 4 shows the elution sequence of different proteins in terms of their UV absorbance, using a 20 liter RFC column (i.e., pilot scale).

Protein elution peaks were monitored at 280 nm using an ultraviolet (UV) spectrophotometer (model 1201, Shimadzu). A graphical trace of the eluted proteins eluted with their relative concentrations is presented in FIG. 4. The proteins eluted with their respective percentages of purity are shown in Tables 7 and 8.

TABLE 7

Protein Yields In Eluate Fractions (20 L Column; Flow Rate 8 L/min; Whey Load 80 L)

| | Protein (g/L) | Volume (L) | Protein Yield Load (g) | % |
|---|---|---|---|---|
| Whey Load | 8.8 | 80 | 704 | — |
| Flow Through (P-1) | 0.9 | 97 | 87 | 12 |
| β-La + Ig (P-2) | 2.8 | 89 | 249 | 35 |
| α-Lactalbumin (P-3) | 1.1 | 94 | 103 | 15 |
| BSA (P-4) | 1.1 | 102 | 112 | 16 |
| Lactoferrin (P-5) | 0.9 | 45 | 41 | 6 |
| Rinse (P-6) | 0.8 | 22 | 18 | 3 |
| Stripping Solution (P-7) | 1.2 | 29 | 35 | 5 |

Protein Recovery: 84%; Protein Accountability: 92%

TABLE 8

Purity of Proteins As Determined by Gel Scan

| Proteins | Purity (Gel Scan) % |
|---|---|
| β-Lactoglobulin | 82 |
| Immunoglobulin | 11 |
| α-Lactalbumin | 84 |
| Bovine Serum Albumin | 59 |
| Lactoferrin | 52 |

EXAMPLE 3

Preparation Of An Anionic Exchange Resin Column

A 250 ml RFC column was packed with a strong base, anionic exchange resin—MACRO-PREP" 50 Q (Bio-Rad). The column was first conditioned with a buffer containing 0.2 M NaOH+1 M NaCl, at a flow rate of 100 ml/min for 10 minutes. The column was then equilibrated with 0.01 M sodium phosphate at pH 6.90 at a flow rate of 100 ml/min for 10 minutes. This column was then used to separate immunoglobulins (e.g., IgG) and β-lactoglobulin that eluted together as overlapping peaks from Examples 1 and 2 above. It is contemplated that this mixture be incorporated into dietary formulations or used for further separation of the two protein components. This column was then used as described in Example 4.

EXAMPLE 4

Separation Of Immunoglobulins and Peptides From β-lactoglobulin

The eluate represented by peak 2, collected from the fractionated material from the process described in Example 1, and containing immunoglobulins and β-lactoglobulin at pH 4.0, was passed through a 10,000 molecular weight cut-off UF membrane (Abcor). This step was done in order to concentrate the proteins, reduce the buffer salt concentration and thereby reduce the ionic strength of the solution. The proteins were further concentrated to 5 ×, and buffer salt concentrations were reduced to about one-fourth their eluting concentration by diafiltration with distilled water.

The pH of the diafiltered and concentrated protein solution was adjusted to 6.9—6.9, with a 2.0 M solution of NaOH. Two liters of this protein solution at pH 6.9 were loaded onto the pre-conditioned RFC column as described in Example 3, at a flow rate of 100 ml/min. The column was washed with 0.01 M sodium phosphate buffer at pH 6.9 until the UV baseline at 280 nm was <10% of full-scale.

Immunoglobulins which did not bind to the resin passed through the column with the wash and was collected for further processing. The adsorbed β-lactoglobulin was then eluted from the column with 0.05 M sodium citrate buffer at pH 3.0 and collected. The column was rinsed with distilled water, stripped of residual proteins with 0.2 M NaOH+1 M NaCl solution, followed by a 20% ethanol wash, and again re-equilibrated with sodium phosphate buffer at pH 6.9, in preparation for a repeated cycle.

EXAMPLE 5

Separation And Isolation Of BSA

Figure 5:
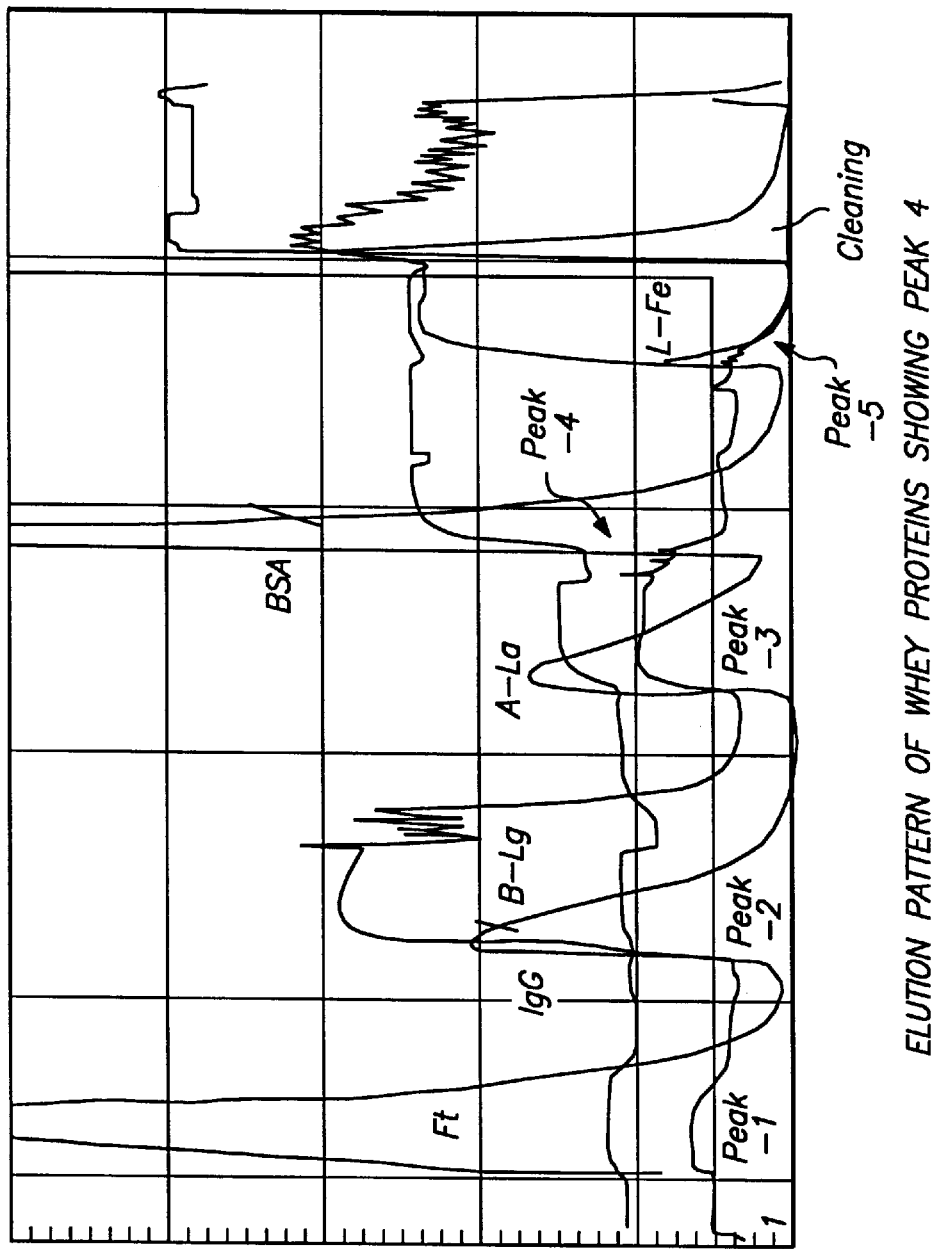
FIG. 5 represents the elution pattern and the location of peak 4.

The eluate represented by peak 4, collected from the fractionated material from the process described in Example 1, and containing BSA, and protease peptone at pH 7.0 was concentrated and diafiltered as described in Example 6. The pH was then adjusted to 5.5 with acetic acid. A 250 ml RFC column prepared as described in Example 3 was rinsed with distilled water at a flow rate of 100 ml/min., and two liters of the protein solution were loaded onto the column. The column was again flushed with distilled water at a flow rate of 100 ml/min to elute the nonadsorbed protease peptone and to establish a stable UV baseline (i.e., <10% of full-scale at 280 nm, using the same Shimadzu spectrophotometer as described in the previous Examples). The eluate containing the protease peptone was collected for further use. The adsorbed BSA was thereafter eluted with sodium phosphate buffer containing 0.2 M sodium chloride at pH 7.0 using three column volumes of buffer. FIG. 5 shows the elution pattern and the location of peak 4.

EXAMPLE 6

Elution And Separation Of β-Lactoglobulin From Liquid Whey

A 250 ml radial-flow chromatographic column packed with a strong base anionic exchange resin ("MACRO-PREP" 50 Q, Bio-Rad) was washed and regenerated according to manufacturer's instructions. The column was then equilibrated with 0.05 M sodium phosphate (tribasic) at pH 6–7, at a flow rate of 100 ml/min for 10 min. Two liters of clarified, skimmed, pasteurized sweet whey from mozzarella cheese manufacture, were chilled to 40° F. and the pH adjusted to 6.5 with 5 M sodium hydroxide, and loaded onto the column. Flow rates in the range of 50–100 ml/min were found to be acceptable. The column was then washed with the loading buffer (0.05 M sodium phosphate at pH 6.5). Under the conditions utilized, all of the whey proteins except β-lactoglobulin were relatively more positively charged than other whey proteins, and did not bind to the anionic exchange resin. The β-lactoglobulin being negatively charged, bound to and was retained by the anionic exchange resin. The effluent containing non-bound proteins (α-lactalbumin, immunoglobulins, bovine serum albumin, and lactoferrin) were allowed to pass through the column. The effluent was collected and stored at 40° F. for further processing.

The absorbed β-lactoglobulin was then eluted from the column with a pH 7.5 buffer containing 0.05 M sodium phosphate and 0.5 M sodium chloride. This eluate containing β-lactoglobulin may be processed further to prepare a shelf-stable product in the same manner as described in the flow diagram shown in FIG. 1.

The column was cleaned and regenerated with 1 M sodium chloride at a flow rate of 125 ml/min for about four column volumes (1 liter), and stripped with 1 M NaOH at the same flow rate, washed with water, and then equilibrated with the loading buffer.

EXAMPLE 7

Figure 6:
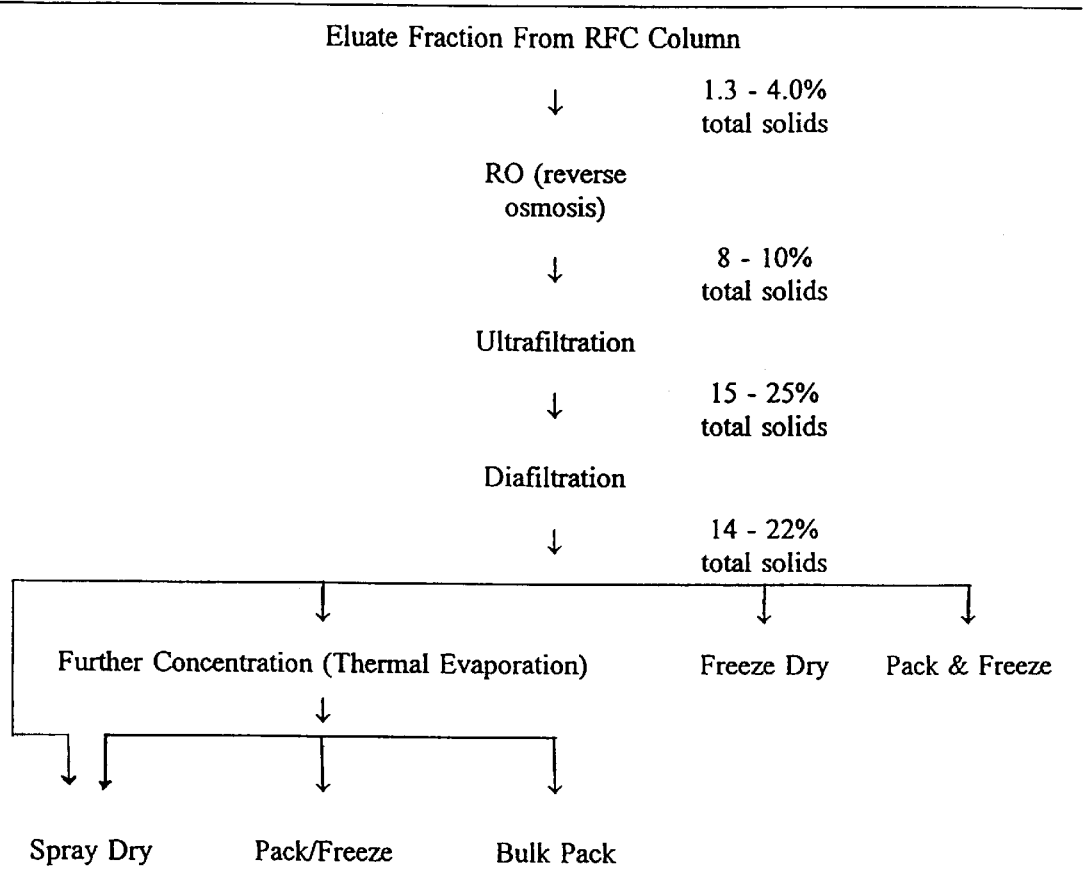
FIG. 6 is a flow chart showing the preparation of the final product as outlined in Example 7.

Elution And Sequential Separation Of Four Proteins From A Non-α-lactoglobulin Fraction Of Liquid Whey The flow-through fraction from Example 6, containing about 0.55% of the original whey protein, was passed through a 5,000–10,000 molecular weight cut-off, spiral ultra-filtration membrane (Abcor) to 35% of the original volume. The purpose of this step was to achieve partial protein concentration, and also for reduction of soluble salts associated with the protein solution. This pre-treatment procedure facilitated the optimum absorption of loaded proteins, and further the sequential desorption of immunoglobulins, α-Lac, BSA and L-Fe protein fractions as outlined in Example 1. The pH of the prepared flow-through was adjusted to 3.8 with acetic acid, and 1500 ml portion was loaded onto a pre-equilibrated 250 ml RFC column packed with a strong S-cationic exchange resin ("MACRO-PREP" High S, Bio-Rad). The equilibration buffer was composed of 0.05 M sodium acetate buffer at pH 3.8. Washing, sequential elution and regeneration steps as described in Example 1 were followed. The eluted protein fractions were individually passed through a 5,000–10,000 MW cut-off membrane (Abcor) to concentrate the proteins and remove salt residues. The concentrated protein was then processed further to a finished product as shown in the flow diagram shown in FIG. 6.

EXAMPLE 8

Cleaning In Place

In this Example, an efficient, effective method to clean chromatography columns was developed. In the food and dairy industries, sanitation is of prime importance. Thus, a method that uses cleaning solutions that are acceptable to the industry and regulators, effective and readily available at the plant was considered to be important. Currently, caustic, acid, and sodium hypochlorite solutions are commonly used in the dairy industry for the cleaning and sanitation of equipment. As it is crucial that the chromatographic resin be clean and regenerated before beginning a new production cycle, a method for the regeneration of the resin packaged within the column (e.g., the RFC column of one embodiment of the present invention), was developed that improves the sanitation process, while extending the life of the resin.

In this Example, various parameters were modified in order to develop a method to clean the resin in place (CIP).

The inclusion of sodium hypochlorite was found to improve the cleaning ability and sanitation of the process. It also appeared that ethanol apparently eliminated the build up of lipids during the processing of multiple runs. Although it is not necessary for use of the present invention, during multiple runs with prior art methods, there is often a change in capacity of the resin, as lipids accumulate in the resin. This results in the build up of pressure within the column, and consequently, a decrease in the flow rate. The ethanol appeared to alleviate these problems.

The protocol developed during this process is shown in Table 9. RFC columns were packed with "MACRO-PREP" High Q or High S (BioRad), were used in this Example. As indicated in Table 9, at the end of a whey processing cycle, the packed column was first rinsed with 2 column volumes (CV) of water at a flow rate (FR) of 0.6 CV/minute. The column was sanitized with 2 CV of 200 ppm sodium hypochlorite solution at a flow rate of 0.6 CV/min. The bed resin was then regenerated by passing 0.5 M sodium hydroxide (2 CV) at a flow rate of 0.4 CV/min. Next, the column was rinsed (2 CV) with water to remove caustic residues, at a flow rate of 0.6 CV/min. The bed resin was again regenerated with 2 CV of 0.5 N HCl. For the last daily production cycle, acetic acid was used in place of the HCl in this step. The column was rinsed with 2 CV water at a flow rate of 0.6 CV/min. to remove acid residues. It was found that this step was not required, if the previous regeneration step (i.e., step 5) was not conducted. The column was then cleaned with 20% ethanol, methanol, or isopropanol, by circulation at 0.6 CV/min for 15 minutes. Each of these alcohols (ethanol, methanol, and isopropanol) were found to be equivalent in their performance.

This step was found to be required only once per week, or after completion of 100 cycles of whey preparation. Furthermore, it may be combined with step 5 (i.e., the previous regeneration step), if a time savings is desired. Finally, the resin was equilibrated with the appropriate equilibration buffer, prior to starting a new production cycle.

TABLE 9

Cleaning In Place (CIP)

| Step | Method/ Reagent | CV | RF cv/min | Time (min.) | Per Cycle | Daily | Weekly |
|---|---|---|---|---|---|---|---|
| 1 | Water Rinse | 2 | 0.6 | 3.3 | x | x | x |
| 2 | Sodium Hypochlorite (200 ppm) | 2 | 0.6 | 3.3 | x | x | x |
| 3 | Sodium Hydroxide (0.5 M) | 2 | 0.4 | 5.0 | x | x | x |
| 4 | Water Rinse | 2 | 0.6 | 3.3 | x | x | x |
| 5 | Hydrochloric Acid (0.5 N) | 2 | 0.4 | 5.0 |  | x | x |
| 6 | Water Rinse | 2 | 0.6 | 3.3 |  | x | x |
| 7 | Ethanol (20%) | Rec.* | 0.6 | 15 |  |  | x |
| 8 | Equilibration | 3 | 0.6 | 3.3 | x | x | x |

Rec* = Recirculation (i.e., continual circulation).

The amount of time required for CIP per cycle was 18.2 minutes; for daily CIP, the amount of time required was 26.2 minutes; and for weekly CIP, the amount of time required was 41.2 minutes. There is a total of eight cleaning steps. However, some steps are completed during each cycle (i.e., 1, 2, 3, 4, and 8). This requires about 18 minutes to complete. For the last cycle of the day (i.e., once per day), steps 5 and 6 were also included. Once per week, step 7 was also included during the last cycle of the week (e.g., cycle 100).

It was determined that no significant differences were produced in cleaning quality of the resin if the solution temperatures were varied between room temperature and 140° F., with temperatures tested at 70°, 100°, 120°, and 140° F. The 140° F. test was included, as it is within the range of temperatures (120–160° F.) normally used in the cleaning steps in dairy manufacturing using acids or alkali. The 70° F. temperature was included as the water is commonly used at this temperature.

In addition, the resin life appeared to be extended when this CIP method was used to regenerate the columns. Resin manufacturers do not usually provide an estimation of the resin life cycle for true (i.e., production) applications, although the "MACRO-PREP" High S resin circulated continuously with 1 M NaOH, was indicated to last about one week, without problems. During the development of the present invention, it was observed that 860 cycles of complete operation can be completed with one resin preparation cleaned according to one embodiment of the CIP method. In these experiments, each cycle consisted of equilibration, loading of seven column volumes of whey, washing, eluting whey protein isolate (i.e., all whey proteins were collectively eluted), cleaning the column with sodium hydroxide and sodium chloride as set forth in Table 9, rinsing with water, and then equilibration for the next cycle. Indeed, based on our results, it is contemplated that our CIP process may extend the life cycles of the resin to over 2500 cycles, under normal production conditions.

EXAMPLE 9

Buffer Development

In this Example buffers suitable for use with the methods of the present invention were developed. The first attempts were based on buffers selected to separate whey proteins based on either the isoelectric points (PIs) of the whey protein, or ionic strengths of the buffers. The isoelectric point of $\beta$-lactoglobulin is 5.35–5.49; for $\alpha$-lactalbumin, it is 4.20–4.5; for immunoglobulin, it is 5.5–8.3, for BSA, it is 5.13; for proteose peptones, it is 3.3–3.7; and for lactoferrin, it is 7.8–8.0.

In this Example, fine-free mozzarella cheese whey obtained from Le Prino Foods was adjusted to the desired pH prior to loading into a 250 ml RFC column packed with "MACRO-PREP" High S (Bio-Rad) cation exchange resin, as described in Example 1, and equilibrated with buffer A and B. Two buffers were used for each test run (i.e., buffers A and B), as indicated in the following table. As indicated, buffer A was always lower in either pH or ionic strength compared with Buffer B. As the gradients proceeded, the ratios of buffer B to A in the eluting buffer was increased, resulting in protein desorption.

For each run, the packed column was equilibrated with buffer "A" for 3 column volumes (CV), before loading the pH-adjusted whey. After the column was loaded with the whey, the column was washed using buffer A until the UV reading was flat, at less than 5% of the full scale of the chart paper, as described in Example 1. Next, a gradient elution with buffers "A" and "B" were done as shown in the following table. After completion of the gradients, the column was then cleaned as described in Example 1.

TABLE 10

Buffer Development

| Run | PI or IS | pH | pH Adjustment of Whey Acid | Gradient Buffer A | Buffer B | Time (min) |
|---|---|---|---|---|---|---|
| 1 | PI | 3.0 | Acetic | 0.5 M Na Acetate pH 3.2 | 0.05 M Na Acetate pH 10.0 | 60 |
| 2 | PI | 3.0 | Acetic | 0.05 K Acetate pH 3.2 | 0.05 K Acetate pH 10.0 | 60 |
| 3 | PI | 3.0 | Phosphoric | 0.05 Na Phosphate* pH 3.2 | 0.05 Na Phosphate*, pH 10.0 | 90 |
| 4 | PI | 3.0 | Phosphoric | 0.05 K Phosphate pH 3.2 | 0.05 K Phosphate pH 10.0 | 90 |
| 5 | PI | 3.5 | Acetic | 0.05 M Na Acetate pH 3.5 | Buffer A + 1 M NaCl | 90 |
| 6 | IS | 3.5 | Phosphoric | 0.05 Na Phosphate* pH 3.5 | Buffer A + 1 M NaCl | 90 |

*Monohydrate

Following the chromatography runs, selected samples (at different gradient were electrophoresed on SDS-PAGE gels as described. The SDS-PAGE results ted that none of these runs resulted in true separation of the individual proteins. these attempts to separate individual whey proteins based on either their PIs, or changes in the ionic strength (IS) of elution buffers were unsuccessful.

Numerous attempts were then made, based on the information gathered in these early, unsuccessful runs, to develop buffers for use in the present invention, as shown in the chromatograms in FIG. 18 (i.e., chromatograms 21, 22, 23, and 24).

EXAMPLE 10

Utilization of Recycled Whey By-Product and/or Buffers

In this Example, the use of recycled whey by-products and/or buffers was investigated. These experiments were conducted in view of the large volume of whey processed by the dairy industry on a daily basis. For example, the average dairy processor usually deals with over two million liters of whey per day. Implementation of chromatographic process in the dairy industry involves adaptation of the processes to the large volume processes and associated reagent costs. The recycling of whey by-products and/or buffers was viewed as providing a potential means to reduce the process and chemical costs, and reduce the volume of buffer needed.

In these experiments, the buffering capacity of whey (i.e., due to minerals, ions, etc.), for equilibration of packed resin beds or elution of bound proteins, after either minor conductivity and/or pH adjustments was determined and adjusted (as needed). Recycling of elution and regeneration buffers (after minor conductivity and/or pH adjustments, as needed), were also investigated.

A. Separation of Whey Products Using Whey By-Products

"MACRO-PREP" High S resin (strong cation exchange support; Bio-Rad) was packed into a 100 ml RFC column and reconditioned by passing 2 column volumes (CVs) 0.5 M NaOH, 3 CV water, 2 CV 0.5 M HCl, and 5 CV water through the column. The column was equilibrated with either 0.05 M sodium acetate (pH 3.8) or deproteinized whey (pH 3.8) clarified through a charcoal (powdered activated carbon [Ecosorb], S-407, Graver) column (2.5 cm x 10 cm) in whey buffer at pH 3.8. "Whey buffer" refers to the clear solution with buffering capacity that was obtained (i.e., the effluent) when deproteinized whey was passed through the charcoal column.

Whey (700 ml) at pH 3.8, was passed through the column at a flow rate of 40 ml/min (0.4x CV/min.). The column was then washed with water (2 CVs), and bound proteins were sequentially eluted. The first protein eluted was β-lactoglobulin. This protein was eluted using whey buffer with 0.8 M NaCl, pH 3.5 (3 CV). The column was then washed with 1 CV water, and then the α-lactalbumin was eluted using 3 CVs whey buffer with 0.2 M NaCl, pH 5.0. The column was again washed with water (1 CV). BSA and other proteins were then eluted with whey buffer with 0.8 M NaCl (3 CV), or 0.05 M sodium carbonate with 0.5 M NaCl (pH 11.0), or 0.1 M NaOH with 0.5 M NaCl, pH 12.0, or 0.05 sodium phosphate with 0.5 M NaCl, pH 8.5. Each of these buffers were equally suitable to elute BSA and other proteins (i.e., BSA and other proteins all came off in one elution). The protein fractions were run on Bio-CAD (PerSeptive) and SDS-PAGE. The SDS-PAGE gels were run as described in Example 1. The Bio-CAD system consisted of a liquid chromatography pump and a variable wavelength detector. A 25 cm x 4.6 mm i.d., Lichrosorb Rβ-18 column (Merck) was used to analyze whey proteins. Whey and whey fractions were filtered through 0.45 μfilter (Nylon Aerodisc, Gelman), and injected into the column (100 μl). A gradient of 40% acetonitrile with 0.1% trifluoroacetic acid and 90% acetonitrile with 0.1 % trifluoroacetic acid, was run in order to separate the various whey proteins The effluent was monitored at 280 nun. The separated whey proteins were analyzed using Bio-CAD software (PerSeptive).

The results showed that deproteinized whey passed through a charcoal column can be used as an equilibration or elution buffer. For column equilibration, whey buffer with a pH of 3.8 is preferred. For elution of β-lactoglobulin from the column, whey buffer with 0.8 M NaCl, pH 3.5, produced a highly purified products, as observed by SDS-PAGE and Bio-CAD. It was determined that the use of higher or lower salt concentrations resulted in the production of purified β-lactoglobulin that also contained α-lactalbumin as a contaminant. For the elution of α-lactalbumin, whey buffer with 0.2 M NaCl, pH 5.0, produced an α-lactalbumin-enriched product, as observed by SDS-PAGE and Bio-CAD. For the elution of BSA and other proteins, whey buffer with 0.8 M NaCl, pH 8.0, or 0.05 M sodium carbonate and 0.5 M NaCl, pH 11.0, or 0.05 M sodium phosphate and 0.5 M NaCl, pH 8.5 were equally suitable.

In addition to the experiments described above, deproteinized whey was clarified with ultrafiltration (10,000 MW cutoff), and tested as described above as an elution buffer at various pHs (3.5 to 3.9) and NaCl concentrations (0.25 M to 0.6 M) for β-lactoglobulin isolation. This filtered deproteinized whey was found to be unsuitable for use, as it could not separate the proteins. Although an understanding of the mechanism is not necessary in order to make and use the present invention, it is believed that the filtered permeate contains certain peptides that negatively affect separation. Ethanol was used to elute the peptides from the charcoal column, followed by extensive dialysis and a sugar test (phenol-sulfuric acid method); these peptides were identified as glycomacropeptides (GMP).

These experiments indicate that whey by-products can be recycled to produce equilibration and elution buffers. As these buffers were obtained from the recycled whey by-products, the process is highly economical.

B. Separation of Whey Proteins Using Recycled Buffers

"MACRO-PREP" High S resin (strong cation exchange support; Bio-Rad) was packed into a 100 ml RFC column and reconditioned by passing 2 CVs 0.5 M NaOH, 3 CV water, 2 CV 0.5 M HCl, and 3 CV water through the column. The column was first equilibrated (cycle 1) with 3 CVs 0.05 M sodium acetate, pH 3.8. In the second and subsequent cycles (up to cycle 75), the column was equilibrated with deproteinized whey, pH 3.8. Thus, one run (1 cycle) was equilibrated with sodium acetate, and then subsequent runs used the same column, with the column being reequilibrated with deproteinized whey prior to loading the sample whey on the column. Although as long as the deproteinized whey was capable of maintaining a suitable pH, it was found to be unnecessary to change the deproteinized whey each day that the process was run, fresh deproteinized whey was used each day.

Whey (700 ml), pH 3.8, was passed through the column at a flow rate of 40 ml/min (0.4x CV/min). The column was then washed with water (2 CV). β-lactoglobulin was eluted from the column with 0.2 M sodium acetate HCl and 0.5 M NaCl, pH 3.5 (3 CVs), and the column was again washed with water (1 CV). α-lactalbumin was eluted from the column with 0.05 M sodium acetate NaOH, and 0.5 M NaCl, pH 11.8 (3 CV). The column was finally cleaned with 0.5 M NaOH (2 CV) and water (3 CV). The column was then reequilibrated with deproteinized whey at pH 3.8.

The β-lactoglobulin and α-lactalbumin fractions were then concentrated using a Microgon ultrafiltration unit (Microgon) as per manufacturer's instructions. The conductivity of the permeates was restored using 5×concentration of the original buffers and the pH adjusted with either HCl or NaOH. On average, 30 ml of the 5×buffer was required to restore the buffering capability of the β-lactoglobulin elution buffer, while for the α-lactalbumin buffer, 20 ml of the 5×buffer was required to restore the buffer capability. The restored buffers were used for the following cycle. After each cycle, the elution buffers were restored to their full elution strength as described above.

After each cleaning cycle, 10 ml of the 5×NaOH (2.5 M) buffer was added to the eluted cleaning solution to restore the conductivity. After cycle 10, new cleaning solution was used (i.e., after cycle 10, 20, 30, etc.). Also, after cycle 10, cleaning with 0.5 M HCl was also conducted (i.e., also after cycle 10, 20, 30, etc.).

The Bio-CAD data (obtained as described previously) showed consistent resolution of protein peaks and purity of the α-lactalbumin and β-lactoglobulin enriched fractions throughout the experiment (i.e., cycle 1 through cycle 75). SDS-PAGE (conducted as described previously) confirmed the purity of the α-lactalbumin-enriched fractions as observed by Bio-CAD.

Kjeldahl nitrogen estimation accounted for all the proteins eluted through the column (e.g., whey, deproteinized whey, the β-lactoglobulin fraction, and the α-lactalbumin fraction). The protein estimations by the standard Kjeldahl method are shown in the following table.

TABLE XX

| | | Protein Estimates | | |
| | | Fractions (total protein, g) | | |
| Cycle # | Whey | Deproteinized Whey | β-Lactoglobulin | α-Lactalbumin |
| --- | --- | --- | --- | --- |
| 1 | 5.88 | 2.66 | 2.31 | 1.05 |
| 28 | 5.88 | 2.66 | 2.56 | 1.02 |
| 35 | 5.81 | 2.66 | 2.66 | 1.02 |
| 60 | 5.85 | 2.67 | 2.67 | 1.03 |

These experiments showed that the buffers used to elute α-lactalbumin and β-lactoglobulin fractions from columns can be recycled, providing an option to dairy processors that is highly economical and does not present a danger to the environment.

EXAMPLE 11

Isolation of Lactoferrin and Lactoperoxidase from Whey

In this Example, methods to isolate two important milk proteins are described. Human milk includes three important proteins with non-specific anti-bacterial activity, namely, lactoferrin, lactoperoxidase, and lysozyme. The methods investigated here were developed for the isolation of lactoferrin and lactoperoxidase.

Lactoferrin is an 80 kDa iron-binding glycoprotein that is present in significantly large amounts in human milk (approximately 2.0 g/L), as compared to bovine milk (approximately 0.1 g/L). Due to its iron-binding properties, it has been proposed that lactoferrin plays a role in the uptake of iron from the intestinal mucosa, and acts as a bacteriostatic agent by withholding iron from iron-requiring bacteria. In addition, its presence in neutrophils and release during inflammation, suggests that lactoferrin is also involved in phagocytic killing and the immune response. Additionally, lactoferrin may function in other ways unrelated to iron-binding (e.g., as a growth factor and/or bacteriostatic agent).

Lactoperoxidase catalyzes the conversion of peroxide ($H_2O_2$) to water. In the presence of thiocyanate, lactoperoxidase forms an enzyme-$H_2O_2$ complex, a bactericidal compound capable of destroying Gram-negative bacteria. This system may be used to improve the shelf-life of raw milk. During infections and other disturbances of the synthetic activity of the mammary gland, the increased antibacterial defense system is reflected in the concentration of lactoperoxidase in milk.

Multiple test runs were conducted during the development of the methods. Comparisons of these five test methods are presented following the descriptions of the four methods.

Method 1.

In these experiments, "MACRO-PREP" High S (Bio-Rad) was packed in a 10 ml column (2.5 cm×2.1 cm), and reconditioned by passing 3 CV 0.5 M NaOH, 3 CV water, 3 CV 0.5 HCl, and 5 CV water. The column was then equilibrated with 0.025 M sodium acetate, pH 6.3.

Whey (1 000 ml), pH 6.3, was passed through the column at a flow rate of 4 ml/min (0.4× CV/min). The column was then washed with 2 CV 0.025 M sodium acetate, pH 6.3. Bound proteins were sequentially eluted from the column at a flow rate of 4 ml/min with buffers containing 0.1 M, 0.2 M, 0.3 M, 0.4 M, 0.5 M, 0.6 M, and 0.7 M sodium acetate (pH 9.0), and 0.05 trisodium phosphate with 0.5 M NaCl (pH 11.8). For the elution of the proteins, 3 to 5 CV of buffer was used as follows. The proteins that eluted with 0.2 M sodium acetate (5 CV), as well as with 0.3 M sodium acetate (3 CV) were determined to be lactoperoxidase by SDS-PAGE (conducted as described previously). The total protein content of the 0.2 M and 0.3 M sodium acetate fractions were 30.1 mg and 32.0 mg, respectively, as determined using the BioRad protein estimation method.

The protein that eluted with 0.05 M Trisodium phosphate containing 0.5 M NaCl (2 CV) was found to be lactoferrin, as determined by SDS-PAGE (conducted as described previously). The total protein in the fraction was 96.0 mg. In addition to the test samples, standard proteins were run on SDS-PAGE, and their mobilities were compared with those of lactoferrin and lactoperoxidase.

Method 2.

In these experiments, "MACRO-PREP" High S (Bio-Rad) was packed in a 10 ml column (2.5 cm×2.1 cm), and reconditioned by passing 3 CV 0.5 M NaOH, 3 CV water, 3 CV 0.5 HCl, and 5 CV water. The column was then equilibrated with 0.025 M sodium acetate, pH 6.3.

Whey (1500 ml), pH 6.3, was passed through the column at a flow rate of 4 ml/min (0.4× CV/min). The column was then washed with 0.025 M sodium acetate at pH 6.3 (2 CV). Bound proteins were sequentially eluted from the column with 0.4 M sodium acetate, pH 9.0; 0.7 M sodium acetate, pH 9.0; and 0.05 M trisodium phosphate with 0.5 M NaCl, pH 11.8. SDS-PAGE was conducted on the eluted proteins, as described above. The total protein was also determined for each eluted protein fraction, as described above.

The SDS-PAGE results indicated that the proteins eluted with 0.4 M sodium acetate (4 CV) consisted primarily of lactoperoxidase; the total protein was 87.3 mg.

The proteins that eluted with 0.7 M sodium acetate (3 CV) contained a mixture of lactoperoxidase, lactoferrin, and other minor whey proteins; the total protein was 24.7 mg. The proteins that eluted with 0.05 trisodium phosphate and 0.5 M NaCl primarily contained lactoferrin; the total protein was 121.1 mg.

Method 3.

As with Methods 1 and 2, in these experiments, "MACRO-PREP" High S (Bio-Rad) was packed in a 10 ml column (2.5 cm×2.1 cm), and reconditioned by passing 3 CV 0.5 M NaOH, 3 CV water, 3 CV 0.5 HCl, and 5 CV water. The column was then sequentially equilibrated with 0.025 M sodium acetate, pH 6.3.

Whey (1500 ml), pH 6.3, was passed through the column at a flow rate of 4 ml/min (0.4× CV/min). The bound proteins were sequentially eluted from the column with 0.1 M sodium acetate and 0.25 M NaCl, pH 9.0; 0.1 M sodium acetate and 0.5 M NaCl, pH 9.0; 0.7 M sodium acetate, pH 9.0; and 0.05 M trisodium phosphate and 0.5 M NaCl, pH 11.8. The eluted proteins were run on SDS-PAGE as described above.

The SDS-PAGE results indicated that the protein eluted with 0.1 M sodium acetate and 0.25 M NaCl (3 CV) was primarily lactoperoxidase; the total protein was 65.6 mg. The protein eluted with 0.1 M sodium acetate and 0.5 M NaCl (3 CV) was lactoferrin; the total protein was 43.2 mg. The protein eluted with 0.05 M trisodium phosphate and 0.5 M NaCl consisted primarily of lactoferrin; the total protein was 53.2 mg. No proteins were eluted with 0.7 M sodium acetate. With 0.1 M sodium acetate and 0.5 M NaCl, lactoferrin could not be completely eluted from the column. The remaining lactoferrin was eluted with 0.05 M trisodium phosphate and 0.5 M NaCl, pH 11.8.

Method 4.

As with Methods 1–3, in these experiments, "MACRO-PREP" High S (Bio-Rad) was packed in a 10 ml column (2.5 cm×2.1 cm), and reconditioned by passing 3 CV 0.5 M NaOH, 3 CV water, 3 CV 0.5 HCl, and 5 CV water. The column was then equilibrated with 0.025 M sodium acetate, pH 6.3.

Whey (1500 ml), pH 6.3, was passed through the column at a flow rate of 4 ml/min (0.4× CV/min). The bound proteins were sequentially eluted from the column with 0.1 M sodium acetate and 0.25 M NaCl, pH 8.0; 0.7 M sodium acetate, pH 7.5; and 0.05 M trisodium phosphate and 0.5 M NaCl, pH 11.8. The eluted proteins were run on SDS-PAGE as described above.

The protein that eluted with 0.1 M sodium acetate and 0.25 M NaCl (3 CV) was primarily lactoperoxidase; the total protein was 46.4 mg. The protein that eluted with 0.7 M sodium acetate primarily contained minor whey proteins; the total protein was 15.1 mg). The protein that eluted with 0.05 M trisodium phosphate and 0.5 M NaCl, was primarily lactoferrin; the total protein was 106.0 mg).

Method 5.

As with Methods 1–4, in these experiments, "MACRO-PREP" High S (Bio-Rad) was packed in a 10 ml column (2.5 cm×2.1 cm), and reconditioned by passing 3 CV 0.5 M NaOH, 3 CV water, 3 CV 0.5 HCl, and 5 CV water. The column was then equilibrated with 0.025 M sodium acetate, pH 6.3.

Whey (1500 ml), pH 6.3, was passed through the column at a flow rate of 4 ml/min (0.4× CV/min). The bound proteins were sequentially eluted from the column with 0.1 M sodium acetate and 0.25 M NaCl, pH 6.3; 0.7 M sodium acetate, pH 7.5; and 0.05 M trisodium phosphate and 0.5 M NaCl, pH 11.8. The eluted proteins were run on SDS-PAGE as described above.

The protein eluted with 0.1 M sodium acetate and 0.25 M NaCl (3 CV) was mainly lactoperoxidase; the total protein was 43.9 mg. Lactoperoxidase activity was confirmed using the pyrogallol and $H_2O_2$ procedure of Sigma. Briefly, the lactoperoxidase activity was tested using a slight modification of the Sigma method (Chance and Maehly, Meth. Enzymol., 2:773–775 [1955]). In the presence of lactoperoxidase (pH 6.0, 20° C.), $H_2O_2$ and pyrogallol (colorless) is converted to water and the colored compound purpurogallin. In this test, the reagents used were:

A. 100 mM potassium phosphate buffer, pH 6.0, at 20° C.;

B. 0.50% (w/w) hydrogen peroxide solution;

C. 5.0% (w/v) pyrogallol;

D. 0.1% (w/v) BSA solution; and

E. 0.1 M sodium acetate with 0.25 M NaCl, pH 6.3 eluted fraction or 0.05 M trisodium phosphate with 0.5 M NaCl, pH 11.8 eluted fraction (i.e., the fractions were tested separately for their lactoperoxidase activity);

F. The Reagent E fractions were separately heated in a boiling water bath for 10 minutes, in order to inactivate any lactoperoxidase activity in the sample.

Reagents B and C were prepared fresh prior to testing the enzyme activity. Test and blank samples were mixed separately, and the color change recorded. The test and blank samples included deionized water in dispensed one tube (2.1 ml) each (i.e., a test tube and a blank tube), reagent A (0.32 ml) in each of two additional tubes, 0.32 ml of pyrogallol (reagent C) in another set of two tubes, 0.10 ml reagent D (BSA) was added to one blank tube, and 0.10 ml Reagent E or F was added to one test tube.

In the test samples, color change was noted with 0.1 M sodium acetate with the 0.25 M NaCl, pH 6.3 fraction, indicating the presence of lactoperoxidase activity. When Reagent E was replaced with Reagent F, no color change was observed in the above fractions, indicating that the enzyme was inactivated during heating, confirming the presence of lactoperoxidase enzyme in the 0.1 M sodium acetate and 0.25 M NaCl, pH 6.3 fraction.

The fraction eluted with 0.05 M trisodium phosphate and 0.5 M NaCl, pH 11.8 buffer did not contain any lactoperoxidase. However, the protein present in the fraction coincided with the position of lactoferrin in the SDS-PAGE described above. These results further confirm the presence of lactoferrin in the 0.05 M trisodium phosphate and 0.5 M NaCl, pH 11.8 fraction.

The protein eluted with 0.7 M sodium acetate primarily contained minor whey proteins; the total protein was 17.5 mg. The protein eluted with 0.05 M trisodium phosphate and 0.5 M NaCl primarily consisted of lactoferrin; the total protein was 102.8 mg.

For elution of lactoperoxidase, 0.1 M sodium acetate and 0.25 M NaCl, with pHs ranging from 6.3 to 9.0 are equally suitable. However, since the enzyme is stable at about pH 6.3, Method 5 is the preferred method for isolating lactoferrin and lactoperoxidase. For elution of lactoferrin, 0.05 M trisodium phosphate and 0.5 M NaCl, pH 11.8, or any alkaline buffer with 0.5 M NaCl, may be used, as they were all found to be suitable.

As "MACRO-PREP" High S, at pH 6.3 to 6.6 mainly binds lactoperoxidase and lactoferrin in whey, this resin is suited for the isolation of lactoperoxidase and lactoferrin. It was also found that at least 150 bed volumes of whey can be processed through a column in a single process. Thus, at least 150 BVs can be continually processed (i.e., without a regeneration and/or cleaning).

EXAMPLE 12

Production of α-Lactalbumin-Enriched Whey (WPC) and β-Lactoglobulin From Whey

In this Example, methods were developed to remove β-lactoglobulin from bovine whey and prepare whey (WPC) enriched with α-lactalbumin.

Alpha lactalbumin is a major protein of human milk, making up 10–20% of the total protein. α-lactalbumin has been shown to be a component of lactose synthase, the enzyme responsible for lactose synthesis in the mammary gland. α-lactalbumin has very high nutritional value, and its amino acid composition appears to be very similar to the estimated amino acid requirement of newborns (See e.g., Lonnerdal and Atkinson, in Jensen (ed.), *Handbook of Milk Composition*, Academic Press, N.Y., [1995], at pp. 358–360). Thus, it may be desirable to include higher levels of α-lactalbumin in milk-based infant formulas, in order to provide a formula with an amino acid profile that similar to that received by breast-fed infants. Bovine milk contains a significantly lower amount of α-lactalbumin (1.2 g/L) than human milk (2.8 g/l), while human milk contains a negligible amount of β-lactoglobulin compared to bovine milk (3.2 g/L). Thus, methods are needed to increase the α-lactalbumin content and decrease the β-lactoglobulin content of bovine milk used in infant formula. This Example was designed to address the need to modify the composition of bovine milk used in infant formula so that it more closely approximates that of human milk.

As with previous Examples, various approaches were investigated in order to identify methods most suitable to obtain the goal(s) of the experiments. In this Example, eleven basic methods were tried.

Method 1.

In this method, "MACRO-PREP" High Q (Bio-Rad), a strong anion exchange support, was packed in a 10 ml column (2.5 cm×2.1 cm), and reconditioned by passing 0.5 M HCl (3 CV), water (3 CV), 0.5 M NaOH (3 CV), and water (5 CV). The column was equilibrated with 0.05 M sodium acetate, pH 6.3 (3 CV).

Whey (60 ml), pH 6.3, was passed through the column at a flow rate of 5 ml/min (0.5× CV/min). The column was then washed with 0.02 M sodium acetate, pH 6.3 (2 CV). Bound proteins were eluted from the column with 25 ml (2.5 CV) 0.7 M sodium acetate, pH 9.0, or 0.05 M sodium acetate and 0.5 M NaCl, pH 6.3, or 15 ml (1.5 CV) 0.1 M sodium acetate and 0.5 M NaCl, pH 4.0. Eluted proteins were monitored by UV detection at 280 nm (Isco UV Detector, Model 228), and the peaks were recorded on a chart recorder (linear). Volumes within the peak areas were pooled and further analyzed for protein content as well as by SDS-PAGE and Bio-CAD.

The protein eluted with 0.7 M sodium acetate or 0.05 M sodium acetate and 0.5 M NaCl, was primarily β-lactoglobulin, as observed by SDS-PAGE, conducted as described previously. No protein bands were detected in an SDS-PAGE gel containing the eluate in which 0.1 M sodium acetate and 0.5 M NaCl, pH 4.0 were used.

The total protein content in the 0.7 M sodium acetate or 0.05 M sodium acetate and 0.5 M NaCl fractions were approximately 200 mg, indicating that most of the β-lactoglobulin present in whey (60 ml) was bound to the column at pH 6.3, and was completely eluted with these buffers. The whey passed through the column was about 80% depleted of its β-lactoglobulin content, as observed by Bio-CAD (conducted as described previously). Thus, this whey was α-lactalbumin-enriched. It was determined that this 80% removal of β-lactoglobulin can be achieved when the resin to whey ratio is 1:6 (i.e., 10 ml resin and 60 ml whey). As described below, other ratios were also shown to work (e.g., Express-Ion Q, and SepraSorb-QM, etc.

Method 2.

In this method, as with Method 1, "MACRO-PREP" High Q (Bio-Rad), a strong anion exchange support, was packed in a 10 ml column (2.5 cm×2.1 cm), and reconditioned by passing 0.5 M 0.5 M HCl (3 CV), water (3 CV), 0.5 M NaOH (3 CV), and water (5 CV). The column was equilibrated with 0.05 M sodium acetate, pH 7.5 (3 CV).

Whey (60 ml), pH 7.5, was passed through the column at a flow rate of 5 ml/min (0.5× CV/min). The column was then washed with equilibration buffer. Bound proteins were eluted from the column with 30 ml (3 CV) of 0.7 M sodium acetate, pH 9.0. In addition, 20 ml (1.5 CV) 0.1 M sodium acetate and 0.5 M NaCl, pH 4.0, was passed through the column.

As observed by SDS-PAGE, the protein eluted with 0.7 M sodium acetate was primarily β-lactoglobulin. No protein bands were detected in eluate from 0.1 M sodium acetate and 0.5 M NaCl. However, a protein peak was eluted when 20 ml (1.5 CV) 0.1 M sodium acetate and 0.5 M NaCl, pH 4.0 were passed through the column. The process was continuously monitored by a UV detector and recorded, as described above. The total protein content of the 0.7 M sodium acetate fraction was 198 mg.

Method 3.

In this method, "MACROPREP" High Q (Bio-Rad) was packed and reconditioned as described in Method 1. The column was equilibrated with 0.025 M sodium acetate, pH 5.5. Whey (60 ml), pH 5.5, was passed through the column at a flow rate of 5 ml/min (0.5 CV/min). All of the other conditions were the same as described for Method 1.

It was found that the protein binding capacity was decreased at pH 5.5, as compared to the pHs tested in Methods 1 and 2. Only 125 mg protein was bound at this pH, while approximately 200 mg was bound at pH 6.3 (Method 1), and pH 7.5 (Method 2). It was also found that only 50% of the β-lactoglobulin was removed from the whey at pH 5.5, as whey passed through the column at pH 5.5 contained about 50% β-lactoglobulin, as determined by Bio-CAD. Thus, pH 5.5 may not be suitable for production of α-lactalbumin-enriched whey using Macro-Prep® High Q.
Method 4.

In this Method, all of the conditions described in Method 1 were used, except 40 ml whey, pH 6.6 was used (i.e., instead of 60 ml, as described in Method 1). The protein eluted with 0.7 M sodium acetate, pH 9.0 primarily contained β-lactoglobulin, as observed by SDS-PAGE. The total amounts of protein eluted (2 CV) with this buffer was 140 mg, indicating that most of the β-lactoglobulin in the whey was captured by the "MACROPREP" High Q medium (10 ml). The whey passed through the column had 90% less β-lactoglobulin, as observed by Bio-CAD. Thus, α-lactalbumin-enriched whey contained only 10% β-lactoglobulin.
Method 5.

In this Method, all of the conditions described in Method 1 were used, except the equilibration buffer was 0.1 M sodium phosphate, pH 6.3, and the amount of whey passed through the column was 40 ml, at pH 6.3. The protein binding capacity of the medium was found to be decreased, as only 89.0 mg of protein was bound, as compared to the 140 mg bound in Method 4, although the same amount of whey (40 ml) and the same approximate pH was used (i.e., 6.3 and 6.6). Thus, these results indicate that equilibration with 0.1 M sodium phosphate buffer (pH 6.3) may not be suitable for production of α-lactalbumin-enriched whey or WPC.
Method 6.

In this method, all of the conditions described in Method 1 were used, except the equilibration buffer was 0.05 M sodium phosphate, pH 6.3, and the amount of whey passed through the column was 40 ml, at pH 6.3. The protein binding capacity was found to be the same as that obtained with Method 4. The total amount of protein eluted with the elution buffer (2 CV) was 140 mg. The eluted protein mainly contained β-lactoglobulin, as observed by SDS-PAGE. Approximately 90% of the β-lactoglobulin was removed from the whey in this method, as the eluate contained only about 10% of the β-lactoglobulin of the starting whey, as determined by Bio-CAD.
Method 7.

In this method, all of the conditions described in Method 1 were used, except the equilibration buffer was 0.025 M sodium acetate, pH 6.3, and the amount of whey passed through the column was 40 ml, at pH 6.3. In addition, in some experiments, the whey was passed through the column in a single pass, while in other experiments, it was recirculated for 30 minutes, at a flow rate of 5 ml/min (0.5× CV/min).

In this method, the protein binding capacity was increased from 140 mg (Methods 4 and 6), to 165 mg. The bound protein was primarily [3-lactoglobulin, as observed by SDS-PAGE. It was also determined that more than 90% of the β-lactoglobulin was removed from the whey in this method. The whey passed through the column was enriched with α-lactalbumin, as most of the β-lactoglobulin bound to the resin. The production of α-lactalbumin-enriched whey (WPC) was confirmed by Bio-CAD and SDS-PAGE.

Although an understanding of the exact mechanisms are not necessary in order to use the present invention, the Ionic strength and pH appeared to play an important role during the process. The lower the ionic strength of the buffer, better binding kinetics of the β-lactoglobulin were observed.

These results indicated that the β-lactoglobulin binding capacity of the "MACROPREP" High Q resin was increased when the column was equilibrated with low ionic strength buffers (i.e., 0.05 M or lower), at pH 6.3 to 6.6 (Methods 1, 4, 6, and 7). Higher or lower pHs (i.e., below 6.3 and above 6.6), or higher ionic strength buffers (i.e., over 0.05 M), decreased the β-lactoglobulin binding capacity of the resin (Methods 2, 3, and 5). It was also found that the load volume of whey influenced the enrichment of α-lactalbumin in the whey. With a 6 CV load, at pH 6.3, enrichment of α-lactalbumin was 80% of the original whey, while with a 4 CV load (pH 6.3 or 6.6), enrichment of α-lactalbumin was increased to 90% (i.e., 90% of the composition).
Method 8.

In this method, Express-Ion Q (Whatman), a strong anion exchange support, was packed into a 100 ml Radial Flow Chromatography (RFC) column, and reconditioned by passing 0.5 M NaOH (2 CV), water (5 CV), 0.5M ICI (2 CV), and water (5 CV) through the column. The column was then equilibrated with 0.025 M sodium-acetate, pH 6.6 buffer (3 CV).

Whey (1200 ml), pH 6.6, was passed through the column at a flow rate of 40 ml/minute (0.4× CV/minute). Samples were collected from the pooled eluted fractions as: pooled 1–300 ml; 1–600 ml; 1–900 ml; and 1–1200 ml fractions. The column was then washed with 0.025 M sodium acetate, pH 6.6 (2 CV). The bound proteins were sequentially eluted from the column with 0.2 M sodium acetate-HCl, pH 3.5 with 0.5 M NaCl (2 CV), and 0.5 M HCl with 1 M NaCl (2 CV). The column was then cleaned with 0.5 M NaOH (2 CV). A large protein peak was eluted from the column with 0.2 M sodium-acetate-HCl, pH 3.5 with 0.5M NaCl. As determined by SDS-PAGE and Bio-CAD, the eluted protein was mostly β-lactoglobulin. No protein peak was observed with either 0.5M HCl and 1.0 M NaCl, or with the cleaning solution.

In addition, it was observed that approximately 97% and 94% of the β-lactoglobulin present in the whey was removed when the amounts of whey passed through the column were 300 ml (3 CV) and 600 ml (6 CV), respectively. When 900 ml (9 CV) and 1200 ml (12 CV) of the whey were passed through the column, the removal of β-lactoglobulin from the whey was approximately 72% and 59%, respectively.
Method 9.

In this method, SepraSorb QM (prepared according to the method of U.S. Pat. No. 5,492,723 to Sanderson et al., herein incorporated by reference), a strong anion exchange media was packed in a 100 ml RFC column, and reconditioned by passing 0.5 M NaOH (3 CV), water (5 CV), 0.5 M HCl (3 CV), and water (5 CV) through the column. The column was then equilibrated with 0.05 M sodium acetate, pH 6.6 (3 CV).

Whey (1200 ml), pH 6.6, was passed through the column at a flow rate of 40 ml/minute (0.4× CV/minute). Samples were collected from the pooled 1–300 ml, 1–600 ml, 1–900 ml and 1–1200 ml fractions. The column was then washed with 0.025 M sodium acetate, pH 6.6 (2 CV). Bound proteins were eluted with 5 CV of 0.2 M sodium-acetate-HCl, pH 3.5 and 0.5 M NaCl. The eluted protein was determined to be a mixture of β-lactoglobulin (80%) and α-lactalbumin (20%). Approximately 88% and 70% of the β-lactoglobulin present in the whey was removed when the amounts of whey passed through the column were 300 ml (3 CV) and 600 ml (6 CV), respectively. When 900 ml (9 CV) and 1200 ml (12 CV) whey were passed through the column, the removal of β-lactoglobulin from the whey was approximately 55% and 46%, respectively.

Method 10.

In this method, all the conditions described in Method 9 were used, except the equilibration buffer was 0.1 M sodium phosphate, pH 7.5. Whey (900 ml) at pH 7.5, was passed through the column at a flow rate of 40 ml per minute (0.4× CV/minute). Samples eluted from the column were collected from the pooled fractions of 1–300 ml, 1–600 ml, and 1–900 ml fractions. The column was then washed with 0.025 M sodium phosphate, pH 7.5 (2 CV). Bound protein was eluted with 5 CV of 0.1 M HCl+0.5 M NaCl. The eluted protein was a mixture of β-lactoglobulin (82%) and α-lactalbumin (18%). About 83% and 64% of the β-lactoglobulin present in the whey was removed when the amounts of whey passed through the column were 300 ml (3 CV) and 600 ml (6 CV), respectively. Approximately 55% of the β-lactoglobulin was removed when 900 ml (9 CV) whey was passed through the column.

Method 11.

In this method, all the conditions described in Method 9 were used, except the equilibration buffer was 0.05 M sodium acetate, pH 5.5 (3 CV). Whey (900 ml) at pH 5.5, was passed through the column at a flow rate of 40 ml per minute (0.4× CV/minute). Samples eluted from the column were collected from the pooled fractions of 1–300 ml, 1–600 ml, and 1–900 ml fractions. The column was then washed with 0.025 M sodium acetate, pH 5.5. Bound protein was eluted from the column with 0.2 M sodium acetate and 0.5 M NaCl, pH 3.5. The eluted protein was a mixture of β-lactoglobulin (66%) and α-lactalbumin (34%). About 55% of the β-lactoglobulin present in the whey was removed when 300 ml (3 CV) whey was passed through the column. About 100% β-lactoglobulin was present in the whey when 600 ml (6 CV) of the whey was passed at pH 5.5. While these results indicate that the removal of β-lactoglobulin was very efficient with Sepra-Sorb-QM, at pH 6.6 or 7.5, but at pH 5.5, SepraSorb QM, may not be as suitable for removal of β-lactoglobulin from whey (See, Methods 9 and 10).

EXAMPLE 13

Preparation of Monolithic Ion-Exchange Media

In this Example, columns containing monolithic ion-exchange media were prepared so that they could be used to separate whey proteins.

A. Preparation of CM—"SepraSorb®

Absorbent medium prepared according to the methods of U.S. Pat. No. 5,492,723 (herein incorporated by reference) was prepared in sheets. Sheets of this medium referred to as "CM-SEPRASORB" were cut into circular discs (2.5 cm×0.5 cm) and stacked (10~12 discs) into columns (2.5 cm×5 cm). In this example, the columns had approximate bed volumes of 25 mL and the ion-exchange discs had 85% void porosity. The membrane pore size ranged from 50 to 300 mm. "SEPRASORB" ion-exchange sheets were also packed spirally in a Radial Flow Column (10 cm×3.3 cm) with an approximate bed volume of 100 mL. Columns were stored at 4° C. until use.

B. Preparation of "DE-SEPRASORB" Column Material

The DE-"SEPRASORB" column material was produced by washing sheets (15 cm×25 cm) of high voidage filtration media (HVFM; Spontex, ASG3 #45220000, also referred to as "sponge cloth" by the manufacturer) as described in the 5,492,723 Patent. Briefly, sheets of the medium were washed in tap water at 40–50° C. to remove any residual fungicide. Each sheet was twice rinsed thoroughly, with squeezing in distilled (deionized) water. The material was then squeezed by hand or rollers until dry (i.e., until the material did not drip water). The material was then either vacuum packed for storage at 4° C. for later use, or processed further as described below.

The washed and dried sheets of HVFM were then cross-linked for DE derivatization. This step involved mixing 0.8 M NaOH and 0.8% dichlorohydrin (1,3-dichloro-2-propanol)(DCH). For 6 sheets (1.16 L media), 10.4 ml DCH was added to 1300 mL 0.8 M NaOH immediately prior to use and mixed. Each sheet of material was placed in a glass tray and 215 mL of the mixture was added. A roller was used to evenly distribute the mixture through the sheets. The trays were covered with four (4) layers of non-polyvinyl chloride (PVC) cling film, and placed in a microwave oven. The sheets were heated for 75 seconds on "High," and then removed from the microwave and covered with aluminum foil. The foil-covered sheets were placed in a preheated conventional oven with an extraction component. The sheets were heated for 60 minutes at 100° C., removed from the oven and washed as described below.

First, the sheets were squeezed in a fume hood and the waste mixture discarded. The sheets were then washed in water twice, using fresh water for each wash. The sheets were thoroughly squeezed. Each sheet was then placed between two sheets of unprocessed, clean HVFM and allowed to dry until no water dripped from the sheets. If necessary, the sheets placed between the clean HVFM were passed through rollers. These washed sheets can be stored at 4° C., if necessary.

Next, the washed sheets were derivatized with DE. First, water and DEAE were combined to make a mixture. For 6 sheets of material, 166 g DEAE (diethylaminomethylchloride hydrochloride) was added to 336 mL (room temperature) water. Each sheet was placed in a glass tray and 63 mL of the water and DEAE mixture were added. A roller was used to evenly apply the mixture to each sheet. Next, each soaked sheet was placed in a glass tray containing 125 mL 5 M NaOH (room temperature). The sheet was soaked gently in the NaOH, without rolling. The tray was covered with non-PVC cling film and a layer of aluminum foil. The tray was placed in a pre-heated conventional oven, with extraction to remove any fumes produced during heating. The tray was incubated for 60 minutes at 100° C. The tray was removed from the oven and the sheet was squeezed dry. The sheets were then washed as described in the previous paragraph. This process (through the washing steps) was then repeated. Following the second round of DE derivatization, the cross-linked material was ready for use as "DE-SEPRASORB" material.

EXAMPLE 14

Preparation of WPI, α-Lactalbumin, and β-Lactoglobulin

In this Example, WPI, α-lactalbumin, and β-lactoglobulin were produced, using "CM-SEPRASORB" (i.e.,a weak acid cation exchange column), and "DE-SEPRASORB" (i.e., a weak acid anion exchange column), prepared as described in the previous Example.

Figure 7:
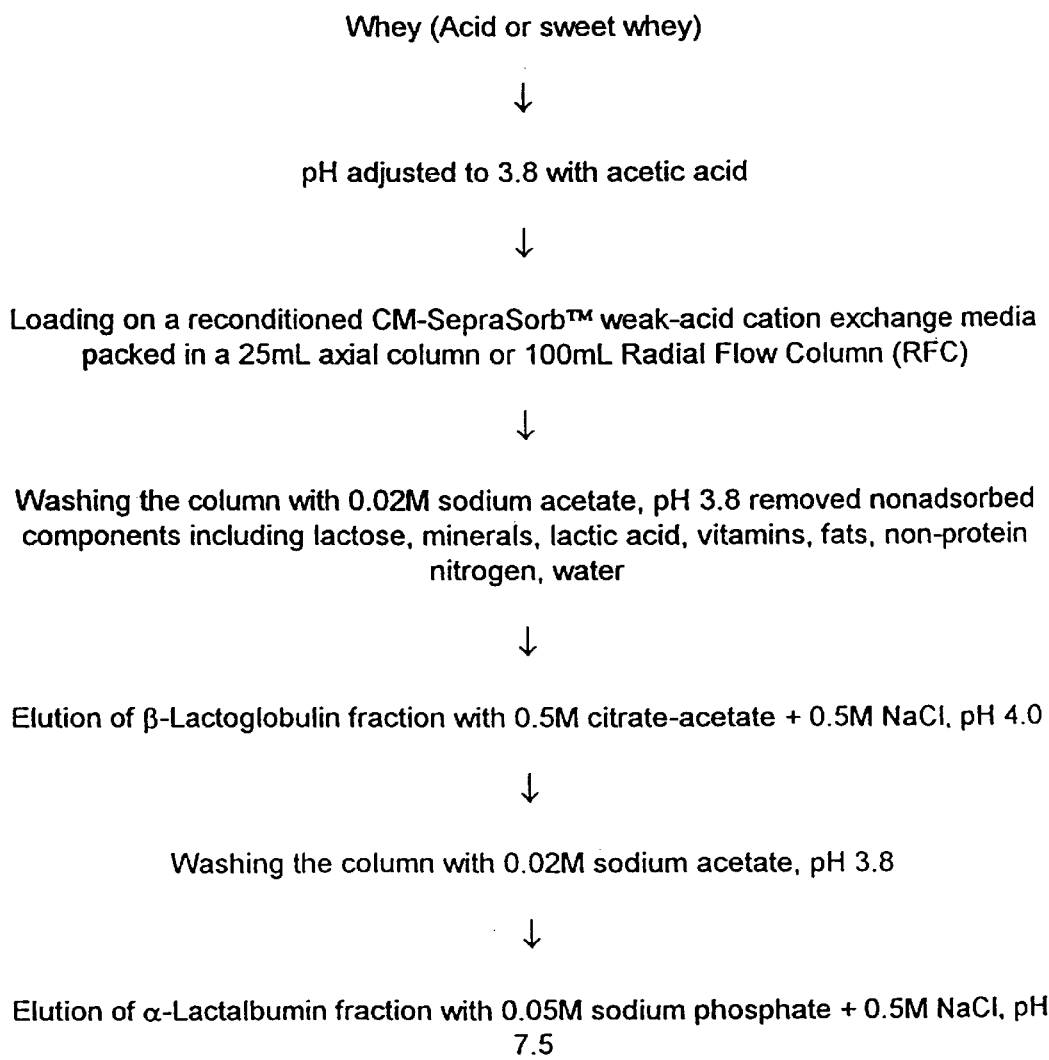
FIG. 7 is a flow chart showing the fractionation of α-lactalbumin and β-lactoglobulin from whey.
Figure 8:
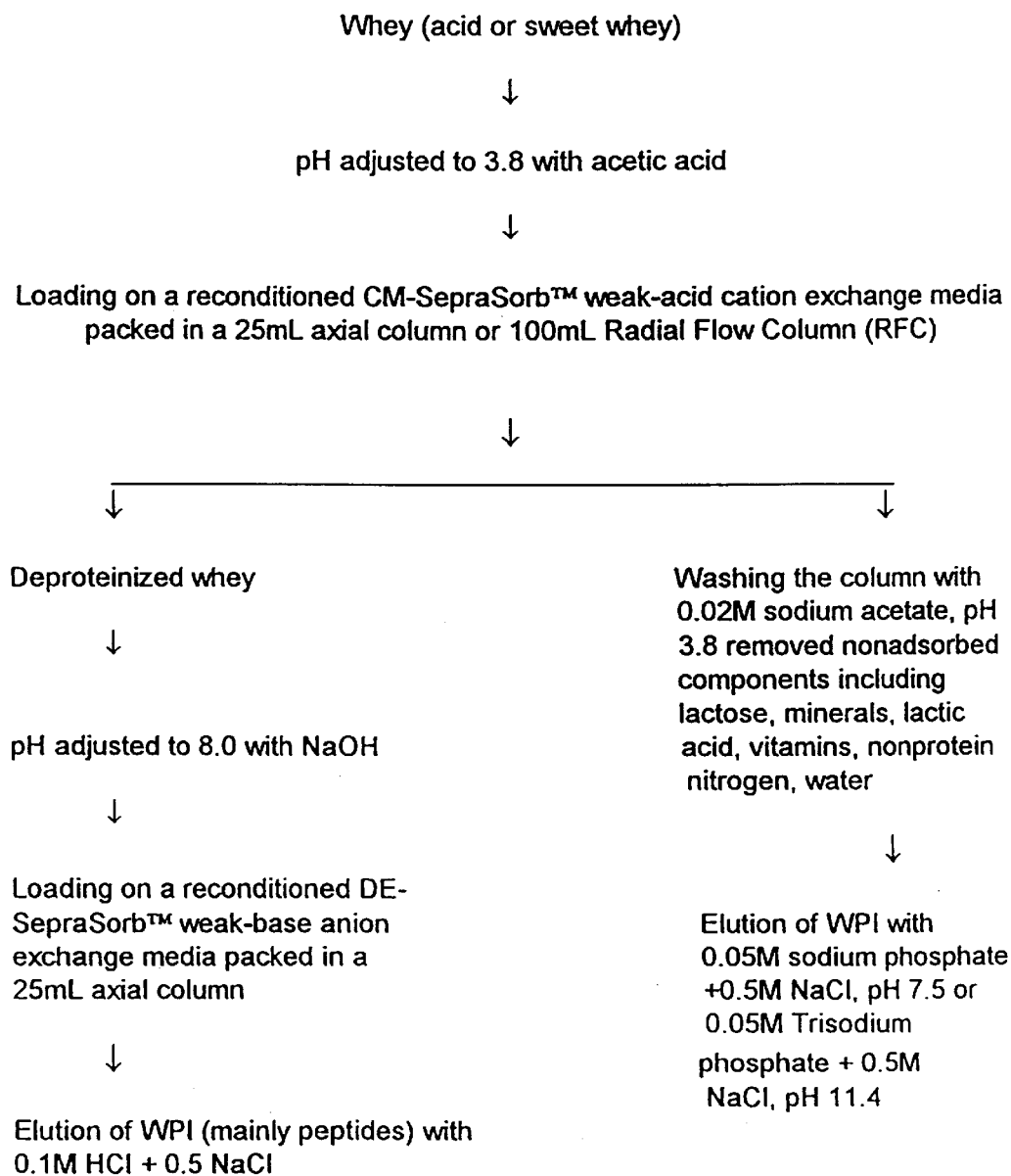
FIG. 8 is a flow chart showing one embodiment for the production of WPI from whey.
Figure 9:
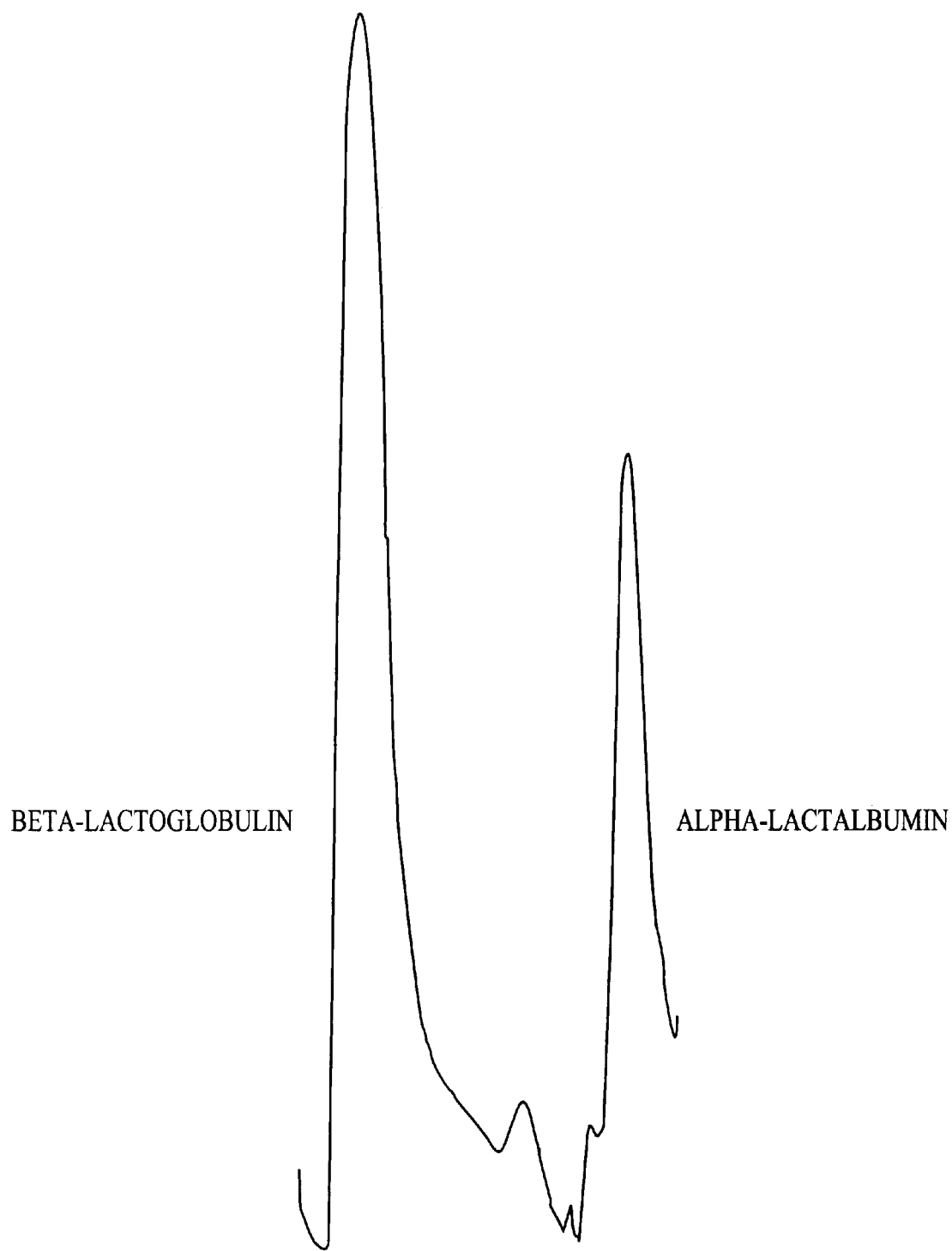
FIG. 9 shows the elution profile of α-lactalbumin and β-lactoglobulin from the "CM-SEPRASORB" ion-exchange column.

FIG. 7 is a flow chart which shows the one embodiment for the fractionation of α-lactalbumin and β-lactoglobulin from whey. FIG. 8 shows one embodiment for the production of WPI from whey. FIG. 9 shows the elution profile of α-lactalbumin, and β-lactoglobulin from the "CM-SEPRASORB" ion-exchange column at 280 nm. The protein isolation cycle consisted of reconditioning, loading, washing, elution and cleaning the columns.

CM-SepraSorb®

For each run with "CM-SEPRASORB" the column was reconditioned by sequentially passing 4 bed volumes of 0.5 M NaOH, 8 bed volumes of distilled water, 4 bed volumes of 0.5 M HCl, and 8 bed volumes of distilled water. All steps were carried out at a constant flow rate of 0.5 column volumes per minute, using a peristaltic pump. The column was equilibrated with 0.05 M sodium acetate, pH3.8.

Raw whey (150 mL), whey diluted with water (2 to 4 times diluted), whey dialyzed against water, or demineralized whey was prepared and the pH adjusted to 3.8. The whey samples used in this Example were composed of mozzarella whey (Le Prino Foods), as well as gouda cheese whey (Domo Foods, Beilen, Netherlands).

The whey sample was loaded into A 2.5 cm×5 cm column, with a total protein in the load of 1000~1200 mg (Kjeldahl nitrogen estimation method; See e.g., R. L. Bradley et al., "Chemical and Physical Methods, 15.1 Proteins," in R. T. Marshall (ed.), *Standard Methods for the Examination of Dairy Products*, American Public Health Association, [1992], pp.504–516). The whey was either passed or recirculated at a flow rate of 0.5× column volume/min. for 60 min. Most of the true proteins present in whey (e.g., α-lactalbumin,-β-lactoglobulin, bovine serum albumin, lactoferrin, and immunoglobulins) were bound to the discs. The column was washed with 0.02 M sodium acetate, pH 3.8 (4 bed volumes) to remove unbound materials from the media.

The protein fraction enriched with β-lactoglobulin was eluted with 0.5 M citrate-acetate containing 0.5 M NaCl, pH 4.0 (3 bed volumes). The column was again washed with 0.02 M sodium acetate, pH 3.8 (4 bed volumes). The protein fraction enriched with α-lactalbumin was eluted with 0.05 M sodium phosphate containing 0.5 M NaCl, pH 7.5 (3 bed volumes). The elution of protein from the column was monitored using a UV monitor (ISCO, model 228) connected at the outlet of the column and elution peaks were recorded with a chart recorder. The "CM-SEPRASORB" discs were cleaned by passing 0.5 M NaOH containing 1 M NaCl through the column. The column was then regenerated as described above.

Production of WPI and fractionation of α-lactalbumin and β-lactoglobulin from whey was also achieved using a RFC (bed volume 100 mL) packed with "CM-SEPRASORB" ion-exchange media.

Total WPI was eluted from the above media using 0.05 M sodium phosphate containing 0.5 M NaCl, pH 7.5 or 0.5 M trisodium phosphate containing 0.5 M NaCl, pH 11.4. Recovery of the protein from the "CM-SEPRASORB" media was 53 to 66%, depending upon pretreatment conducted on the whey. For example, whey that was diluted 4 times in water (i.e., a four-fold dilution of whey) resulted in the recovery of 66% of the protein, compared to the protein recovery value of 56% obtained with raw whey, although total amount of protein passed through the column was same for both cases. On the other hand, dialyzed whey gave 73% protein recovery from the "CM-SEPRASORB" media.

Deproteinized whey eluted from the "CM-SEPRASORB" column, pH was adjusted to 8.0 with NaOH, recirculated through a 2.5 cm×5 cm "DE-SEPRASORB" column for 60 min. at a flow rate of 0.5 column volume/min. Bound proteins were eluted with 0.1 M HCl containing 0.5 M NaCl. DE-discs mainly captured small peptides from the deproteinized whey. However, when raw whey was recirculated at pH 8.0 as above, other major proteins were also bound to DE-media.

"DE-SEPRASORB"

The "DE-SEPRASORB" ion-exchange media was reconditioned prior to its use by passing 4 bed volumes of 0.5 M HCl, 8 bed volumes of distilled water, 4 bed volumes of 0.5 M NaOH and 8 bed volumes of distilled water through it at a flow rate of 0.5 column volumes per min. The column was then equilibrated with 0.1 M sodium phosphate, pH 8.0.

Total recovery of the proteins from the combined CM- and DE- columns was approximately 80~97%, depending upon pretreatment steps conducted on the whey. For example, whey diluted four-fold in water gave an 80% protein recovery compared to 97% recovery when dialyzed whey was used.

Comparison with Other Methods

Girardet et. al. (Girardet et al., Milehwissensehatt 44:692–696[1989]) reported separation of different whey proteins by anion exchange FPLC. However, in this reference a mixture of pure whey proteins was used, in contrast to the raw whey used in this Example. Girardet et al. prepared the whey proteins using ammonium sulfate precipitation method and dialyzed the proteins to remove lactose, minerals, salts and small peptides. Thus, unlike the present invention which utilizes raw whey (i.e., an impure mixture), Girardet et al. describe an FPLC method for separating individual proteins present in a mixture of pure whey proteins.

In raw whey, proteins are present as micelles. In addition, lactose, minerals, vitamins, fats and small peptides have profound effect on binding kinetics on the ion-exchange media as well as fractionation of proteins. Also, the FPLC column was packed with small ion-exchange beads that runs under high pressure. Thus, the FPLC method of Girardet et al. cannot be used nor modified for use, in a large scale process chromatography system, where back-pressure of the column must be kept low to keep cost down.

In addition, Zietlow and Etzel (J. Liquid Chromatogr., 1001–1018 [1995]) reported attempts to isolate whey proteins using a sulfopropyl ion-exchange membrane (BPS Separations, Ltd. Spennymoor, County Durham, UK) cartridge. However, they found that loading raw whey directly onto the cartridge created a rapid pressure increase. For that reason, they microfiltered the raw whey using 0.45 mm polysulfone hollow-fiber membrane prior to loading into the cartridge. Prefiltration of whey not only decreased total yield of protein (e.g., 30% of the total protein content was lost during the microfiltration process), it also increased the cost of the process.

As illustrated in the above Examples, raw whey can be processed through the monolithic SEPRASORB® ion-exchange media without any pretreatment. Furthermore, SepraSorb® ion-exchange media described in this application were designed to overcome limitations encountered in commercial ion-exchange processes utilizing beads, UF, or MF technology for the isolation and fractionation of whey proteins. For "SEPRASORB" ion-exchange media, intra-bead diffusional limitation was found to be negligible.

Consequently, use of "SEPRASORB" media eliminates the mass transfer and flow limitations associated with bead-based processes and allow the separation systems to approach local equilibrium behavior. Based on these

TABLE 11

Composition of Whey Protein Isolate (WPI) and Major Individual Proteins (IPS)*

| Product | Protein (%) | Fat (%) | Ash (%) | Lactose (%) | Moisture (%) | Protein Sub-Units (HPLC)** | | | |
|---|---|---|---|---|---|---|---|---|---|
| | | | | | | β-Lac (%) | α-Lac. (%) | BSA (%) | IgG (%) |
| WPI (high fat) | 90.5 | 1.2 | 1.8 | <1.0 | 4.3 | 48.85 | 36.14 | 3.55 | 6.56 |
| WPI (low fat) | 91.0 | 0.4 | 1.7 | <1.0 | 4.2 | 47.63 | 35.93 | 3.29 | 6.01 |
| α-Lac | 90.7 | 0.2 | 2.0 | <1.0 | 5.9 | 5.76 | 81.19 | 7.77 | 4.36 |
| β-Lac | 91.0 | 0.4 | 1.6 | <1.0 | 5.2 | 86.65 | 7.93 | o | 4.17 |

\* = Powder samples from pilot production using 50 L RFC column, at 350 L cheddar cheese whey loaded per cycle. Protein fractions were UF concentrated and then spray dried using a Niro spray drier.
\*\* = See, FIGS. 10–13 (Chromatograms)
β = β-lactoglobulin
α = α-lactalbumin considerations, monolithic SepraSorb® ion-exchange media represents an efficient and economical method for isolation and fractionation of whey proteins that is superior to the methods presently in use.

EXAMPLE 15

Cheddar Cheese Whey Protein Isolate Composition

In this Example, an RFC column packed with "MACRO-PREP" S resin as described in Example 1, was used to determine the composition and major individual proteins in cheddar cheese whey. Cheddar cheese is made from whole milk (i.e., relatively high fat whey). In contrast, mozzarella is drained from curding of skim milk (i.e., low fat whey). Thus, it was of interest to determine the differences in whey protein separation using cheeses with these differing histories.

In this Example, the 50 liter RFC column was packed with "MACRO-PREP" S resin. Cheddar cheese whey (Land O' Lakes), was loaded to the column at a load of 350 liters per cycle (i.e., 7 column volumes). The column was run as described in Example 2.

Protein fractions obtained from this sample were UF concentrated 10-fold, through a 5000 molecular weight cut-off membranes, diafiltered with water at a volume of 5 times the volume of ultrafiltrate. The protein contained in the liquid solution was spray dried using a Niro spray dryer (Hudson, Wis.). The protein sub-units were analyzed by size-exclusion chromatography with HPLC.

Figure 10:
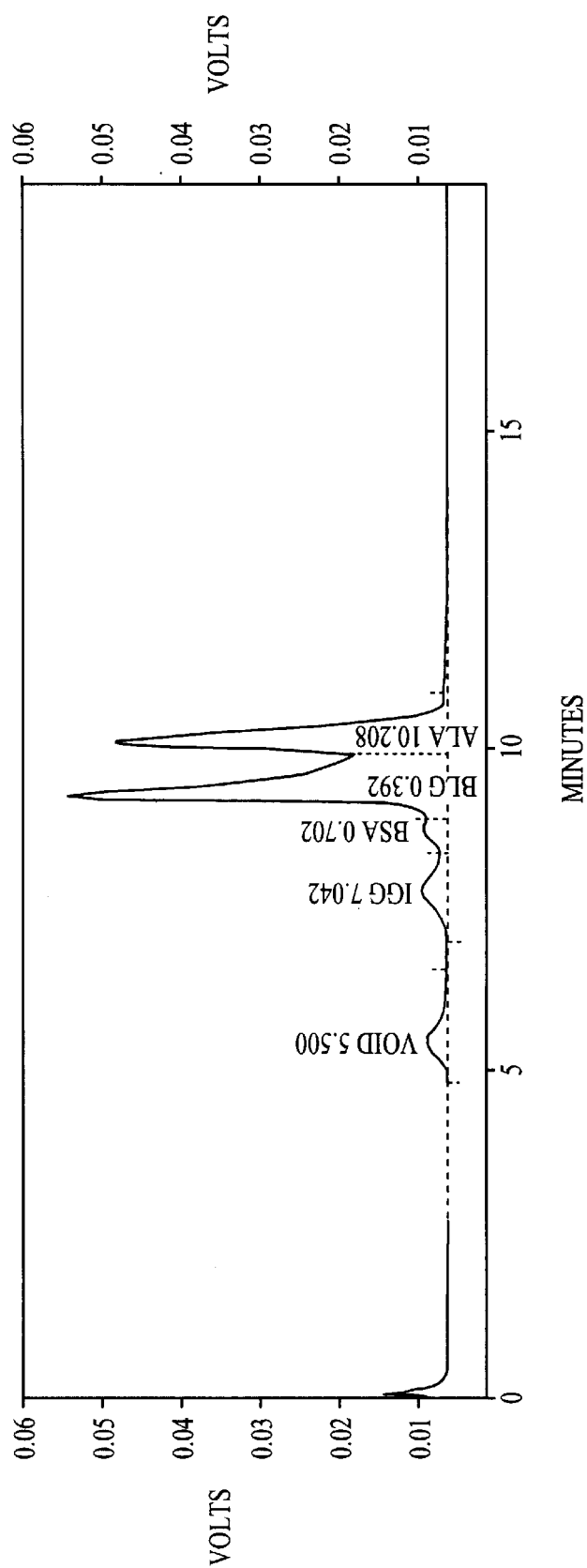
FIG. 10 is a chromatogram obtained from high fat WPI.
Figure 11:
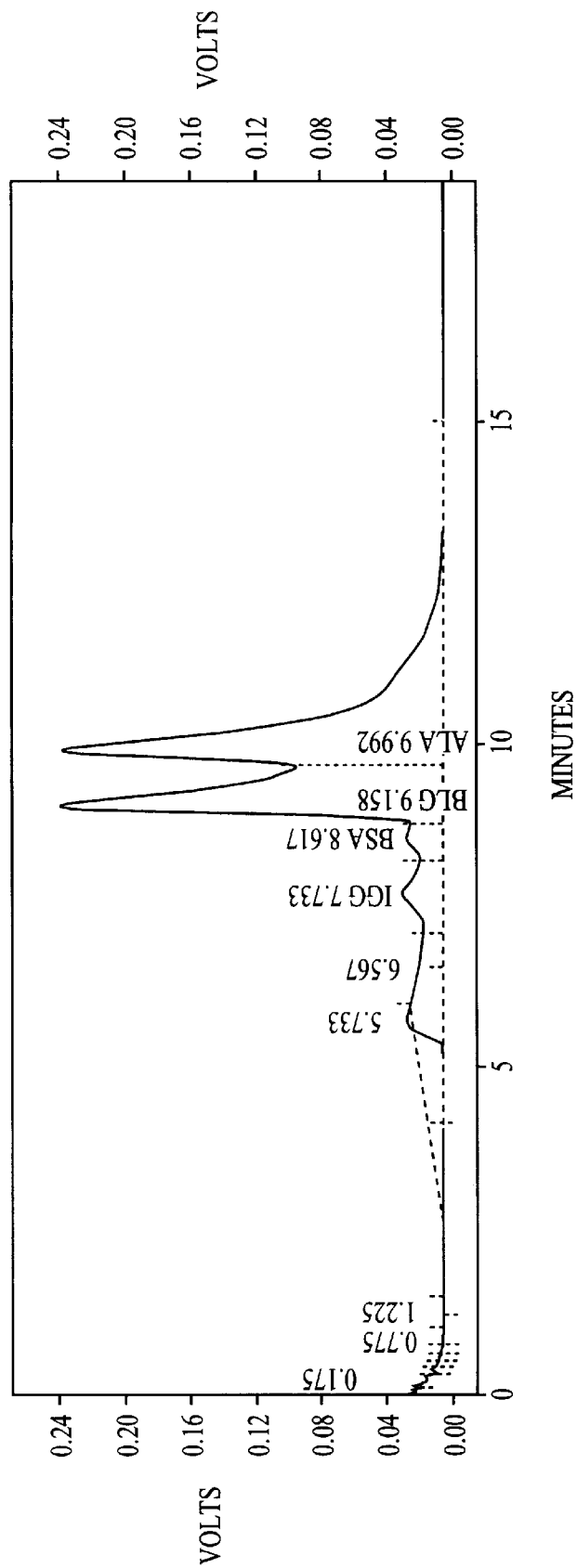
FIG. 11 is a chromatogram obtained from low fat WPI.
Figure 12:
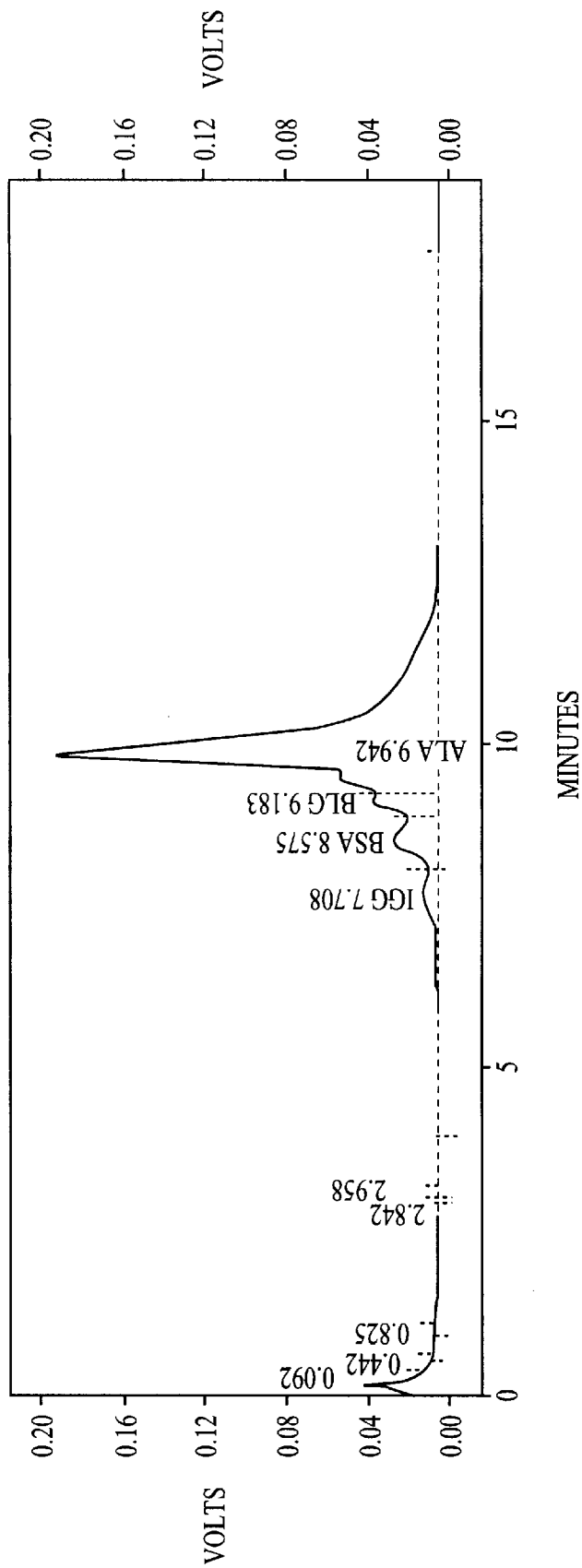
FIG. 12 is a chromatogram obtained from α-lactalbumin.
Figure 13:
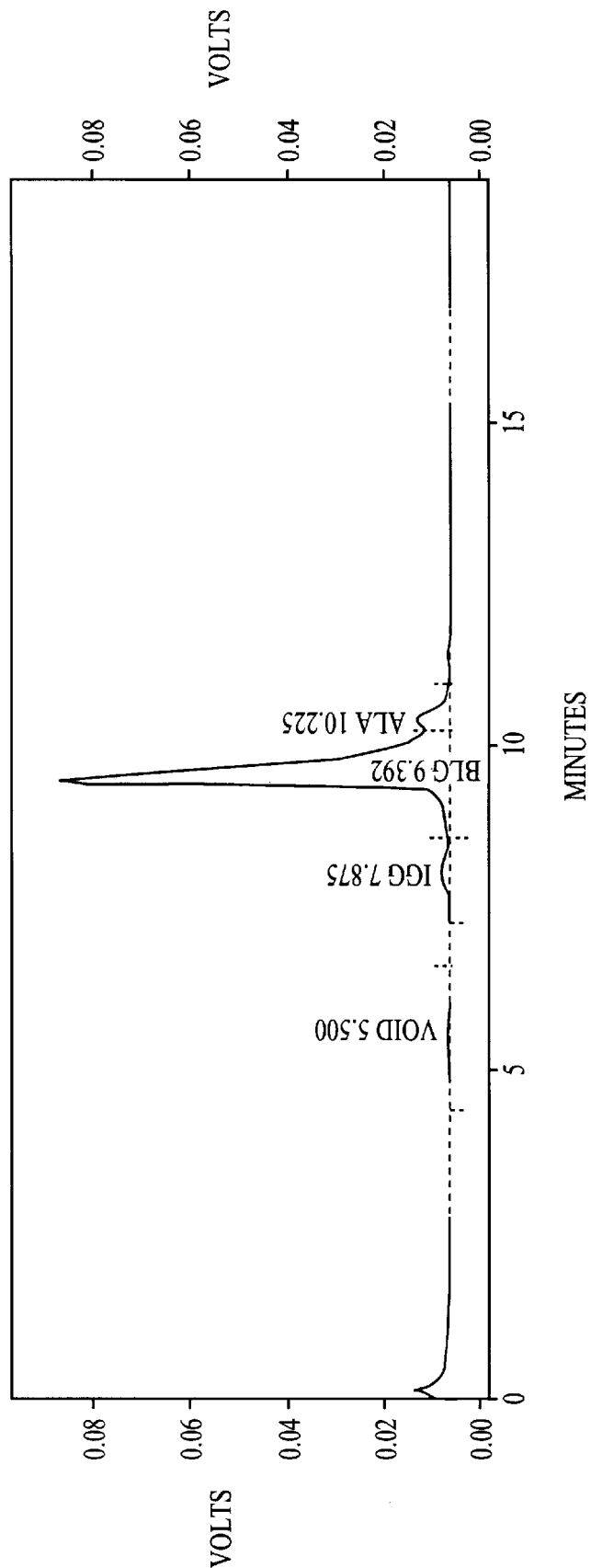
FIG. 13 is a chromatogram obtained from β-lactoglobulin.

Table 11 below, shows the compositions of the whey protein isolate and the percentage of the protein subunits for high and low fat WPI, as well as α-lactalbumin and β-lactoglobulin. In this Figure, the lowfat WPI (a clear product), was eluted using 250 liters of 0.2 M sodium acetate-acetic acid and 0.1 M sodium chloride solution (pH 5.0). High fat WPI (a cloudy solution) was eluted using 0.05 M sodium phosphate and 0.5 M sodium chloride (pH 9.0). Approximately 250 liters were used to elute the columns. FIGS. 10-13 show chromatograms obtained from the HPLC analyses of the protein subunits. FIG. 10 shows the chromatogram for high fat WPI, while FIG. 11 shows the chromatogram for low fat WPI, FIG. 12 shows the results for α-lactalbumin, and FIG. 13 shows the results for β-lactoglobulin.

In addition, the whey protein fractions or the separated and purified proteins and the non-proteinaceous eluants may be incorporated into dietary and pharmaceutical formulations in appropriate proportions. Such formulations include but are not limited to infant formulas, fat substitutes, foaming agents, egg white substitutes, animal feed substitutes and the like.

EXAMPLE 16

An Alternative Method for Separating Whey Proteins

In this Example, the processing steps, buffers, media, and pH adjustment of the whey as described in Example 1 were used. However, the RFC column of Example I was replaced with a 2000 ml beaker with a raised stirring rod. This beaker was used on a mixing plate.

The media (250 g of "MACRO-PREP" S cation exchange resin) was placed in the beaker, cleaned, regenerated, and then equilibrated by adding 500 mls of each solution as described in Example 1, with an approximately 800 ml distilled water wash between the steps as appropriate. The equilibrated resin was then mixed at low speed for 8 minutes. The media was allowed to settle for 10 minutes, and the liquid was carefully pumped out of the beaker.

Next, 1750 mls of mozzarella cheese whey (pH 3.8) was added to the equilibrated and drained medium. The whey and resin were mixed at low speed for approximately 18 minutes. The mixing was then stopped and the media with adsorbed protein was allowed to settle. The deproteinized whey was then carefully pumped out of the beaker from the top.

The deproteinized whey was then washed out from the bed resin with distilled water as described above, in order to bring the UV baseline to <10% of the original reading. This was done in three steps, using 550 mls of water to wash the sample each time, with a total of approximately 38 minutes being required to complete the washing.

Elution of the β-lactoglobulin, α-lactalbumin, BSA, and lactoferrin fractions was conducted using the same method as described in Example 1. In this elution, 1000 mls, 900 mls, 900 mls. and 700 mls of elution buffer were used, respectively for each of these proteins, in addition to two 500 ml water washes. Finally, the medium was cleaned and regenerated as described in Example 1, with approximately 15 minutes being required to complete the process.

Analyses of samples from the steps in this method showed that similar results were obtained using this method as with the method described in Example 1. This process can be completed at large-scale. However, depending upon the space and installation requirements, it may be unpractical. In addition, the length of time required for each cycle may be too long to provide economic benefit.

EXAMPLE 17

Separation of Cloudy and Clear Whey Protein Isolates (WPI)

In this Example, methods for separation of cloudy and clear WPI were established. The fat residues remaining in whey following clarification and centrifugation are primarily composed of glycerides and phospholipids. These fat residues are the main contributor to the cloudiness observed in whey and whey products. Using current processes for whey protein concentrate (WPC) and WPI from whey, the lipids are totally (WPC) and partially (WPI) separated with the protein portions. Therefore, a wide range of fat content can be expected in dehydrated whey protein compositions, depending upon the level of concentration. For example, WPC 35 (i.e., WPC containing 35% total protein on a dry basis), may contain 2–3% total fat, while WPC 80 may contain 7–8% total fat, and WPI may contain 0.5–1.0% total fat, depending upon the protein concentration of the finished product. During UF concentration of whey or fractionated whey, proteins and fat are both retained in the concentrate, while molecules with weights less than the cut-off of the UF membrane pore size pass through the membrane, along with water, to produce a permeate. Therefore, in relative terms, the higher the protein level in the finished product, a high the fat content is also expected.

In addition to the cloudy appearance of formulations containing whey or whey proteins, fat also contributes a dairy note and flavor to these products. Although the cloudiness due to fat may be desirable in some food applications, it often limits the use of the product. To expand the utilization of WPI in areas beyond conventional applications (e.g., clear and/or flavor-sensitive beverages, health foods, nutritional supplements, feeds, etc.), methods to produce clear (<0.4% fat on a dry basis) were developed, along with cloudy WPI ($\geq 0.5\%$ fat on a dry basis).

Preparations of cloudy (i.e., regular) WPI and clear WPI were tested (these samples were all non-colored whey which eluted fractions from RFC columns; these fractions were not ultrafiltered) to determine the OD reading (absorbance) at 600 nm. For regular WPI (i.e., cloudy WPI), the $OD_{600}$ ranged from 1.793 to 1.246. For clear WPI, the $OD_{600}$ ranged from 0.184 to 0.205. Thus, it is evident that there are visual and objective assessments that are useful in identifying clear WPI.

Production of Cloudy WPI

A 50 L RFC column was packed with "MACROPREP" S resin and conditioned as previously described. The column was equilibrated with 0.020 M sodium acetate (trihydrate), pH 3.6 to 3.8 (1 to 3 CVs), at 0.4–0.6 CV/min. The pH of the flow through was monitored, in order to assure that it was less than 4.0. The flow rate was adjusted to 0.4 CV/min. In some cases, equilibration may not be necessary (e.g., when the resin bed is generated, washed, and free of chemical residues, as well as when more than 7 CV of whey [i.e., diluted whey] is loaded onto the column). Whey, pH 3.8 (7 CV) was loaded and passed through the column at 0.4–0.5 ° CV/min. The first CV was discarded or circulated (i.e., returned to the whey feed tank used to load the column), and the next 6 CVs were collected. All of the proteins were adsorbed to the resin, and the non-protein components, were passed with the flow through (i.e., "deproteinized whey"). The whey used in this method may be either clarified, separated, single strength sweet acidic whey, or 3–5× UF-concentrated whey that has been HTST pasteurized and chilled (5–10° C.), although warm (40–50° C.) whey may also be used. Pretreatment of the whey (e.g., microfiltration to reduce butterfat, or demineralization to reduce the ash content) may improve the efficiency of the resin, although it is not a requirement for the separation process. During the development of the present methods, it was determined that WPC did not provide any capacity advantages over single-strength whey, as the capacity of the resin is fixed, and adsorption is likely to be more efficient for whey with a lower viscosity. However, it may provide processing benefits in that the volume of whey necessary may be decreased through the use of these methods.

The resin bed was washed with water (1–2 CV), to remove entrapped deproteinized whey. The first CV was collected and added to the previously collected 6 CVs of deproteinized whey; the second CV of the wash was discarded. The whey protein (WPI) bound to the column was eluted with 2–3 CVs of the WPI elution buffer, at 0.4 CV/min. The first CV was discarded, while the last two CVs were collected. Then, 1–2 CVs of water were passed through the column. The first CV was collected and added to the previously collected 2 CVs of the eluted WPI fraction. The resin bed was then cleaned with 2 CVs of the regeneration base solution. The first CV was discarded and the flow through from the second CV was circulated. The column was then rinsed with 3–4 CVs water to remove caustic residue. The first CV was recycled back to the tank containing caustic material, and the second CV was discarded. After equilibration (as described above), the column was ready to process the next cycle of whey.

At the end of each processing day, the column was cleaned with regeneration acid solution after rinsing the column following the application of regeneration base solution. Water was then used to wash the column and remove acidic residue. The column was then equilibrated. After the removal of peptides by ultrafiltration, the deproteinized whey from one cycle may be used for equilibration of the column prior to the next processing cycle.

The following Table provides the buffer volumes and formulae used (for a CV of 50 L,). The amount of HCl required is dependent upon the water quality and the initial pH of the whey. The regeneration acid solution may be used once per day, or once per week, depending upon the feed (i.e., load), and number of cycles processed per day. The regeneration base solution may be used during each cycle, every fifth cycle, or once per day, depending upon the whey feed, and number of cycles processed. The "NA" in this Table indicates that the pH is not applicable. Depending upon the cost and availability of reagents, acetic acid, hydrochloric acid, phosphoric acid, or sulfuric acid may be used as the equilibration buffer (0.5 M). In addition, a non-phosphate buffer containing sodium acetate (0.03 M), NaCl (0.5 M), and NaOH (0.004), at pH 8–10 may be used as the WPI eluent buffer.

TABLE XX

Buffer Volumes and Formulae

| No. | Buffer/ Solution | Est. Required CV/Cycle | Expected Final pH | Estimated Required Chemicals/Cycle | | | | |
|---|---|---|---|---|---|---|---|---|
| | | | | Sodium Acetate | Sodium Phosphate Dibasic | NaCl | NaOH | HCl |
| 1 | Equilibration Buffer | 3 | 3.8 | 1.02 kg | | | | .4–.6 L |
| 2 | WPI Eluent Buffer | 3 | ≈8.8 | | 1.05 kg | 4.35 kg | | |
| 3 | Regeneration Base Solution | 2 | ≈11.5 | | | | 2.0 kg | |
| 4 | Regeneration Acid Solution | 2 | <2 | | | | | 0.036 L |
| 5 | Whey | 7 | 3.8 | | | | | .3–.8 L |
| 6 | Packing Solution | 3 | NA | | | 4.38 kg | | |

NA = Not Applicable

Production of Clear WPI

As above, a 50 L RFC column packed with "MACRO-PREP" S was used in these experiments. The same whey preparations as described above were also used. Unless otherwise indicated, the same buffers were used as described in the production of cloudy WPI.

The column was packed with resin and equilibrated with 1–3 CVs of equilibration buffer at 0.4–06 CVs/min, as described above. The whey was loaded and passed through the column, and the column was washed as described above. The WPI fraction was eluted with 2–3 CVs clear WPI elution buffer (0.1–0.2 M sodium acetate with 0.1 to 0.5 M NaCl, pH 5.0–5.6), at 0.4 CV/min. The first CV was discarded and the last 2 CVs of the eluted fraction were collected. Then, 1–2 CVs water were passed through the column. The first CV was collected and added to the collected 2 CVs of the eluted WPI fraction. The BSA and fat were then eluted with 2 CVs of BSA elution buffer (0.025 M sodium phosphate and 0.1–0.3 M sodium chloride) at 0.4 CV/min. The first CV was discarded and the last CV was collected. The BSA elution buffer composed of sodium acetate (0.05 M), citrate (0.05 M), and NaCl (0.5 M), pH 8.0–10.0 may also be used. The resin was then cleaned with 2 CVs of regeneration base solution. The first CV was discarded and the flow through of the second CV was circulated back into the tank containing regeneration buffer. The column was then rinsed with 3–4 CVs water to remove caustic residue as described above. After equilibration (as described above), the column was ready to process the next cycle of whey.

At the end of each processing day, the column was cleaned with regeneration acid solution after rinsing the column following the application of regeneration base solution. Water was then used to wash the column and remove acidic residue. The column was then equilibrated. After the removal of peptides by ultrafiltration, the deproteinized whey from one cycle may be used for equilibration of the column prior to the next processing cycle.

The eluted clear WPI fraction was then ultrafiltered through a 5,000 MW cut-off membrane to provide a concentration of 20×, diafiltered with 2× RO water, and spray dried to produce clear WPI powder. HPLC analysis was then conducted on the clear WPI powder.

In addition to the methods described above, methods to produce cloudy and clear WPI were conducted using Express Ion Exchange S (Whatman, Fairfield, N.J.). Similar results were obtained using this resin. Thus, it is apparent that various resins may be substituted in the present methods. In addition, it was determined that all buffers, whey, and cleaning solutions may be successfully used at either room or elevated temperatures (e.g., 15 to 50° C.).

EXAMPLE 18

Production of α-Lactalbumin-Enriched WPI and Individual Protein Isolates

In this Example, methods to produce WPI enriched in α-lactalbumin were developed.

In these methods "MACROPREP" (Bio-Rad) and "EXPRESS" Q (Whatman) were both tested in an RFC column. The resins were prepared by producing a slurry in 0.5 M NaCl (25–30%), and packing the column at a constant pressure (to approximately 20–25 psi). The resin was backwashed with water at 0.5 Cv/min flow rate for 5 min. The column was then run forward at the same flow rate for about the same amount of time or until the salt was completely washed out, as indicated by the conductivity. This process was used for each RFC column.

The column resin was conditioned by passing 2 CVs of regeneration base solution (0.5 M NaOH) at 0.4 CV/min, and washed with 2–4 CVs water, or until the conductivity reading is at baseline. Then, 2 CVs of regeneration acid (0.5 M IICl) were passed through the column at 0.4 CV/min. Acid residues were washed from the column with 4–5 CVs water, or until the conductivity reading was at baseline.

The resin was equilibrated with 3–5 equilibration buffer (0.05 M sodium acetate trihydrate, pH 6.3–6.5) at 0.4 CV/min., or until the pH of the buffer flow through was approximately the same as that of the buffer feed (i.e., load).

Microfiltered (MF) whey (approximately 2.4% protein and 10.8% total solids), pH 6.3 to 6.5, (1.5 CV) was loaded onto the column. The flow rate was 0.4 CV/min. The first 0.9 CV of flow through (equilibration buffer) were discarded and the flow through was collected when the UV pin on the recorder started to rise, indicating the presence of α-lactalbumin-enriched concentrated whey. The resin was washed with 2 CVs water at 0.4 CV/min. The collection of α-lactalbumin-enriched whey continued until the UV baseline was reached. The β-lactoglobulin was eluted from the column with 3 CVs of the elution buffer (0.05 M sodium acetate trihydrate and 0.5 NaCl, pH approximately 8.75), at 0.4 CV/min. The first 0.8–0.85 CVs of elution flow through were discarded. Collection of the β-lactoglobulin fraction began when the UV began to rise, and was stopped when the UV baseline was reached. The elution flow through was allowed to drain until 3 CVs of the elution buffer passed through the column. The resin was cleaned with 2–3 CVs water at 0.4 CV/min, or until the conductivity reached baseline. The column was then reequilibrated with 2–3 CVs of equilibration buffer at 0.4–0.6 CV/min. The pH of the equilibration flow through was checked prior to loading the next cycle.

Every 10–40 cycle, the column was conditioned as described above, instead of cleaned and reequilibrated. At the end of each processing day, 2 CVs of regeneration base solution loaded in the column, and left in the resin until the column was ready to be washed for the next cycle.

The flow-through (β-lactoglobulin-depleted WPI), enriched in α-lactalbumin was chilled to 2–5° C., and held until processed further by ultrafiltration or diafiltration and spray dried to produce an α-lactalbumin enriched WPI powder containing 60–65% α-lactalbumin (dry weight). Or, the α-lactalbumin-enriched WPI was processed further by adjusting the pH to 3.5 to 3.9, and loaded onto a second column packed with a cation exchange resin to adsorb all of the proteins, and the immunoglobulins, α-lactalbumin, BSA, and lactoferrin were eluted with the appropriate buffers, as described in Example 7. Each of these protein fractions were suitable for further processing (e.g., ultrafiltration or diafiltration) and spray-drying to produce immunoglobulins of $\geq 80\%$ purity, as well as BSA and lactoferrin at $\geq 75\%$ purity. The β-lactoglobulin fraction may be similarly ultrafiltered, diafiltered and spray dried to produce β-lactoglobulin powder at $\geq 85\%$ purity, as determined by HPLC, as described previously. All of the above protein powders were found to contain 90–94% protein (on a solid basis), as determined by Kjeldahl nitrogen determinations.

EXAMPLE 19

Production of α-Lactalbumin-Enriched WPCs and Individual Protein Isolates

In this Example, methods for production of α-lactalbumin-enriched WPCs and individual protein isolates were developed. The column was packed, and the resin conditioned and equilibrated as described in the previous Example (Example 18). Single strength, clarified, separated, pasteurized chilled or warm whey (pH 6.3–6.5) was loaded onto the column (7 CVs) at 0.4–0.5 CV/min flow rate. The first 0.9 CV of flow through (equilibration buffer) was discarded, and the flow-through was collected when the absorbance began to rise, indicating the presence of α-lactalbumin-enriched whey. The column was washed with 2 CVs water at 0.4–0.6 Cv/min flow rate, and the collection of α-lactalbumin-enriched whey continued until the absorbance reached baseline.

Then, β-lactoglobulin was eluted and collected as described above in Example 18, and the column was cleaned with 2–3 CVs water at 0.4 CV/min, or until the conductivity reached baseline. The column was then reequilibrated with 2–3 CVs of equilibration buffer at 0.4 to 0.6 CV/min. The pH of the equilibration flow through was monitored prior to loading the next cycle. Every third cycle, the resin was conditioned as described in Example 18, above, rather than cleaned and reequilibrated. At the end of each processing day, 2 CVs of the regeneration base solution were added to the column and left in the bed resin until ready to wash for the next cycle.

The flow through (i.e., β-lactoglobulin-depleted whey), rich in α-lactalbumin collected in the method may be chilled to 2–5° C., and held until it is processed further. For example, it may be ultrafiltered and/or diafiltered and spray-dried to produced α-lactalbumin-enriched WPC (i.e., 35, 50, or 80 WPC). Or, the pH of the flow through may be adjusted to 3.5 to 3.9, and loaded onto a second column packed with a cation exchange resin to adsorb all proteins, which can then be sequentially eluted as described in Example 7. Similarly, β-lactoglobulin powder at approximately 85% purity may be produced.

EXAMPLE 20

Functionality Comparisons

In this Example, five prototype products were tested for their gelation, water holding, foaming/whippability, and emulsification properties. These products included "SEPRALAC WPI" (i.e., whey protein concentrate that was run through a cation exchange column [either "MACRO-PREP" resin or "SEPRASORB" medium], to remove the non-protein portion of the whey, and then collectively desorbed from the column using one elution buffer [i.e., 0.05 M sodium phosphate and 0.5 M sodium chloride, pH 9–10]), a commercially available WPI product referred to as "BIPRO" (Davisco), and egg whites (Ballas).

The characteristics of gelation, water holding, foaming/whippability, and emulsification properties are of interest in the protein and food industry, as they provide information regarding the suitability of proteins for particular uses. Certain characteristics are more desirable than others when the product is to be incorporated into food or beverage products. For example, α-lactalbumin with superior foaming and foaming stability may be used in ice cream formulations to increase over-run (i.e., an indication of the amount of air incorporated as air cells within the structure of the ice cream; it is expressed in the formula $(W1-W2)/W2 \times 100$, in which WI is the weight of a given volume of ice cream mixture before freezing and aeration, and W2 is the same volume of finished ice cream), or in dessert or breakfast drinks, where consistency, texture, taste, and nutritional value are important considerations.

Other possible uses for whey protein products in beverages include fortifying fruit juices, soft drinks, and dairy-based beverages. Several characteristics are of interest in the production of these products, including solubility, emulsification, viscosity, turbidity (i.e., opacity), and nutritional quality. Depending upon the type of beverage product, the blend, pH stability, and heat stability of the purified whey proteins (e.g., α-lactalbumin and β-lactoglobulin) can be optimized for the desired properties of the finished product.

In confectionery products such as toffee, an excess of sugar such as lactose contributed by ingredients such as whey protein concentrates, may result in the production of an unacceptable sandy or grainy texture. Thus, the use of separated whey proteins may prove to be a superior ingredient in such products. In addition, these proteins may serve as egg white substitutes.

Various whey products are used in the manufacture of a number of dairy products, including yogurt, ricotta cheese, cream cheese, and cream-based dips. The functional properties of whey proteins are important in such applications include water holding, emulsification, aeration, and gelation.
Gelation and Water Holding Gelation is the result of a balance between the interactions that occur between polymer molecules and the interaction between these polymer molecules and the solvent in which they are present. When the balance of these interactions is appropriate, a network or meshwork (i.e., a "gel") results. This network is capable of holding large amounts of water and other materials. Although an understanding of the mechanism is not necessary in order to use the present invention, protein gelation occurs by means of a two-step process, and depends upon protein-protein interactions occurring an aqueous environment.

The properties a gel may impart to a food vary with the type of interactions between proteins and other ingredients, as well as the processing procedures used. The type of gel formed is a direct result of specific responses of proteins to applied forces encountered during preparation, processing and storage of the gel or product. Protein responses may be further modified by interactions with food ingredients such as other proteins, salts, fats, hydrocolloids, and starches.

The water holding capability of a composition is a function of water-protein interactions. This is largely due to situations in which the structure and conformation of proteins is determined by the water present, resulting from hydrogen bonding of the amino acid residues and water. Ion dipole and dipole-dipole interactions are also important in the interaction between protein and water, as are physicochemical forces, such as adsorption.

Water-soluble proteins do not bind water as readily as non-water-soluble proteins. For example, whey proteins are water soluble and do not bind water unless the proteins are denatured (e.g., by heat).

In this Example, the pH was tested first by first preparing a 100 g of a 6% w/w suspension of sample (SEPRALAC WPI, SEPRALAC β-lactoglobulin [SEPRALAC β-Lac], SEPRALAC α-lactalbumin [SEPRALAC α-Lac], BIOPRO, and egg white) in distilled water or water treated by reverse osmosis ("R. O. water" or "RO"). "SEPRALAC WPI" refers to whey or whey protein concentrate that was run through a cation exchange column (either "MACRO-PREP" resin or "SEPRASORB" medium), to remove the non-protein portion of the whey, and WPI was then collectively desorbed from the column using one elution buffer (i.e., 0.05 M sodium phosphate and 0.5 M sodium chloride, pH 9–10]). "SEPRALAC β-lactoglobulin" refers to whey or whey protein concentrate that was run through a cation exchange column (either "MACRO-PREP" resin or "SEPRASORB" medium), to remove the non-protein portion of the whey, and then individually desorbed from the column using one elution buffer (i.e., 0.1 M sodium acetate and 0.5 M sodium chloride, pH 4, or 0.5 M sodium citrate acetate, containing 0.5 M NaCl, 4.0, respectively]) to isolate β-lactoglobulin. This suspension was stirred for 30 minutes or until the sample was well suspended. The pH was then recorded. "SEPRALAC α-lactalbumin" refers to whey or whey protein concentrate that was run through a cation exchange (i.e., "MACROPREP" resin), to remove the non-protein portion of the whey, the β-lactoglobulin was then desorbed, and the α-lactalbumin was individually desorbed from the column using one elution buffer (i.e., 0.1 M sodium acetate and 0.1 M sodium chloride, pH 5.0).

In order to test the gelation properties, each of the five solutions was then divided into three parts, to create 6%, 4%, and 2% w/w solutions diluted with water containing 0.05 M NaCl, 0.05 M CaCl$_2$, along with a fourth part at 6% in RO water. The pH of each dilution was adjusted to pH 6.5. For each dilution, six test tubes were weighed and marked (T1). Four ml of each solution concentration were added to the six marked and weighed test tubes. Thus, at this point, there were six test tubes for each concentration of each of the five solutions. The tubes were sealed with thermal tape, and heated at 85° C. for 10 minutes. The test tubes were removed from the heat and cooled in an ice bath for 10 minutes. The test tubes were then removed from the ice bath and wiped dry. Each tube was observed for gelation by inverting the tube. The result for each tube was recorded, with "+" indicating the presence of a solid gel, "−" for no gelation, and "O" indicating the presence of a soft gel.

To test for water holding capacity, each tube which showed gelation was weighed (T2). Each set of six test tubes was divided into two groups. The first group was tested without damage, and the second group was labelled "ringed" and "crossed" by using a spatula to scratch the surface of the gel, and make two vertical cuts crossing each other in the gel.

The tubes were centrifuged at 1000×g for 10 minutes, removed from the centrifuge, and then carefully inverted over absorbent paper for 10 minutes, and then weighed (T3). The water holding capacity was determined using the formula: 100× (T3-T1)/(T2-T1).

Foaming and Viscosity

The term "foaming," describes the behavior of proteins at the air/water interface. Foams are complex, two-phase colloidal systems which contain, at least initially, a continuous liquid phase, and a gas phase that is dispersed as bubbles or air cells. During foaming, proteins diffuse rapidly to the interface and then undergo molecular rearrangements.

Foaming is important to various industries. For example, the food industry uses incorporation of air by aeration (e.g., bubbling at high pressure) for various products, including ice cream, other frozen desserts, and milkshakes.

Viscosity is another property of interest to industries such as the food industry. The viscosity of a protein is the result of protein-water interactions. As the temperature increases above 65° C., the relative viscosity of whey protein solutions increases, until the solution reaches 85° C. At this point, protein aggregation occurs, and further increases in viscosity results.

In this Example, foaming and viscosity were analyzed for each sample. First, for each of the five samples tested, a 150 g of a 6% w/w protein solution was prepared in room temperature (i.e., 25° C.) R. O. water. The solutions were mixed for 30 minutes or until well suspended. The pH of solutions were then adjusted to 6.5±0.1, with 1.0 N HCl or 1.0 N NaOH, as needed.

In order to generate foam, 100 ml of each whey protein solution was weighed in a tared graduated cylinder. The weights were recorded (W1). For each solution, 100 ml of whey protein solution was then placed in a mixer bowl and whipped for 9 minutes with a wire whip, at the #8 setting on a Kitchen Aid model K455-SS mixer (Kitchen Aid). The foam overrun for each sample was measured by first carefully scooping foam into a plastic cup (e.g., Solo refill cups). The cup was weighed, the foam weights recorded (i.e., foam and cup weight was subtracted by the tared cup weight in order to determine the weight of the foam; Wf). The percent foam overrun was then calculated using the formula (W1-Wf)×100/Wf.

Foam viscosity was then measured using a Brookfield viscometer model RVF and model D Helipath stand, and T-bar #"C," and the speed set at 4 rpm. For each sample, a cup used to measure foam overrun was placed below the viscometer. The end of the viscometer probe was placed about 2 mm from the top surface of the foam and the machine was turned on. The reading was recorded when the black dot reached the top of the foam in the cup.

Each sample was tested using this procedure. The three readings for each sample (i.e., one from each of the three cups used for each sample) were averaged and recorded.

The foam stability was then measured by first carefully decanting the liquid from the bottom of each cup of foam. The edge of each cup was then carefully blotted with tissue. The weight of each cup of foam was then taken, recorded, and designated as the "initial weight" (Iw). This process was repeated for each of the three cups for each sample. The cups were then left undisturbed for 20 minutes and each of the above steps repeated in order to determine the "final weight" (Fw). The foam stability was then calculated using the formula—foam stability=((Iw-Fw)/Iw)).

Emulsification

Emulsification describes the behavior of proteins at two normally immiscible phases (e.g., an oil/water interface). In the process of emulsification, energy is applied to disperse one phase into another "continuous phase." If the dispersed phase is oil and the continuous phase is water, than an oil-in-water emulsion is the result of the emulsification process. Conversely, if the continuous phase is oil and the dispersed phase is water, a water-in-oil emulsion is the result. Emulsions may be prepared with liquids, semi-liquids or solids.

Factors that affect whey protein emulsions include pH and ionic strength; denaturation of proteins by heat treatment also affects the emulsion properties. The emulsification capacity is the mg of oil per 100 mg protein at the inversion of a protein solution from oil-in-water to a water-in-oil emulsion. In this situation, the protein is present in the aqueous phase.

In this Example, the emulsification capacity of whey was determined using an "E-C cell," namely, an oil reservoir tubed into a burette positioned on the top of a 1 pint "Ball" mason jar. The jar was then placed on a Sunbeam blender (obtained from National Equipment Corporation, Bronx, N.Y.), with electrodes attached at or near the bottom of mason jar, (above the blender blades) and wired to a volt-ohm meter (VOM). An illustration of emulsifying capacity equipment is shown in FIG. 18.

Samples were prepared by first making 100 ml of a 0.2% protein dispersion (based on Kjeldahl analysis of dry sample; see e.g., R. L. Bradley et al., "Chemical and Physical Methods, 15.1 Proteins," in R. T. Marshall (ed.), *Standard Methods for the Examination of Dairy Products*, American Public Health Association, [1992], pp. 504–516). The pH was adjusted to 6.5 with HCl or NaOH, as needed. A 30 ml aliquot of this dispersion was placed into the E-C cell. The blender was then turned on for 20 seconds at "stir" with the VOM set at RX 10,000 (i.e., the VOM meter reading). Upon completion of mixing, the oil titration was begun and continued until the VOM read infinite resistance, as this indicated complete phase inversion. As soon as the VOM read infinite resistance, the oil flow was stopped immediately and the volume of oil recorded (in ml). The volume of oil emulsified per 100 mg of protein was then calculated.

The following table (Table 12) shows the chemical composition of these compounds, including the ash, calcium, chloride, fat, lactose, phosphate, sodium, moisture, protein, NPN (non-protein nitrogen). Tables 13 and 14 show the gelation, water holding, foaming/whippability (overrun, viscosity, and stability), and the emulsification characteristics of WPI α-lactalbumin, and β-lactoglobulin prepared according to the method of the present invention, as well as commercial WPI (BIOPRO), and egg white.

TABLE 12

Chemical Composition

| Prod. | Source | Moist (%) | Protein (%) | NPN (%) | Fat (%) | Lact. (%) | Ash (%) | Ca | Cl (%) | Phos. | Na | pH in R.O. |
|---|---|---|---|---|---|---|---|---|---|---|---|---|
| WPI* | D | 3.9 | 90.5 | 0.6 | 0.6 | <0.1 | 2.1 | 230 | <0.1 | 55 | 577 | 7.5 |
| EWP | B | 7.8 | 81.3 | 2.5 | 0.1 | 6.6 | 5.5 | 82 | 1.24 | 106 | 1370 | 7.41 |
| WPI | LOL | 4.3 | 90.5 | 0.6 | 1.2 | <0.1 | 1.8 | 171 | <0.01 | 20 | 518 | 6.93 |
| β-Lac. | LOL | 3.8 | 94.9 | 0.7 | 0.2 | <0.1 | 1.8 | 188 | <0.01 | 35 | 637 | 6.81 |
| α-Lac. | LOL | 4.3 | 95.1 | 0.5 | 0.2 | <0.1 | 2.5 | 20 | <0.01 | 98 | 1070 | 6.94 |

Prod. = Product
Moist. = Moisture
NPN = Non-protein nitrogen
Lact = Lactose
Ca = Calcium (mg)
Cl = Chloride (mg)
Phos. = Phosphate (mg)
Na = Sodium (mg)
WPI* = Whey Protein Isolate (BIOPRO)
EWP = Egg White Protein
β-Lac = β-lactoglobulin
α-lac = α-lactalbumin
D = Davisco
B = Ballas
LOL = Land O' Lakes

TABLE 13

Functionality Results--Gelation and Water Holding

| | Gelation (0.5 NaCl:05 CaCl$_2$) | | | RO | Water Holding (% weight retained) | | |
|---|---|---|---|---|---|---|---|
| Product | 6% | 4% | 2% | 6% | 6% | 4% | 2% |
| SEPRALAC WPI | Solid | Solid | Solid | Opaque | 100 | 100 | 100 |
| SEPRALAC α-Lac | Solid | Solid | Not Solid | Clear | 100 | 100 | 0 |
| SEPRALAC β-Lac | Solid | Solid | Not Solid | Opaque | 100 | 100 | 56 |

TABLE 13-continued

Functionality Results--Gelation and Water Holding

| Product | Gelation (0.5 NaCl:05 CaCl$_2$) | | | RO | Water Holding (% weight retained) | | |
|---|---|---|---|---|---|---|---|
| | 6% | 4% | 2% | 6% | 6% | 4% | 2% |
| BIOPRO | Solid | Solid | Solid | Milky | 100 | 98 | 0 |
| Egg White | Solid | Solid | Solid | Solid | 100 | 100 | 100 |

RO = Reverse Osmosis

TABLE 14

Functionality Results--Foaming/Whippability and Emulsification

| Product | Foaming/Whippability (6% Pr. Sol. in RO H$_2$O) | | | | Emulsification |
|---|---|---|---|---|---|
| | 6% (control) | Overrun | Viscosity | Stability | ml oil/100 mg. Pr. |
| SEPRALAC WPI | 0 | 779 | 8.2 | 68.4 | 500 |
| SEPRALAC α-Lac | 0 | 975 | 8.7 | 93.7 | 1300 |
| SEPRALAC β-Lac | 0 | 709 | 10.8 | 78.8 | 575 |
| BIOPRO | 0 | 664 | 7.7 | 69.8 | 400 |
| Egg White | 100 | 825 | 16.3 | 98 | 800 |

EXAMPLE 21

Preliminary Application Studies

The physicochemical attributes of whey that make it useful as a component of food products was investigated in this Example. The functional properties of proteins can be studied in less complex systems, such as models systems, as well as medium complexity systems such as model food systems, and highly complex systems such as food products. However, functionality testing in model systems has not been standardized within the food industry. This lack of standardization has presented challenges in comparing the results obtained in different laboratories. Nonetheless, model food systems in which the food formulation and processing are done approximately as in the industrial processing, are considered to be useful indicators of the functional properties of proteins. Although the results from model food systems are not directly transposable to food products, they have been considered to be more realistic than other model systems.

In this Example, a randomly selected tasting panel was asked to evaluate various products, using a scale of 0–9 (with 9 being the highest value), to score the sensory acceptability of each product. Identical formulation and preparation methods were used for each product, with the exception being the type of whey protein solid used. In each of these experiments, the whey protein solids included samples prepared according to the methods of the present invention, as described in Examples 2 and 12 (SEPRALAC, α-lac), as well as commercially prepared WPI (Davisco) and WPC (Western Dairy). The amount of the whey protein solids used in each sample was determined by total Kjeldahl nitrogen (i.e., "TKN" analysis). In this Example, four prototype food products were tested: a) a simulated sport drink; b) a fruit gel; c) ice cream; and d) cookies.

A. Sport Drink

In this experiment, a simulated sport drink containing 3% whey protein solids, 2% mineral complex (equal amounts of potassium, calcium, phosphorus, and sodium, were mixed together), 3% sucrose 3% clarified lime juice, 0.3% sodium citrate, 0.2% lime flavor, and 88.5% distilled water. The water was placed in a blender, and the dry ingredients were added. The ingredients were mixed on high speed to dissolve the dry ingredients. The formulated beverage was then heated to 75° C. for 30 minutes, packed into 8 ounce glass bottles, cooled to room temperature, tightly capped, and then stored at 4° C. overnight. The following day, the beverages were evaluated for protein solubility (i.e., suspension or precipitation), clarity (i.e., visual cloudiness), and flavor. For BIOPRO WPC, the overall score was 4, while for BIOPRO WPI, the overall score was 6. For both SEPRALAC WPI and SEPRALAC α-lac, the overall score was 8.

B. Fruit Gel

A fruit punch gel was formulated to include 4% of whey protein, 10% water, 8% sugar, 2.5% gelatin, 0.5% citric acid, 0.3% sodium citrate, 74% clarified fruit punch juice (pineapple and grape flavor)(Florasynth, Teterboro, N.J.) and color (Virginia Dare, Brooklyn, N.Y.).

The dry ingredients were dissolved in distilled water and then heated slowly, with agitation, to 85° C. The solution was then held at this temperature for 5 minutes, poured into 6 ounce glass containers, cooled to room temperature, and then refrigerated overnight. The following day, the products were evaluated for gel strength, as tested by inversion and by pressing a spoon against the gel, smoothness (i.e., mouth feel), and flavor. For BIOPRO WPC, the overall score was 5, while for BIOPRO WPI, the overall score was 6. For SEPRALAC WPI, the overall score was 8.

C. Ice Cream

A 7000 gram ice cream mix containing 1200 g 40% sweet cream, 200 g milk, 420 g sugar, 250 g corn syrup, 200 g skim milk, 100 g skim milk powder, 4% whey protein, 21 g gums (cellulose, guar and carrageenan mono and diglycerides in "stabilizer mix" available from various sources including FMC), 7 g vanilla, 120 g dextrose was formulated, in which the whey proteins partially replaced milk proteins and gums.

The dry ingredients were added into the liquid ingredients, mixed, preheated, and passed through a single stage Gaulin homogenizer. The mixture was then mixed for 30 minutes, batch pasteurized at 165° F. for 30 minutes. The mixture was then mixed in order to provide aeration in a manual ice cream freezer for 10 minutes, and then packed into 8 ounce plastic cups. The packed cups were covered and placed at −20° C. for 24 hours. The resulting ice cream preparations were then evaluated for smoothness (i.e., mouth feel), lactose crystals, as indicated by sandiness, and stability (texture and firmness). The samples were allowed to sit at room temperature for 20 minutes and then evaluated for overrun (i.e., gain in volume of a given weight) and flavor (i.e., the presence of a whey flavor note). For BIOPRO WPC, the overall score was 5, while for BIOPRO WPI, the overall score was 7. For SEPRALAC WPI, the overall score was 7, while for SEPRALAC α-lac, the overall score was 8.

D. Cookies

A formulation containing 2% whey protein, flour (106 g), sugar (120 g), defatted wheat germ (15 g), vegetable shortening (25 g), salt (4 g), dextrose (40 g), soy lecithin (8 g), vanilla flavor (6 g), and water was prepared. The ingredients were mixed together with a mixer, until a smooth batter was produced. The batter was then spooned into cookie-sized balls on a cookie sheet or baking pan, and baked at 1 80° C. for 8 minutes. The cookies were cooled and kept at room temperature overnight. The following day, the cookies were evaluated for texture, volume, and mouth feel.

As shown in FIG. 16, the foods prepared using whey produced according to the methods of the present invention consistently scored higher than the foods prepared using the WPC (Western Dairy), and WPI (Davisco) obtained from commercially available sources. For BIOPRO WPC, the overall score was 4, while for BIOPRO WPI, the overall score was 6. For both SEPRALAC WPI and SEPRALAC α-lac, the overall score was 6.

EXAMPLE 22

Infant Formulae

It is contemplated that infant formulas be produced using whey produced according to the methods of the present invention. In this example, the casein and whey fractions of cow's milk were modified to achieve a composition simulating human milk to a significantly larger degree than prior art compositions and commercial products. The infant formulae of the present invention contain whey proteins at levels similar to those in human milk. This was achieved by producing a whey protein ingredient mix containing the type and ratio of whey proteins present in human milk.

Commercially available infant formulae are produced from whole cow's milk, largely due to its large scale availability. Other additives or adjuvants may be included. These formulas are manufactured either in powder, concentrated or ready to feed preparation. They consist, for the most part, of non-fat milk solids, vegetable oils and carbohydrate sweeteners such as lactose, corn syrup solids and sucrose. These formulae may also be fortified with vitamin C, vitamin D, iron and fluoride. Table 15 shows the typical compositions of a few exemplary commercial infant formulas in comparison to one exemplary formula of the present invention. Levels of vitamins, minerals and other fortifiers in the formulation of the present invention are adjusted to simulate human milk and to meet nutritional requirements of infants.

TABLE 15

Composition Range Of Some Commercial Infant Formulae Compared To One Exemplary Formulation Of The Present Invention

| Nutrients | Commercial Infant Formulas (Similac, Alimentum, Good Start, Gerber etc.) Per 5 Oz Prepared Feed (~12.5% Solids) | Formula Of Present Invention | | |
|---|---|---|---|---|
| | | Ingredients | Per 5 Oz Prepared Feed (~12.5% Solids) | Ingredients |
| Protein | 2.14–2.75 g | NFDM* - Casein hydrolysate - whey protein composition | 1.1–2.50 g | Dry or wet mix of purified, selected proteins |
| Fat | 5.1–5.54 g | veg, coconut, soy, palm, safflower, sun flower oil etc. | 4.30–6.48 g | veg oils, milk fat |
| Carbohydrate | 10.2–11.0 g | lactose, sucrose | 10.19–10.50 g | lactose |
| Water | 133–135 g | | 125–130 g | |
| Linoleic Acid | 850–1600 mg | | 1200–1300 mg | |
| Vit. A | 300 IU | | 300–350 IU | |
| Vit. D | 45–60 IU | | 50–60 IU | |
| Vit. E | 2.0–3.0 IU | | 2.2–2.7 IU | |
| Vit. C | 9 mg | | 7–9 mg | |
| Vit. K | 8–15 mcg | | 8–10 mcg | |
| Vit. B1 | 60–100 mcg | | 25–100 mcg | |
| Vit. B2 | 90–150 mcg | | 50–150 mcg | |
| Vit. B6 | 60–75 mcg | | 20–60 mcg | |
| Vit. B12 | 0.22–0.45 mcg | | 0.10–0.25 mcg | |
| Niacin | 750–1350 mcg | | 300–1100 mcg | |
| Folic Acid | 9–15 mcg | | 7–15 mcg | |
| Pantothenic Acid | 450–750 mcg | | 330–450 mcg | |
| Biotin | 2.2–4.5 mcg | | 2–4 mcg | |
| Choline | 8–16 mg | | 10–16 mg | |

TABLE 15-continued

Composition Range Of Some Commercial Infant Formulae
Compared To One Exemplary Formulation Of The Present Invention

| Nutrients | Commercial Infant Formulas (Similac, Alimentum, Good Start, Gerber etc.) Per 5 Oz Prepared Feed (~12.5% Solids) | Ingredients | Formula Of Present Invention Per 5 Oz Prepared Feed (~12.5% Solids) | Ingredients |
|---|---|---|---|---|
| Inositol | 4.7–18 mg | | 4.5–5.5 mg | |
| Calcium | 64–105 mg | | 47–73 mg | |
| Phosphorus | 36–75 mg | | 21–56 mg | |
| Magnesium | 6.0–7.5 mg | | 4.4–6.0 mg | |
| Iron | 0.5–1.8 mg | | 0.04–1.8 mg | |
| Zinc | 0.75 mg | | 0.25–0.75 mg | |
| Manganese | 5–30 mcg | | 5 10 mcg | |
| Copper | 75–90 mcg | | 75–90 mcg | |
| Iodine | 8–15 mcg | | 9–12 mcg | |
| Sodium | 24–44 mg | | 25–40 mg | |
| Potassium | 98–118 mg | | 75–110 mg | |
| Chloride | 59–80 mg | | 59–80 mg | |
| Cholesterol | — | | 18–25 mg | |

*NFDM - non-fat dry milk solids.

TABLE 16

Comparison Of Cow's Milk With Human Milk

| Per 100 g | Cow | Human |
|---|---|---|
| Water (g) | 89.99 | 87.5 |
| Food Energy (kcal) | 61 | 70 |
| Protein (N × 6.38) (g) | 3.29 | 1.03 |
| Fat (g) | 3.34 | 4.38 |
| Carbohydrate (total) (g) | 4.66 | 6.89 |
| Fiber (g) | 0 | 0 |
| Ash (g) | 0.72 | 0.2 |
| Minerals (mg): | | |
| Calcium | 119 | 32 |
| Iron | 0.05 | 0.03 |
| Magnesium | 13 | 3 |
| Phosphorus | 93 | 14 |
| Potassium | 152 | 51 |
| Sodium | 49 | 17 |
| Zinc | 0.38 | 0.17 |
| Vitamins: | | |
| Ascorbic Acid (mg) | 0.94 | 5.00 |
| Thiamin (mg) | 0.038 | 0.014 |
| Riboflavin (mg) | 0.162 | 0.036 |
| Niacin (mg) | 0.084 | 0.177 |
| Pantothenic Acid (mg) | 0.314 | 0.223 |
| Vitamin $B_6$ (mg.) | 0.042 | 0.011 |
| Folic Acid (mcg) | 5 | 5 |
| Vitamin $B_{12}$ (mcg) | 0.357 | 0.045 |
| Vitamin A (I.U.) | 126 | 241 |
| Cholesterol (mg) | 14 | 14 |

TABLE 17

Protein Composition Of (Cow & Human Milk) g/100 g

| Protein | Cow | Human |
|---|---|---|
| Casein (total) | 2.6 | 0.32 |
| β-Lactoglobulin | 0.32 | Negligible |
| α-Lactalbumin | 0.12 | 0.28 |
| Serum albumin | 0.04 | 0.06 |
| Lysozyme | Negligible | 0.04 |
| Lactoferrins | 0.02 | 0.20 |
| Immunoglobulins | 0.07 | 0.10 |

A ratio of the various whey proteins between cow's and human milk, along with a comparison of suggested formulation mixtures are presented in Table 18 below.

TABLE 18

Ratio Of Various Whey Proteins In Cow's & Human Milk

| Protein | Cow's Milk (g/100 g) | Human Milk | % | Ratio H/C | Mix Composition of Suggested Formulations |
|---|---|---|---|---|---|
| α-La | 0.12 | 0.28 | 43.75 | 2.33 | 43.5 |
| L-Fe | 0.02 | 0.20 | 31.25 | 10 | 31.6 |
| IgG | 0.07 | 0.10 | 15.63 | 1.43 | 15.4 |
| BSA | 0.04 | 0.06 | 9.37 | 1.5 | 9.5 |

As shown in the foregoing tables, cow's milk contains 3.3% protein while human milk has only 1%. Of these proteins, caseins are the major protein components in cow's milk (about 77% of total protein). However, human milk contains a high ratio of whey proteins to caseins (about 2:1). In addition, the β-lactoglobulin concentration in cow's milk is the highest of the whey proteins, while it is negligible in human milk. Similarly, lactoferrin is ten times higher in concentration in human milk than in cow's milk. Immunoglobulin and serum albumin concentrations are about 1.5 times higher in human milk than in cow's milk.

In the infant formula of the present invention, lactose and fat levels are adjusted to simulate human milk. In many formulae, vegetable fat is used in place of butter fat and the casein to whey ratio is also reduced to simulate human milk, and the total solute load is reduced to the level found in human milk. Other additives and supplements such as vitamins, taurine, and minerals may be included if desired.

To achieve this objective, whey protein fractions obtained from the fractionation and elution in accordance with the process of this invention, were first combined in the ratio shown in Table 19 below.

TABLE 19

Dietary Formulation A

| | |
|---|---|
| α-Lactalbumin Fraction | 43.5% |
| Lactoferrin Fraction | 31.6% |
| Immunoglobulin Fraction | 15.4% |
| Bovine Serum Albumin Fraction | 9.5% |

The above whey protein mix was then incorporated into a human milk-like formulation with the composition shown in Table 20, below.

TABLE 20

Infant Formula

| Ingredient | | Liquid Formula (g/100 g) | Dry Formula Base (g/6 oz liquid) |
|---|---|---|---|
| Water | | 87.20 | 0 |
| β-Casein | | 0.28 | 0.504 |
| κ-Casein | | 0.04 | 0.072 |
| Prepared whey protein mix | α-La BSA →→ L-Fe Ig-G | 0.64 | 1.152 |
| Lysozyme | | 0.04 | 0.072 |
| Lactoperoxidase | | 0.006 | 0.012 |
| Fat | | 4.5 | 8.1 |
| Lactose | | 7.0 | 12.6 |
| Ash | | 0.2 | 0.36 |

For lactoperoxidase, the liquid formula contained with an activity level of 750 units, while the dry formula contained an activity of 1350 units. The unit activity was defined as the amount of lactoperoxidase that formed 1.0 mg pupurogallin from pyrogallol in 20 seconds at 20° C., and pH 6.0. For the liquid formula, the average activity was 115 units (the typical range for bovine lactoperoxidase is 50–150).

The liquid mix prepared according to the above composition contained about 2% total solids (of which salts from the eluting buffers comprise 90% and total proteins comprise about 10%), and 98% water. This liquid mix was then concentrated through a 5,000 molecular weight cut-off, spiral ultrafiltration membrane (Abcor) to a content of 5–15% total proteins, followed by diafiltration with distilled water 5–10 times, to remove remaining salt residues. This formulation may be further concentrated by processes normally utilized in the treatment of labile proteins, such as ultrafiltration, freeze drying, freeze concentration, spray drying and the like or any combination thereof. The formulations of this invention may be further fortified with suitable additives and fortifiers. Such additives and fortifiers include but are not limited to nonfat milk solids, vegetable solids, carbohydrate sweeteners, minerals and vitamins. The solid composition of one exemplary formulation of the present invention is presented in Table 21, below.

TABLE 21

Solid Composition Of One Exemplary Formulation Of The Present Invention

| Ingredients | gm/16 oz of Formula Powder |
|---|---|
| Proteins: | |
| Casein Hydrolysate | 11.00 |
| α-Lactalbumin | 9.63 |
| Bovine Serum Albumin | 2.06 |
| Lactoferrin | 6.88 |
| Immunoglobulins | 3.44 |
| Lysozyme | 1.38 |
| Fat: | |
| Coconut Oil | 53.56 |
| Sunflower Oil | 46.08 |
| Corn Oil | 36.79 |
| Butter Fat | 14.10 |
| Carbohydrate: | |
| Lactose | 236.95 |
| Moisture (Water Content): | 15.20 |
| Linoleic Acid: | 2.41 |
| Vitamins: | |
| Vit. A | 8288 (IU) |
| Vit. D | 1720 (IU) |
| Vit. E (tocopherol) | 86 (IU) |
| Vit. K | 0.0003 |
| Vit. $B_1$ | 0.0018 |
| Vit. $B_2$ | 0.0012 |
| Vit. $B_6$ | 0.0004 |
| Vit. $B_{12}$ | 0.0000002 |
| Vit. C (ascorbic acid) | 0.17 |
| Niacin | 0.0001 |
| Folic Acid | 0.0001 |
| Pantothenic Acid | 0.008 |
| Biotin | 0.34 |
| Choline | 0.34 |
| Inositol | 0.18 |
| Minerals: | |
| Calcium | 1.10 |
| Phosphorus | 0.48 |
| Magnesium | 0.10 |
| Iron | 0.001 |
| Zinc | 0.006 |
| Manganese | 0.0003 |
| Copper | 0.003 |
| Iodine | 0.0003 |
| Sodium | 0.59 |
| Potassium | 1.76 |
| Chloride | 2.06 |
| Cholesterol | 0.48 |

EXAMPLE 23

Formulations As Fat Substitutes

It is also contemplated that other components separated from whey using the present invention will be utilized in various capacities. For example, β-lactoglobulin exhibits high water-binding qualities and α-lactalbumin increases viscosity and also absorbs a high content of fat and oils. Because of these properties, a combination of these proteins lends itself to use as a fat substitute. This product when incorporated in appropriate proportions into some food products improves the quality and characteristics of the product and may be used as a fat substitute.

As shown in Example 1, β-lactoglobulin along with immunoglobulins eluted as fraction 2, while α-lactalbumin eluted in fraction 3. The immunoglobulin was separated from the β-lactoglobulin fraction as described in Example 7. The β-lactoglobulin fraction was then mixed with the α-lactoglobulin fraction in a 60 and 40% ratio. The mix of the two proteins (β-La+α-La) was passed through a 5,000 molecular weight cut-off ultra-filtration membrane (Abcor) at 40° F. with a differential pressure of 10 psi and the permeate, consisting of water and soluble salts, was removed until a 10–15% total solids concentration was achieved. This was followed by a diafiltration with distilled water to remove remaining salt residues. Diafiltration was accomplished by adding distilled water in a volume that was five times the volume of ultrafiltered concentrate, mixed, and removed as permeate. This washed out the salts to a level of <1% total solids.

The concentrated and purified mix obtained may be used as is, frozen, freeze-dried, chilled or dehydrated for further use. In addition, other additives such as flavor enhancers, gums, vitamins and sweeteners may be included in these formulations as desired. It is contemplated that the concentrated and purified mix will be pasteurized and/or homogenized either before or after the addition of other desired ingredients.

From the above Examples, it is clear that the present invention represents an unexpected and much improved system for the economical, efficient, and rapid separation of whey proteins in many uses and formats (or configurations) and in particular, provides a major advance in the production of formulations useful for infant formula and fat substitutes.

In summary, the present invention provides numerous advances and advantages over the prior art, including: (1) much greater efficiency in production, as larger throughput is possible; (2) much greater economy, as the methods would not require expensive renovations to most existing facilities; and (3) provision of new, functional, essential ingredients previously unavailable in commercial quantities for development of new food products. It is contemplated that the present invention will find use in other commercial separation and/or purification methods for high value components of various foodstuffs, medicines, etc.

It is not intended that the present invention be limited to these particular embodiments. All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in food production, separation science, chromatography, and/or related fields are intended to be within the scope of the following claims.

We claim:

1. A method for the sequential separation of whey proteins, comprising the steps of:
   a) providing:
      i) a cationic exchange resin contained within a container;
      ii) a whey sample, wherein said whey sample comprises at least one whey protein selected from the group consisting of immunoglobulin, β-lactoglobulin, α-lactalbumin, lactoperoxidase, serum albumin, and lactoferrin; and
      iii) a cationic exchange resin;
   b) passing said whey sample through said resin under conditions whereby said whey proteins adsorb to said resin;
   c) collecting the flow-through from said cationic exchange resin, wherein said flow-through comprises lactose, minerals, lactic acid, and non-nitrogenous components;
   d) sequentially eluting said immunoglobulin and said β-lactoglobulin from said cationic exchange resin;
   e) eluting said α-lactalbumin from cationic exchange resin;
   f) eluting said serum albumin from cationic exchange resin;
   g) eluting said lactoferrin from said cationic exchange resin; and
   h) eluting said lactoperoxidase from said cationic exchange resin;
wherein a sequential separation of whey proteins is achieved.

2. The method of claim 1, wherein said whey is selected from the group consisting of pasteurized sweet whey, pasteurized acid whey, non-pasteurized acid whey, and whey protein concentrate.

3. The method of claim 1, wherein said container comprises a radial flow column.

4. The method of claim 1, wherein said container comprises an axial flow column.

5. The method of claim 1, wherein said container is selected from the group consisting of beakers, tanks, vats, and chambers.

6. The method of claim 1, wherein said cationic exchange resin comprises a cellulosic matrix.

7. The method of claim 1, wherein said cationic exchange resin is selected from the group consisting of co-polymerized glycidyl methacrylate, and cross-linked diethylene glycol.

8. The method of claim 1, wherein said steps e), f), g) and h), utilize a buffer.

9. The method of claim 6, wherein said cationic exchange resin comprises cross-linked flexible sponge absorbent.

10. The method of claim 8, wherein said buffer is selected from the group consisting of whey buffer, permeate, and modified whey buffer.

11. The method of claim 8, wherein said buffer is recycled.

12. The method of claim 9, wherein said cross-linked flexible sponge absorbent comprises substantially uniformly distributed fibrous reinforcement.

13. A two-column method for the separation of whey proteins comprising the steps of:
   a) providing:
      i) anionic exchange resin present within a first container to produce a first resin;
      ii) a whey sample containing β-lactoglobulin, immunoglobulins, α-lactalbumin, serum albumin, and lactoferrin, and a soluble portion;
      iii) cationic exchange resin present within a second container to produce a second resin; and
      iv) an ultrafiltration membrane;
   b) passing said whey sample through said first resin under conditions wherein said β-lactoglobulin adsorbs to said first resin and said soluble portion passes through the column to form a flow-through;
   c) collecting said flow-through from said first resin, wherein said flow-through comprises α-lactalbumin, immunoglobulins, serum albumin and lactoferrin suitable for further processing;
   d) eluting said adsorbed β-lactoglobulin from said first resin to produce an eluate;

e) passing said flow-through collected in step c) through said ultrafiltration membrane to produce an ultrafiltrate;
f) passing said ultrafiltrate through said second resin, under conditions such that immunoglobulins, α-lactalbumin, serum albumin, and lactoferrin adsorb to said second resin;
g) eluting said immunoglobulins from said second resin;
h) eluting said α-lactalbumin from said second resin;
i) eluting said serum albumin from said second resin; and
j) eluting said lactoferrin from said second resin;
thereby separating whey proteins.

14. The method of claim 13, wherein said first resin is reconditioned.

15. The method of claim 13, wherein said second resin is reconditioned.

16. The method of claim 13, wherein said second container is selected from the group consisting of radial flow chromatography columns, axial flow chromatography columns, beakers, vats, tanks, and chambers.

17. The method of claim 13, further comprising the step:
k) cleaning said first and second resin with a cleaning buffer.

18. The method of claim 13 wherein said cleaning buffer comprises sodium hydroxide, sodium chloride and ethanol.

19. The method of claim 13, wherein said flow through comprises a formula comprising at least one whey protein.

20. The method of claim 19, further comprising the step of diafiltering said formula.

21. The method of claim 19, wherein said formula comprises a nutritional formula selected from the group consisting of sports drinks, fruit gels, ice cream, and cookies.

22. The method of claim 19, wherein said formula comprises an infant food.

23. The method of claim 19, wherein said formula is freeze dried.

24. The method of claim 19, wherein said formula is frozen.

25. The method of claim 19, wherein said formula is spray dried.

26. The method of claim 20, wherein said infant food is non-allergenic.

27. A method for processing whey comprising the steps of:
a) providing:
i) a cation exchange resin; and
ii[i]) a whey sample, wherein said whey sample comprises whey proteins;
b) passing said whey sample through said cation exchange resin under conditions whereby said whey proteins adsorb to said cation exchange resin, and a flow through passes through said cation exchange resin;
c) collecting said flow-through, wherein said flow-through comprises deproteinized whey;
thereby processing whey.

28. The method of claim 27, further comprising an anion exchange resin.

29. The method of claim 28, comprising the further steps of:
d) passing said deproteinized whey through said anion exchange resin under conditions such that any whey proteins present in said deproteinized whey adsorb to said anion exchange resin; and
e) eluting said remaining whey proteins from said anion exchange resin.

30. The method of claim 28, further comprising the step of f) washing said whey proteins to produce clear whey protein isolate.

31. The method of claim 28, wherein said cation exchange resin comprises a chromatography column selected from the group consisting of radial flow columns and axial flow columns.

32. The method of claim 28, wherein said whey proteins adsorbed to said cation exchange resin are eluted from said cation exchange resin.

33. The method of claim 28, wherein said cation exchange resin is washed following step b) to produce a wash buffer.

34. The method of claim 28, wherein said cation exchange resin is a weak acid cation exchange resin.

35. The method of claim 28, wherein said anion exchange resin is a weak base anion exchange resin.

36. The method of claim 28, further comprising the step of:
f) reconditioning said cation exchange resin with a buffer.

37. The method of claim 29, wherein said anion exchange resin comprises a chromatography column selected from the group consisting of radial flow columns and axial flow columns.

38. The method of claim 29, further comprising the step of
g) reconditioning said anion exchange resin with a buffer.

39. The method of claim 33, wherein said wash buffer comprises non-protein nitrogen.

40. The method of claim 34, wherein said weak acid cation exchange resin is a carboxoymethyl resin.

41. The method of claim 35, wherein said weak base anion exchange resin is a dithylaminoethyl resin.

42. The method of claim 36, wherein said buffer comprises deproteinized whey.

43. The method of claim 38, wherein said buffer comprises deproteinized whey.

44. The method of claim 39, wherein said wash buffer further comprises lactose, minerals, lactic acid, and vitamins.

45. A method for the production of clear whey protein isolate comprising:
a) providing:
i) a cation exchange resin; and
ii) a whey sample, wherein said whey sample comprises serum albumin, lipoprotein, whey protein, and a soluble portion;
b) passing said whey sample through said cation exchange resin, under conditions that said whey protein, serum albumin, and lipoprotein adsorbs to said cation exchange resin, and said soluble portion flows through said cation exchange resin to produce a flow-through;
c) eluting said whey protein adsorbed to said cation exchange resin to provide clear whey protein isolate; and
d) eluting said serum albumin and fat from said cation exchange resin;
thereby producing clear whey protein isolate.

46. The method of claim 45, wherein said clear whey protein isolate comprises α-lactalbumin, β-lactoglobulin, and immunoglobulin.

47. The method of claim 45, wherein said eluting said whey protein adsorbed to said cation exchange resin is accomplished using a clear whey protein isolate elution buffer.

48. The method of claim 45, wherein said clear whey protein isolate elution buffer comprises sodium acetate and sodium chloride.

49. The method of claim 45, wherein said eluting said serum albumin and said lipoprotein is accomplished using serum albumin buffer.

50. The method of claim 45, wherein said serum albumin buffer comprises sodium chloride, and a salt selected from the group consisting of sodium acetate, and sodium citrate.

51. The method of claim 45, wherein said whey protein isolate elution buffer is recycled.

52. The method of claim 45, wherein said whey protein isolate elution buffer comprises said flow-through.

53. The method of claim 45, wherein said serum albumin buffer is recycled.

54. The method of claim 45, wherein said whey protein isolate elution buffer comprises deproteinized whey.

55. The method of claim 45, wherein said clear whey protein isolate elution buffer is whey buffer.

56. The method of claim 45, comprising the further steps of:
   e) ultrafiltering said clear whey protein isolated obtained in step b) to produce an ultrafiltrate;
   f) diafiltering said ultrafiltrate to produce a diafiltered ultrafiltrate.

57. The method of claim 54, wherein said deproteinized whey is recycled.

58. The method of claim 56, further comprising the step of spray drying said diafiltered ultrafiltrate to produce clear whey protein isolate powder.

59. A method for the production of α-lactalbumin-enriched whey protein isolate comprising:
   a) providing: i) anion exchange resin; and ii) whey comprising α-lactalbumin and β-lactoglobulin; and
   b) passing said whey through said anion exchange resin under conditions such that said β-lactoglobulin binds to said anion exchange resin and said α-lactalbumin flows through said anion exchange resin, to produce whey enriched in α-lactalbumin.

60. The method of claim 59, further comprising the step of:
   c) eluting said β-lactoglobulin from said anion exchange resin.

61. A method for cleaning resin contained within a chromatography column, comprising the steps of:
   a) providing:
      i) resin contained within a container;
      ii) sodium hypochlorite;
      iii) sodium hydroxide;
      iv) hydrochloric acid;
      v) ethanol;
   b) washing said resin with said sodium hypochlorite to produce washed resin;
   c) exposing said washed resin to said sodium hydroxide to produce a base-treated resin;
   d) exposing said base-treated resin to said hydrochloric acid to produce an acid-treated resin; and
   e) exposing said acid-treated resin with said ethanol to produce a cleaned resin;
thereby cleaning the resin.

62. The method of claim 61, further comprising step f) equilibrating said cleaned resin.

63. The method of claim 61, wherein said washed resin is rinsed with water prior to washing with said sodium hypochlorite.

64. The method of claim 61, wherein said base-treated resin is rinsed with water prior to exposing to said hydrochloric acid.

65. The method of claim 61, wherein said acid-treated resin is rinsed with water prior to exposure to ethanol.

66. The method of claim 61, comprising the further step of passing said whey enriched in α-lactalbumin through a cation exchange resin.

* * * * *